(12) United States Patent
Shin et al.

(10) Patent No.: US 12,029,113 B2
(45) Date of Patent: Jul. 2, 2024

(54) ORGANIC COMPOUND HAVING IMPROVED LUMINESCENT PROPERTIES, ORGANIC LIGHT EMITTING DIODE AND ORGANIC LIGHT EMITTING DEVICE INCLUDING THE ORGANIC COMPOUND

(71) Applicant: LG DISPLAY CO., LTD., Seoul (KR)

(72) Inventors: In-Ae Shin, Paju-si (KR); Suk-Young Bae, Paju-si (KR); Kyung-Jin Yoon, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 488 days.

(21) Appl. No.: 17/011,748

(22) Filed: Sep. 3, 2020

(65) Prior Publication Data
US 2021/0066612 A1    Mar. 4, 2021

(30) Foreign Application Priority Data

Sep. 4, 2019  (KR) .................. 10-2019-0109452

(51) Int. Cl.
*H10K 85/60* (2023.01)
*C07D 401/14* (2006.01)
(Continued)

(52) U.S. Cl.
CPC ......... *H10K 85/654* (2023.02); *C07D 401/14* (2013.01); *C09K 11/06* (2013.01);
(Continued)

(58) Field of Classification Search
CPC .. H05K 85/654; C07D 401/14; C07D 405/14; C07D 401/04; C09K 11/06;
(Continued)

(56) References Cited

U.S. PATENT DOCUMENTS

2005/0127823 A1\* 6/2005 Iwakuma ............. H10K 85/342
548/440
2005/0206305 A1\* 9/2005 Masuda ............... H10K 50/125
313/504
(Continued)

FOREIGN PATENT DOCUMENTS

CN   102372695 A  \*  3/2012
CN   103261158 A  \*  8/2013  ........... C07D 209/88
(Continued)

OTHER PUBLICATIONS

Machine translation of description of KR 10-2017-0047933 A (publication date: May 2017). (Year: 2017).\*
(Continued)

*Primary Examiner* — Dawn L Garrett
(74) *Attorney, Agent, or Firm* — Morgan, Lewis & Bockius LLP

(57) ABSTRACT

The present disclosure relates to an organic compound having improved luminescent properties, an organic light emitting diode and organic light emitting device including the organic compound, the organic compound having the following structure. The organic compound is a bipolar compound having both a p-type moiety and an n-type moiety and has high energy level, large energy bandgap and improved thermal stability. Applying the organic compound into an emissive layer of the OLED allows holes and electrons to be recombined at whole area of an emitting material layer, and thereby enhancing the luminous efficiency and the luminous lifetime of the OLED.

(Continued)

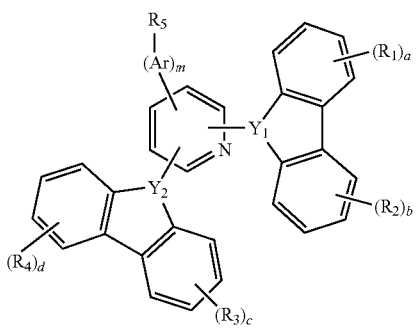

17 Claims, 11 Drawing Sheets

(51) Int. Cl.
*C09K 11/06* (2006.01)
*H10K 50/13* (2023.01)
*H10K 50/16* (2023.01)
*H10K 50/18* (2023.01)

(52) U.S. Cl.
CPC .. *H10K 85/6572* (2023.02); *C09K 2211/1059* (2013.01); *H10K 50/13* (2023.02); *H10K 50/16* (2023.02); *H10K 50/18* (2023.02)

(58) Field of Classification Search
CPC ...... C09K 211/1059; C09K 2211/1007; C09K 2211/1011; C09K 2211/1029; C09K 2211/1088; H10K 85/6572; H10K 50/13; H10K 50/16; H10K 50/18; H10K 50/131; H10K 2101/20; H10K 50/11; H10K 50/12; H10K 85/615; H10K 85/6574; H10K 2101/10; H10K 2101/40; H10K 50/14; H10K 85/657
See application file for complete search history.

(56) References Cited

U.S. PATENT DOCUMENTS

| 2009/0066245 A1* | 3/2009 | Sugimoto | H10K 85/622 |
| | | | 548/131 |
| 2009/0072727 A1 | 3/2009 | Takeda | |
| 2012/0126221 A1* | 5/2012 | Kitamura | H10K 85/654 |
| | | | 257/E51.026 |
| 2016/0087227 A1 | 3/2016 | Younsun et al. | |
| 2017/0062752 A1* | 3/2017 | Ihn | H05B 33/14 |

FOREIGN PATENT DOCUMENTS

| CN | 110335969 A | * | 10/2019 | ......... H01L 51/001 |
| CN | 114105868 A | * | 3/2022 | |
| CN | 114105956 A | * | 3/2022 | |
| EP | 2039737 A2 | | 3/2009 | |
| JP | 2013108015 A | * | 6/2013 | |
| KR | 20100103837 A | * | 9/2010 | |
| KR | 10-2017-0047933 A | | 5/2017 | |
| WO | WO-03080761 A1 | * | 10/2003 | ............ C09K 11/06 |
| WO | WO-2013108589 A1 | * | 7/2013 | ............ C07D 401/14 |

OTHER PUBLICATIONS

Chatterjee, T., Hung, W.Y., Tang, W.F., Chen, H.F. and Wong, K.T., 2017. Carbazole-bridged triphenylamine-bipyridine bipolar hosts for high-efficiency low roll-off multi-color PhOLEDs. Organic Electronics, 50, pp. 204-212. (Year: 2017).*
Machine translation of KR 20100103837 A (publication date Sep. 2010). (Year: 2010).*
Machine translation for WO 2013/108589 A1 (publication date Jul. 2013). (Year: 2013).*
Machine translation of CN 110335969 A (publication date Oct. 2019). (Year: 2019).*
Tang, Chao, et al. "A versatile efficient one-step approach for carbazole-pyridine hybrid molecules: highly efficient host materials for blue phosphorescent OLEDs." Chemical Communications 51.9 (2015): 1650-1653. (Year: 2015).*
Yu Gu et. al "Adamantane-Based Wide-Bandgap Host Material: Blue Electrophosphorescence with High Efficiency and Very High Brightness" Chemistry – A European Journal / vol. 21, Issue 22 Apr. 21, 2015.
Extended European Search Report dated Jan. 27, 2021, issued in corresponding European Patent Application No. 20193890.9.

* cited by examiner

ORGANIC COMPOUND HAVING IMPROVED LUMINESCENT PROPERTIES, ORGANIC LIGHT EMITTING DIODE AND ORGANIC LIGHT EMITTING DEVICE INCLUDING THE ORGANIC COMPOUND

CROSS-REFERENCE TO RELATED APPLICATIONS

This application claims the priority benefit under 35 U.S.C. § 119(a) of Korean Patent Application No. 10-2019-0109452, filed in the Republic of Korea on Sep. 4, 2019, which is incorporated herein by reference in its entirety.

BACKGROUND

Technical Field

The present disclosure relates to an organic compound, and more specifically, to an organic compound having enhanced luminous properties, an organic light emitting diode and an organic light emitting device including the compound.

Discussion of the Related Art

As display devices have became larger, there exists a need for a flat display device with a lower space requirement. Among the flat display devices used widely at present, organic light emitting diodes (OLEDs) are rapidly replacing liquid crystal display devices (LCDs). The OLED can be formed as a thin film having a thickness less than 2000 Å and can be implement unidirectional or bidirectional images as electrode configurations. In addition, OLEDs can be formed on a flexible transparent substrate such as a plastic substrate so that OLED can implement a flexible or foldable display with ease. Moreover, the OLED can be driven at a lower voltage of 10 V or less. Besides, the OLED has relatively lower power consumption for driving compared to plasma display panels and inorganic electroluminescent devices, and the color purity of the OLED is very high.

In the OLED, when electrical charges are injected into an emitting material layer between an electron injection electrode (i.e., cathode) and a hole injection electrode (i.e., anode), electrical charges are recombined to form excitons, and then emit light as the recombined excitons are shifted to a stable ground state. Since only singlet excitons in the common fluorescent material according to the related art can be involved in luminous process, luminous efficiency of the common fluorescent material is low. On the contrary, the phosphorescent material of the related art in which triplet excitons as well as singlet excitons participate in the luminous process show high luminous efficiency compared to the common fluorescent material. However, since a metal complex as a representative phosphorescent material has a short luminous lifetime, its commercial applications have been limited.

SUMMARY

Accordingly, embodiments of the present disclosure are directed to an organic compound and an OLED and an organic light emitting device including the organic compound that substantially obviate one or more of the problems due to the limitations and disadvantages of the related art.

An aspect of the present disclosure is to provide an organic compound having high excited triplet energy level and a bipolar property, an OLED and an organic light emitting device into which the organic compound is applied in an emissive layer.

Another aspect of the present disclosure is to provide an organic compound improving thermal stability and having enhanced affinity to charges, an OLED and an organic light emitting device having the compound.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

To achieve these and other aspects of the inventive concepts, as embodied and broadly described, the present disclosure provides an organic compound having the following structure of Chemical Formula 1:

[Chemical Formula 1]

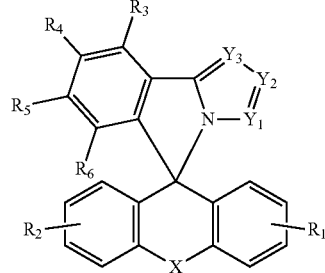

wherein each of $R_1$ to $R_4$ is independently selected from the group consisting of protium, deuterium, tritium, $C_1$-$C_{20}$ alkyl, $C_1$-$C_{20}$ alkoxy, $C_1$-$C_{20}$ alkyl amino, $C_6$-$C_{30}$ aryl, $C_3$-$C_{30}$ hetero aryl, $C_7$-$C_{30}$ aralkyl, $C_3$-$C_{30}$ hetero aralkyl, $C_6$-$C_{30}$ aryloxy, $C_3$-$C_{30}$ hetero aryloxy, $C_6$-$C_{30}$ aryl amino, $C_3$-$C_{30}$ hetero aryl amino and an adamantyl group, or when each of a to d is an integer of 2 or more, each of two adjacent $R_1$ groups, two adjacent $R_2$ groups, two adjacent $R_3$ groups and two adjacent $R_4$ groups independently forms an unsubstituted or substituted fused aromatic ring or an unsubstituted or substituted $C_3$-$C_{20}$ fused hetero aromatic ring; $R_5$ is selected from the group consisting of protium, deuterium, tritium, $C_1$-$C_{20}$ alkyl, $C_1$-$C_{20}$ alkoxy, $C_1$-$C_{20}$ alkyl amino, $C_6$-$C_{30}$ aryl, $C_3$-$C_{30}$ hetero aryl, $C_7$-$C_{30}$ aralkyl, $C_3$-$C_{30}$ hetero aralkyl, $C_6$-$C_{30}$ aryloxy, $C_3$-$C_{30}$ hetero aryloxy, $C_6$-$C_{30}$ aryl amino, $C_3$-$C_{30}$ hetero aryl amino and an adamantyl group, wherein at least one of $R_1$ to $R_5$ is the adamantyl group; each of a, b, c, d is the number of substituent and is independently an integer of 0 (zero) to 4; Ar is $C_6$-$C_{30}$ arylene or $C_3$-$C_{30}$ hetero arylene; m is an integer of 0 (zero) or 1; each of $Y_1$ and $Y_2$ is independently selected from the group consisting of $CR_6$ or N, wherein $R_6$ is selected from the group consisting of protium, deuterium, tritium, $C_1$-$C_{20}$ alkyl, $C_6$-$C_{30}$ aryl and $C_3$-$C_{30}$ hetero aryl.

In another aspect, the present disclosure provides an OLED that comprises a first electrode; a second electrode facing the first electrode; and at least one emitting unit disposed between the first and second electrodes, wherein the at least one emitting unit comprises the organic compound.

As an example, the organic compound may be included in an electron transport layer (ETL), a hole blocking layer (HBL), an emitting material layer (EML) and/or a charge generation layer (CGL) in the emitting unit.

For example, the organic compound may be comprised in the EML as a host, and the EML further comprises at least one dopant that is delayed fluorescent material, fluorescent material or phosphorescent material.

In still another aspect, the present disclosure provides an organic light emitting device that comprises a substrate and an OLED disposed over the substrate, as described above.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the disclosure, are incorporated in and constitute a part of this application, illustrate embodiments of the disclosure and together with the description serve to explain principles of the disclosure.

DETAILED DESCRIPTION

Figure 1:
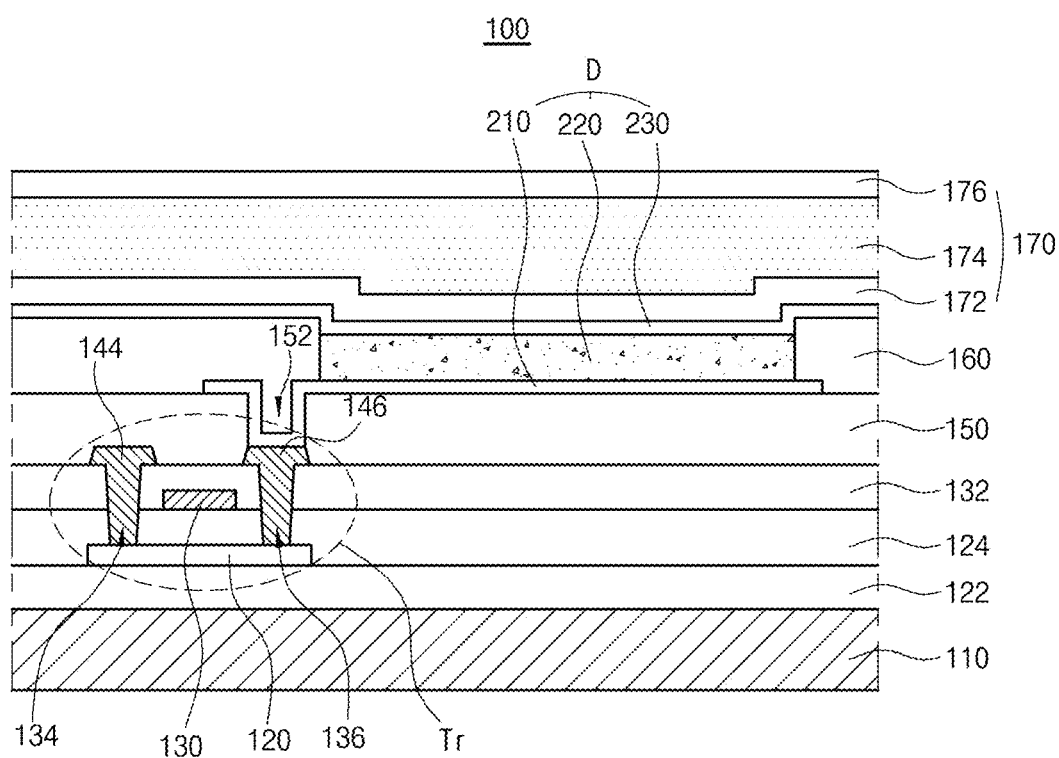
FIG. 1 is a schematic cross-sectional view illustrating an organic light emitting display device of the present disclosure.

Reference will now be made in detail to aspects of the disclosure, examples of which are illustrated in the accompanying drawings.

[Organic Compound]

An organic compound applied to an organic light emitting diode (OLED) should have excellent luminous properties, affinity to charges and maintain stable properties to in driving the OLED. Particularly, a luminous material applied to the diode is the most important factor determining the luminous efficiency of the OLED. The luminous material should have high quantum efficiency, large mobility for charges and adequate energy levels with regard to other materials applied in the same or adjacent layers. An organic compound in accordance with the present disclosure may have the following structure of Chemical Formula 1:

[Chemical Formula 1]

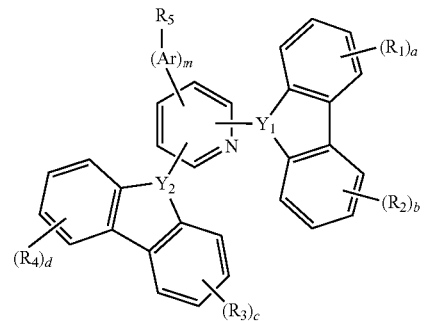

In Chemical Formula 1, each of $R_1$ to $R_4$ is independently selected from the group consisting of protium, deuterium, tritium, $C_1$-$C_{20}$ alkyl, $C_1$-$C_{20}$ alkoxy, $C_1$-$C_{20}$ alkyl amino, $C_6$-$C_{30}$ aryl, $C_3$-$C_{30}$ hetero aryl, $C_7$-$C_{30}$ aralkyl, $C_3$-$C_{30}$ hetero aralkyl, $C_6$-$C_{30}$ aryloxy, $C_3$-$C_{30}$ hetero aryloxy, $C_6$-$C_{30}$ aryl amino, $C_3$-$C_{30}$ hetero aryl amino and an adamantyl group, or when each of a to d is an integer of 2 or more, each of two adjacent $R_1$ groups, two adjacent $R_2$ groups, two adjacent $R_3$ groups and two adjacent $R_4$ groups independently forms an unsubstituted or substituted fused aromatic ring or an unsubstituted or substituted $C_3$-$C_{20}$ fused hetero aromatic ring; $R_5$ is selected from the group consisting of protium, deuterium, tritium, $C_1$-$C_{20}$ alkyl, $C_1$-$C_{20}$ alkoxy, $C_1$-$C_{20}$ alkyl amino, $C_6$-$C_{30}$ aryl, $C_3$-$C_{30}$ hetero aryl, $C_7$-$C_{30}$ aralkyl, $C_3$-$C_{30}$ hetero aralkyl, $C_6$-$C_{30}$ aryloxy, $C_3$-$C_{30}$ hetero aryloxy, $C_6$-$C_{30}$ aryl amino, $C_3$-$C_{30}$ hetero aryl amino and an adamantyl group, wherein at least one of $R_1$ to $R_5$ is the adamantyl group; each of a, b, c, d is the number of substituent and is independently an integer of 0 (zero) to 4; Ar is $C_6$-$C_{30}$ arylene or $C_3$-$C_3$ hetero arylene; m is an integer of 0 (zero) or 1; each of $Y_1$ and $Y_2$ is independently selected from the group consisting of $CR_6$ or N, wherein $R_6$ is selected from the group consisting of protium, deuterium, tritium, $C_1$-$C_{20}$ alkyl, $C_6$-$C_{30}$ aryl and $C_3$-$C_{30}$ hetero aryl.

As used the term "substituted" herein, the substitution group comprise, but is not limited to, deuterium, tritium, unsubstituted or halogen-substituted $C_1$-$C_{20}$ alkyl, unsubstituted or halogen-substituted $C_1$-$C_{20}$ alkoxy, halogen, cyano, —$CF_3$, a hydroxyl group, a carboxylic group, a carbonyl group, an amino group, a $C_1$-$C_{10}$ alkyl amino group, a $C_6$-$C_{30}$ aryl amino group, a $C_3$-$C_{30}$ hetero aryl group, a nitro group, a hydrazyl group, a sulfonate group, a $C_1$-$C_{20}$ alkyl silyl group, a $C_6$-$C_{30}$ aryl silyl group, a $C_3$-$C_{30}$ hetero aryl silyl group, a $C_6$-$C_{30}$ aryl group and a $C_3$-$C_{30}$ hetero aryl group.

As used herein, the term 'hetero" in such as "a hetero aromatic ring", "a hetero cycloalkyene group", "a hetero arylene group", "a hetero aryl alkylene group", "a hetero aryl oxylene group", "a hetero cycloalkyl group", "a hetero aryl group", "a hetero aryl alkyl group", "a hetero aryloxy group", "a hetero aryl amino group" means that at least one carbon atom, for example 1-5 carbons atoms, constituting an aromatic ring or an alicyclic ring is substituted with at least one hetero atom selected from the group consisting of N, O, S, P and combination thereof.

The organic compound having the structure of Chemical Formula 1 comprises a pyridine moiety having excellent affinity to electrons, a fused aromatic or fused hetero aromatic group connected to the pyridine moiety and having excellent affinity to holes, and at least one adamantyl moiety linked directly or indirectly to the pyridine moiety, the fused aromatic or fused hetero aromatic moiety. Since the pyridine moiety in the organic compound having the structure of Chemical Formula 1 has high affinity to electrons, the pyridine moiety may have n-type property that induces injection or transfer of electrons. Since the fused aromatic or fused hetero aromatic moiety has high affinity to holes, the fused aromatic or fused hetero aromatic moiety may have a p-type property that induces injection or transfer of holes. Accordingly, the organic compound having the structure of Chemical Formula 1 has a bipolar property.

As an example, the adamantyl group may have the following structure:

[Adamantyl Group]

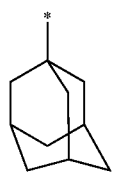

wherein the asterisk indicates a linkage site.

In one exemplary aspect, the $C_6$-$C_{30}$ aryl group constituting each of $R_1$ to $R_6$ in Chemical Formula 1 may be independently, but is not limited to, a unfused or fused aryl group such as phenyl, biphenyl, terphenyl, naphthyl, anthracenyl, pentalenyl, indenyl, indeno-indenyl, heptalenyl, biphenylenyl, indacenyl, phenalenyl, phenanthrenyl, benzo-phenanthrenyl, dibenzo-phenanthrenyl, azulenyl, pyrenyl, fluoranthenyl, triphenylenyl, chrysenyl, tetraphenylenyl, tetracenyl, pleiadenyl, picenyl, pentaphenylenyl, pentacenyl, fluorenyl, indeno-fluorenyl and spiro-fluorenyl.

In another exemplary aspect, the $C_3$-$C_{30}$ hetero aryl group constituting each of $R_1$ to $R_6$ in Chemical Formula 1 may be independently, but is not limited to, a unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzo-carbazolyl, dibenzo-carbazolyl, indolo-carbazolyl, indeno-carbazolyl, benzo-furo-carbazolyl, benzo-thieno-carbazolyl, carbolinyl, quinolinyl, iso-quinolinyl, phthlazinyl, quinoxalinyl, cinnolinyl, quinazolinyl, quinolizinyl, purinyl, benzo-quinolinyl, benzo-iso-quinolinyl, benzo-quinazolinyl, benzo-quinoxalinyl, acridinyl, phenazinyl, phenoxazinyl, phenothiazinyl, phenanthrolinyl, perimidinyl, phenanthridinyl, pteridinyl, naphthyridinyl, furanyl, pyranyl, oxazinyl, oxazolyl, oxadiazolyl, triazolyl, dioxinyl, benzo-furanyl, dibenzo-furanyl, thiopyranyl, xanthenyl, chromenyl, iso-chromenyl, thioazinyl, thiophenyl, benzo-thiophenyl, dibenzo-thiophenyl, difuro-pyrazinyl, benzofuro-dibenzo-furanyl, benzothieno-benzo-thiophenyl, benzothieno-dibenzo-thiophenyl, benzo-thieno-benzo-furanyl, benzothieno-dibenzo-furanyl and N-substituted spiro fluorenyl.

As an example, the aromatic group or the hetero aromatic group constituting each of $R_1$ to $R_6$ may have one to three aromatic or hetero aromatic rings. When the number of the aromatic or the hetero aromatic ring constituting each of $R_1$ to $R_6$ becomes large, the conjugated structure within the whole molecule is too long, and therefore the organic compound may have excessively reduced energy bandgap. As an example, the aryl or the hetero aryl group constituting each of $R_1$ to $R_6$ may comprise independently, but is not limited to, phenyl, biphenyl, naphthyl, anthracenyl, pyrrolyl, triazinyl, furanyl, benzo-furanyl, dibenzo-furanyl, thiophenyl, benzo-thiophenyl, dibenzo-thiophenyl, carbazolyl, acridinyl, carbolinyl, phenazinyl, phenoxazinyl and/or phenothiazinyl.

In one alternative aspect, each of two adjacent $R_1$, two adjacent $R_2$, two adjacent $R_3$, and two adjacent $R_4$ may independently form a fused aromatic ring or a $C_3$-$C_{20}$ fused hetero aromatic ring. For example, the fused aromatic ring or the fused hetero aromatic ring may be unsubstituted or substituted with at least one group selected from $C_1$-$C_{10}$ alkyl; a $C_6$-$C_{20}$ aromatic group such as $C_6$-$C_{30}$ aryl, $C_7$-$C_{30}$ aralkyl, $C_6$-$C_{30}$ aryloxy and $C_6$-$C_{30}$ aryl amino; and a $C_3$-$C_{20}$ hetero aromatic group such as $C_3$-$C_{30}$ hetero aryl, $C_4$-$C_{30}$ hetero aralkyl, $C_3$-$C_{30}$ hetero aryloxy and $C_3$-$C_{30}$ hetero aryl amino.

In this case, other aromatic or hetero aromatic ring fused to the fused aromatic or hetero aromatic moiety (moiety including $Y_1$ or $Y_2$) having the p-type property may be, but is not limited to, a fused aromatic ring such as a benzene ring, a naphthalene ring and/or a indeno ring, or a hetero aromatic ring such as a benzo-furo ring, a benzo-thieno ring and an indolo ring. For example, the fused aromatic or the hetero aromatic ring having the p-type property may be fused with other aromatic or hetero aromatic ring to form, but is not limited to, benzo-fluorenyl, benzo-carbazolyl, dibenzo-fluorenyl, dibenzo-carbazolyl, indeno-fluorenyl, indeno-carbazolyl, benzo-furo-fluorenyl, benzo-furo-carbazolyl, benzo-thieno-fluorenyl, benzo-thieno-carbazolyl, indolo-fluorenyl and indolo-carbazolyl.

As an example, the $C_6$-$C_{20}$ aromatic group or the $C_3$-$C_{20}$ hetero aromatic group that can be fused to the fused aromatic or the fused hetero aromatic moiety having the p-type property may be $C_6$-$C_{20}$ aryl or $C_3$-$C_{20}$ hetero aryl. In this case, the $C_6$-$C_{20}$ aryl or $C_3$-$C_{20}$ hetero aryl may be independently selected from the aryl or the hetero aryl that constitute each of $R_1$ to $R_6$.

In one exemplary aspect, when the number of the aromatic or the hetero aromatic ring constituting the Ar become large, the conjugated structure within the whole molecule is too long, and therefore the organic compound may have excessively reduced energy bandgap. Accordingly, the Ar may have one to three aromatic or hetero aromatic rings, preferably one or two aromatic or hetero aromatic rings. With regard charge injection and transfer, the Ar may comprise 5-membered to 7-membered rings, and particularly a 6-membered ring. For example, the Ar may comprise, but is not limited to, phenylene, biphenylene, naphthylene, anthracenylene, pyrrolylene, imidazolylene, pyrazolylene, pyridinylene, pyrazinlylene, pyrimidinylene, pyridazinlylene, furanylene and thiophenylene.

As described above, the organic compound is a bipolar compound having the structure of Chemical Formula 1, which comprises the pyridine moiety having the n-type property, and the fused aromatic or fused hetero aromatic moiety having the p-type property. Also, the organic compound comprises at least one adamantyl group that is bulky and prevents the molecule from rotating and transformation, so that the organic compound has excellent thermal stability, high excited singlet and triplet energy levels.

When the organic compound is introduced into an emissive layer, such as an EML of an OLED, electrons and holes can be injected into the EML in balance and the recombination zone among the holes and electrons are located uniformly on the whole EML area, so that the OLED can maximize its luminous efficiency.

In addition, the organic compound having the structure of Chemical Formula 1 has wide bandgap between the HOMO (Highest Occupied Molecular Orbital) energy level and the LUMO (Lowest Unoccupied Molecular Orbital) energy level and high excited triplet energy level, thus it may be used as a host of the EML. When the organic compound is used as the host in the EML, exciton energies of the host can be transferred efficiently to dopants, and exciton quenching caused by the interactions between the triplet/singlet excitons of the host or the dopants and adjacent hole (or electron)-polarons can be minimized.

Moreover, since the organic compound having the structure of Chemical Formula 1 has an excellent thermal stability, it is not decomposed easily by Joule's heat generating in driving the OLED. In other words, since the molecular structure of the organic compound having the structure of Chemical Formula 1 and its function is not destroyed or deteriorated by heat, when the organic compound is introduced in the emissive layer, the OLED can enhance its luminous lifetime. For example, when the organic compound having the structure of Chemical Formula 1 may be used together with fluorescent material, delayed fluorescent material in the EML, the driving voltage and the power consumption of the OLED can be reduced. As the stress resulted from the raise of the driving voltage decreases, the OLED can enhance its luminous efficiency and increase its luminous lifetime.

Further, since the organic compound having the structure of Chemical Formula 1 has high affinity to electrons and low HOMO energy level, it can be applied into any one of the ETL, HBL in the emitting unit, or N-CGL disposed between plural emitting units.

For example, the organic compound having the structure of Chemical Formula 1 may have an excited triplet energy level, but is not limited to, equal to or more than about 2.70 eV, preferably about 2.85 eV. In addition, the organic compound may have, but is not limited to, a HOMO energy level between about −5.5 eV and about −6.3 eV, preferably about −5.7 eV and about −6.0 eV, a LUMO energy level between about −2.0 eV and about −3.0 eV, preferably about −2.1 eV and about −2.5 eV, and an energy bandgap (Eg) between the HOMO energy level and the LUMO energy level between about 3.0 eV about 4.0 eV, preferably about 3.3 eV and 3.8 eV.

The organic compound having the structure of Chemical Formula 1 may comprise an organic compound in which one or two of the $R_1$ to $R_5$ is the adamantyl group, and others of the $R_1$ to $R_5$ are independently selected from the group consisting of protium, deuterium, tritium, $C_1$-$C_{10}$ alkyl and $C_{10}$-$C_{30}$ fused hetero aryl. Alternatively, each of the $Y_1$ and $Y_2$ may be independently N, and Ar may be arylene selected from the group consisting of phenylene, naphthylene and anthracenylene. In this case, the $C_{10}$-$C_{30}$ fused hetero aryl may be selected from, but is not limited to, the group consisting of carbazolyl, acridinyl, dibenzo-furanyl, dibenzo-thiophenyl, phenazinyl and phenoxazinyl.

In one exemplary aspect, the organic compound may have an organic compound in which one of the $R_1$ to $R_5$ is the adamantyl group and others of the $R_1$ to $R_5$ are independently is protium, deuterium, tritium or the aliphatic group, respectively, and each of $Y_1$ and $Y_2$ is independently N. For example, such an organic compound may comprise anyone having the following structure of Chemical Formula 2:

[Chemical Formula 2]

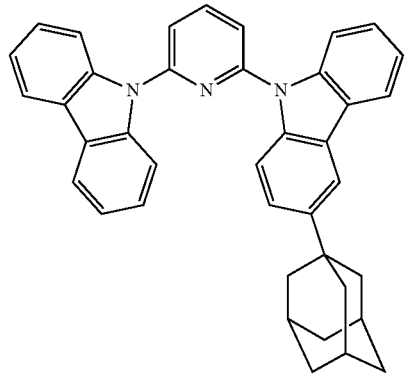

1-1

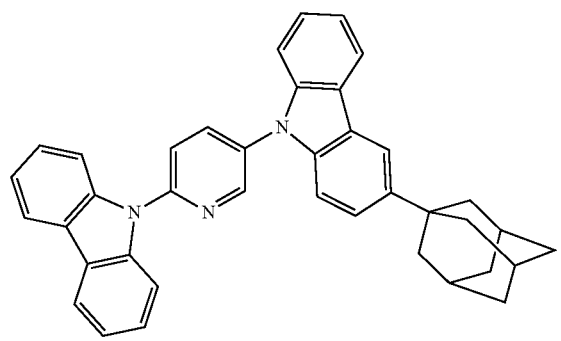

1-2

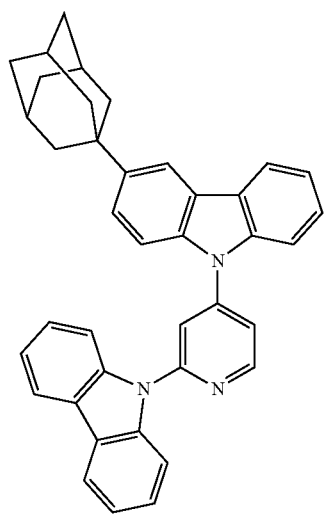

1-3

1-4
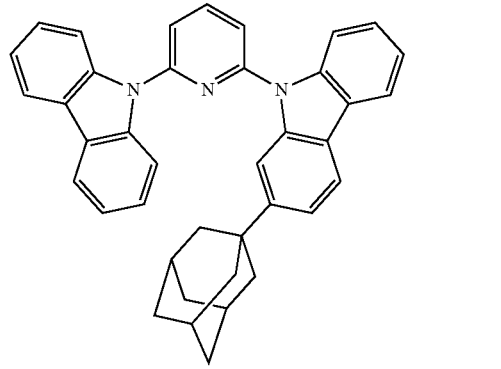
1-5
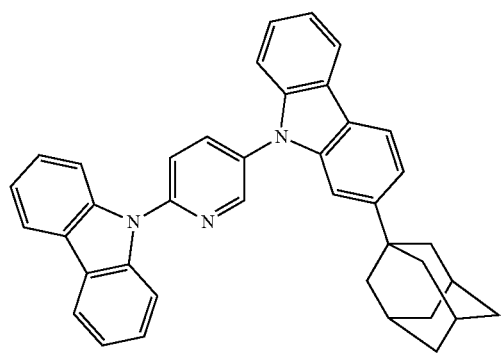
1-6
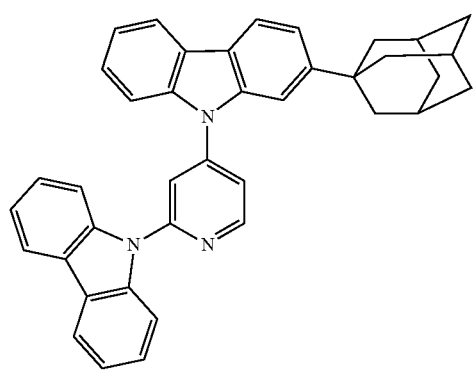
1-7
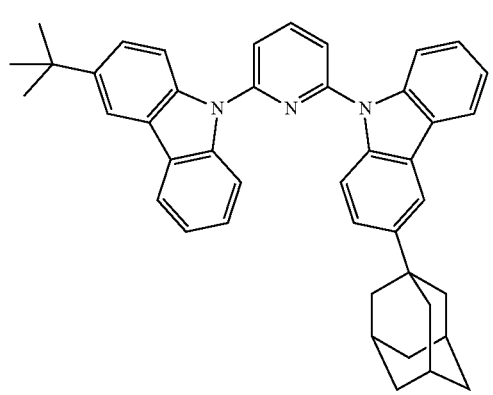
1-8
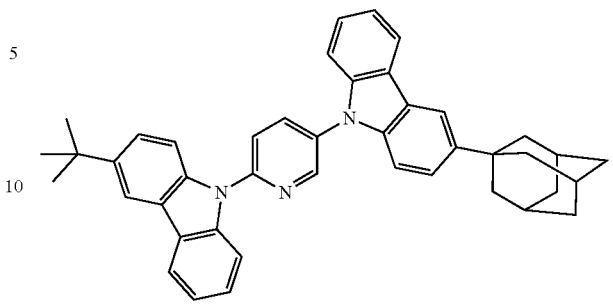
1-9
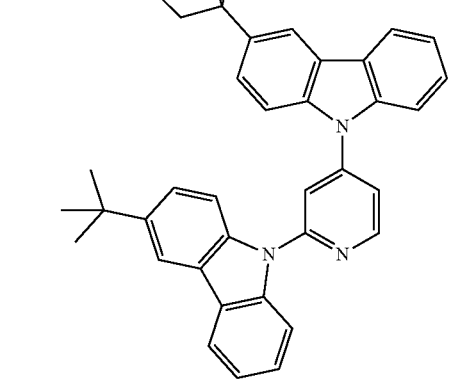
1-10
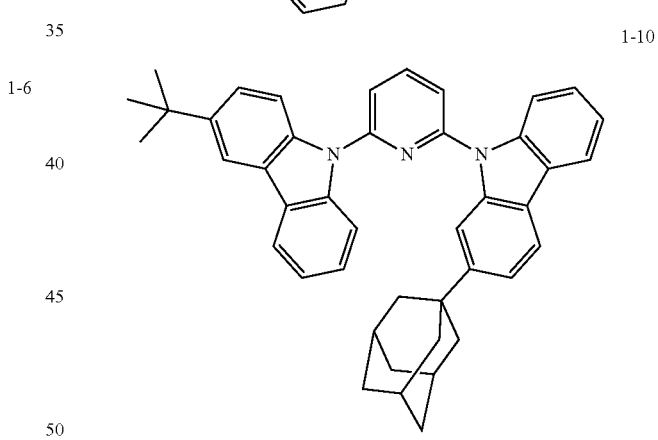
1-11
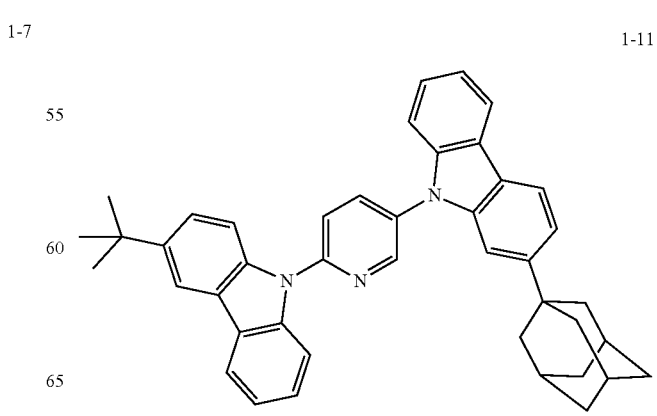

1-12
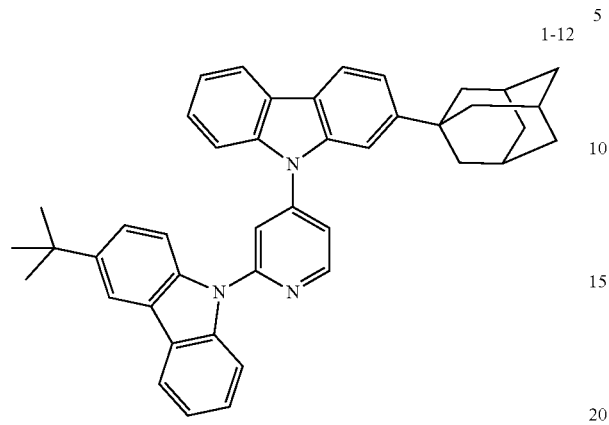
1-15
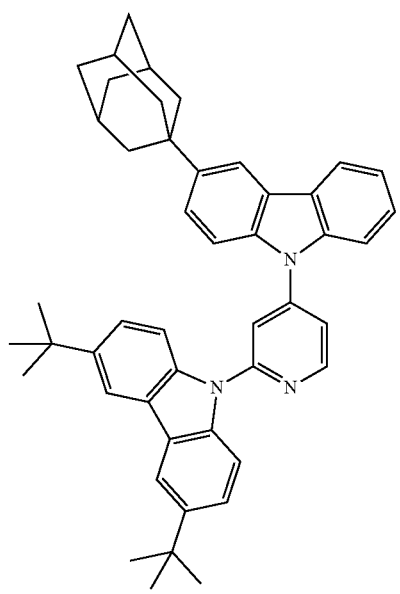
1-13
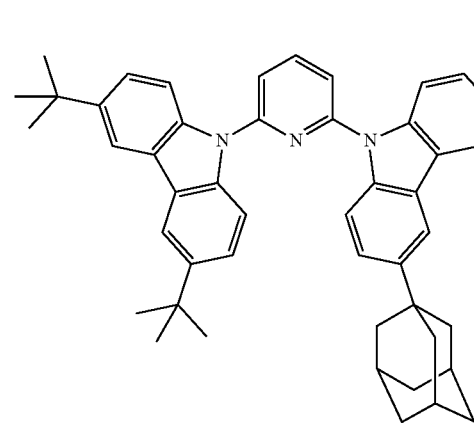
1-16
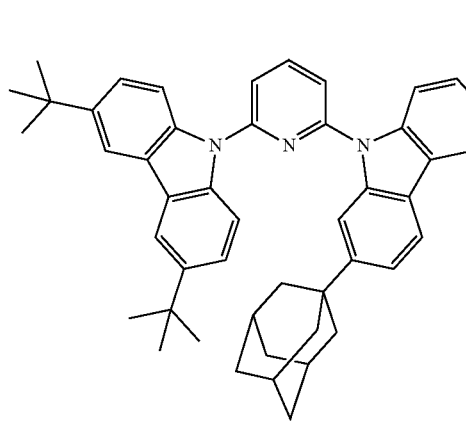
1-14
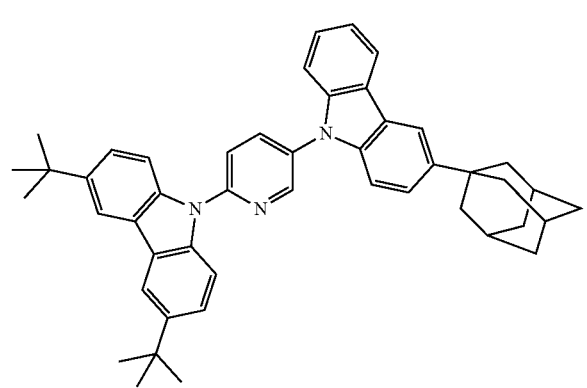
1-17
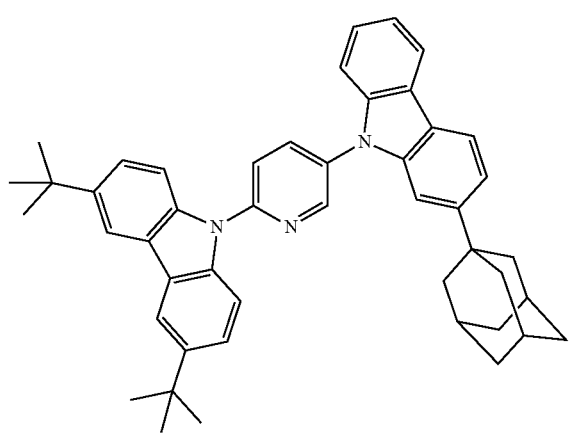

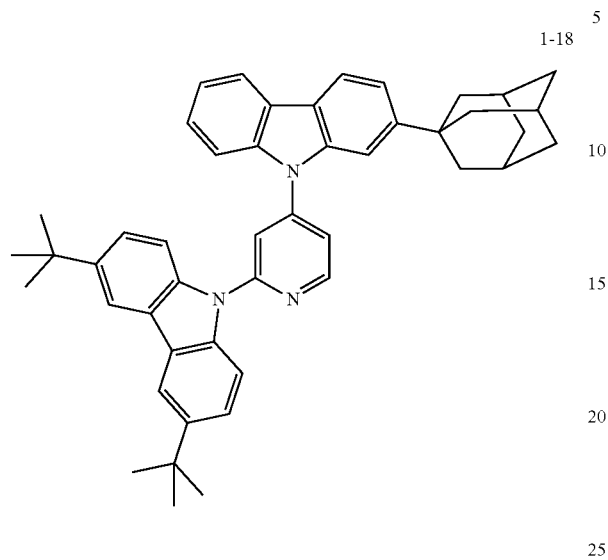
1-18
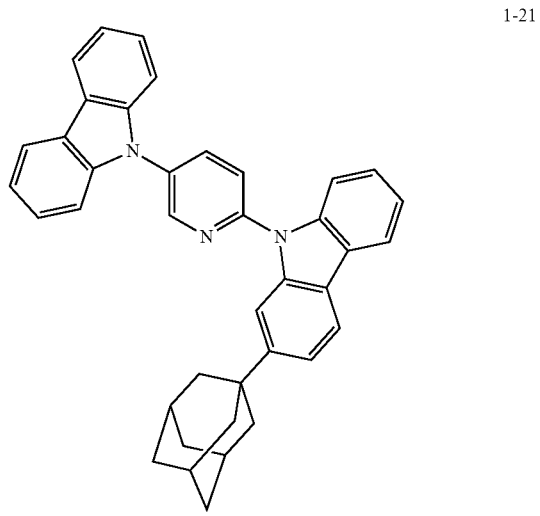
1-21
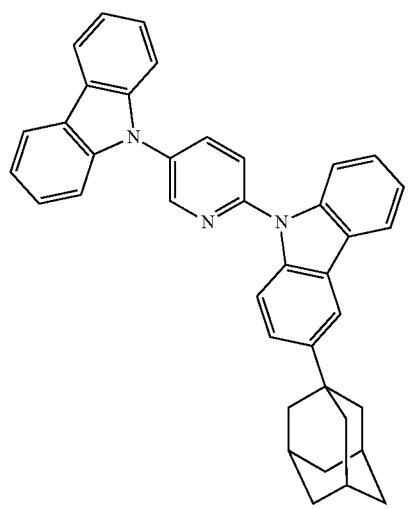
1-19
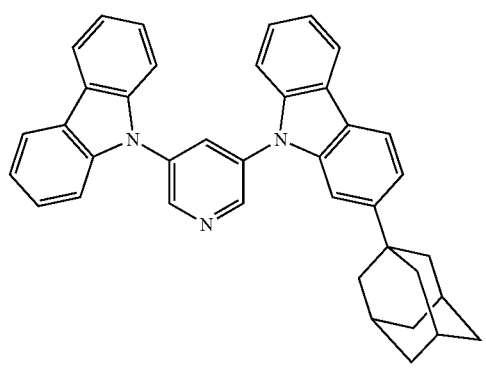
1-22
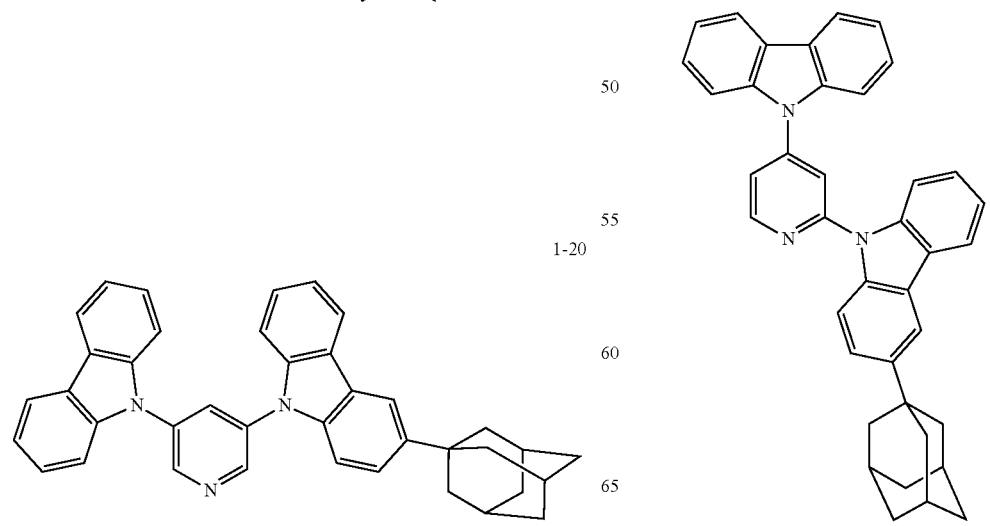
1-20
1-23

1-24
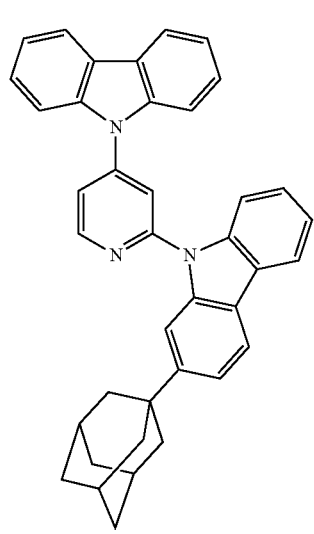
1-25
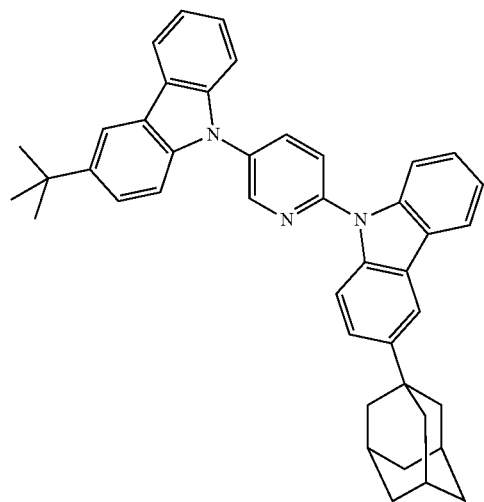
1-26
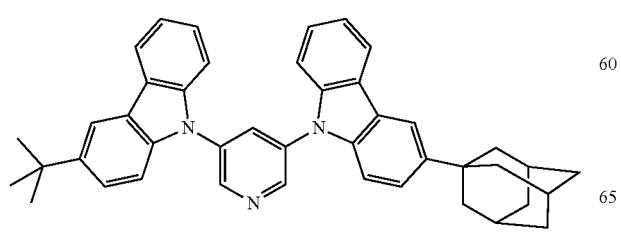
1-27
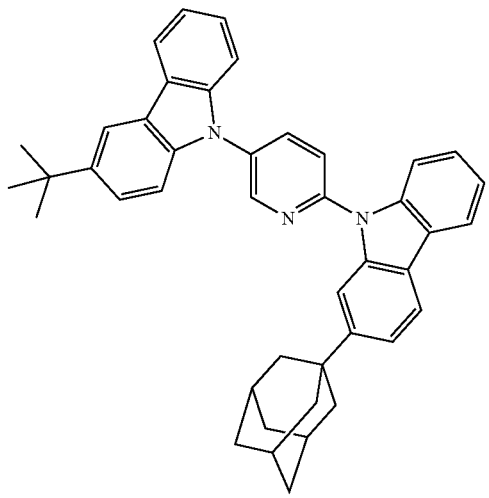
1-28
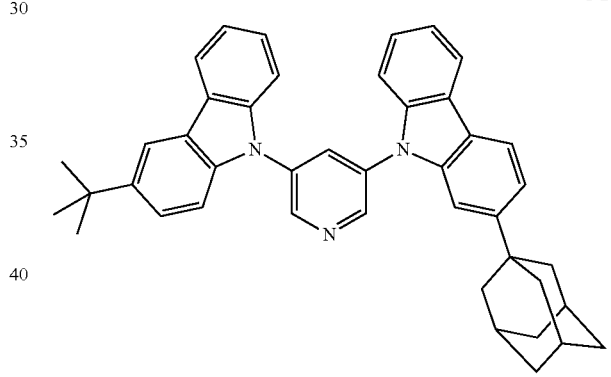
1-29
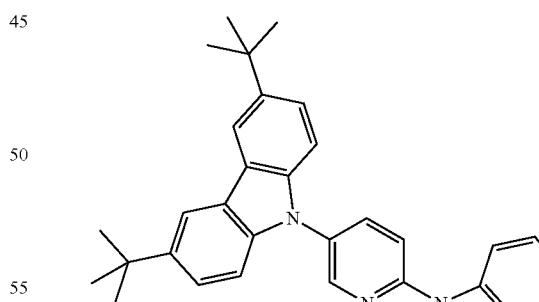

1-30
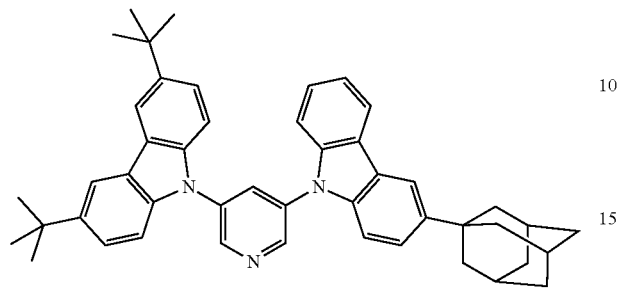
1-31
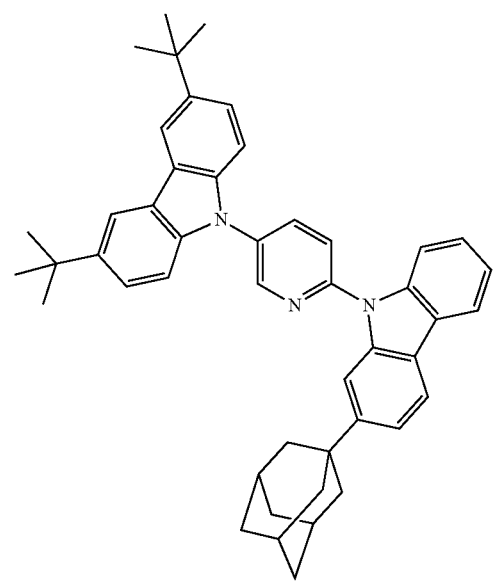
1-32
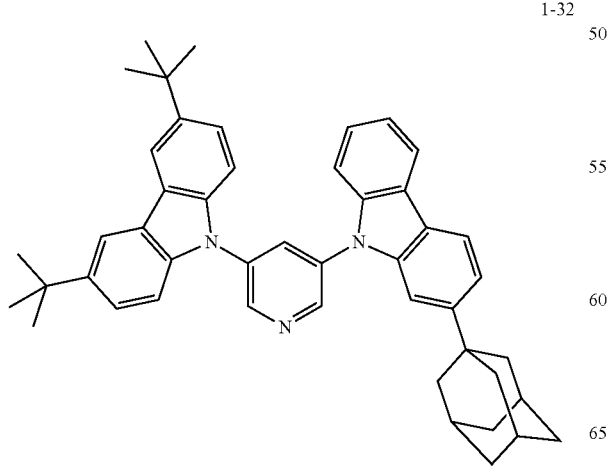
1-33
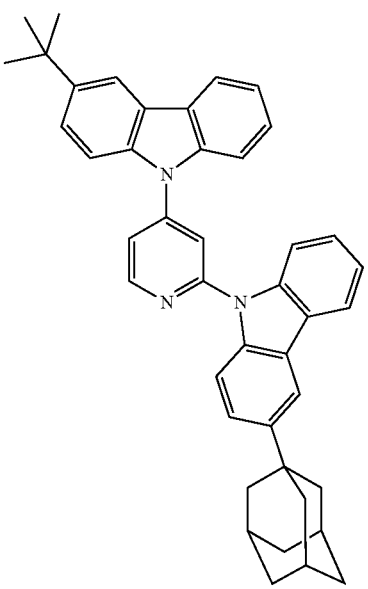
1-34
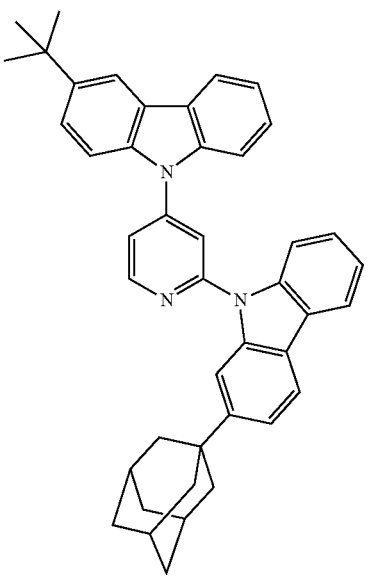

-continued 1-35
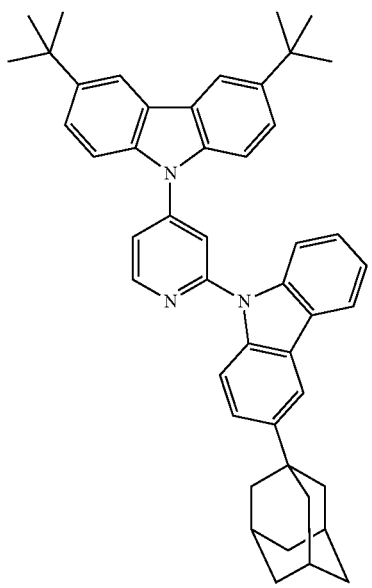

1-36
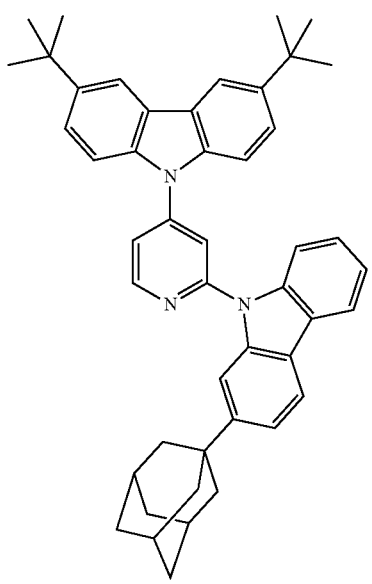

1-37
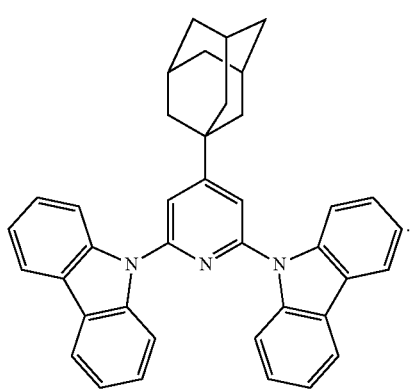

In another exemplary aspect, the organic compound having the structure of Chemical Formula 1 may comprise an organic compound in which two of the $R_1$ to $R_5$ are the adamantyl group and other of the $R_1$ to $R_5$ are independently protium, deuterium, tritium or the aliphatic group, respectively, and each of $Y_1$ and $Y_2$ is independently N. For example, such an organic compound may comprise anyone having the following structure of Chemical Formula 3:

[Chemical Formula 3]

2-1
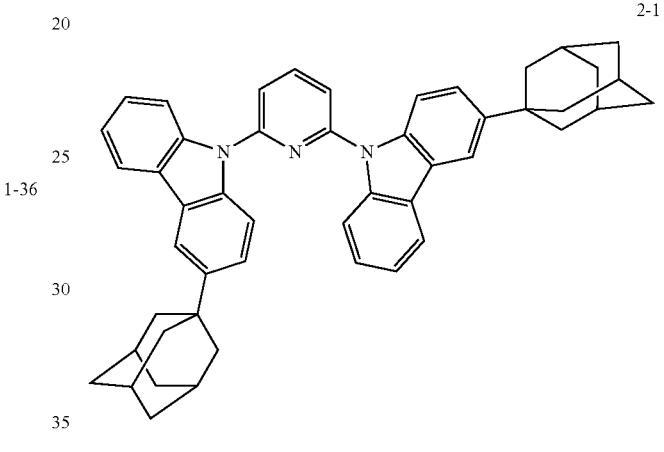

2-2
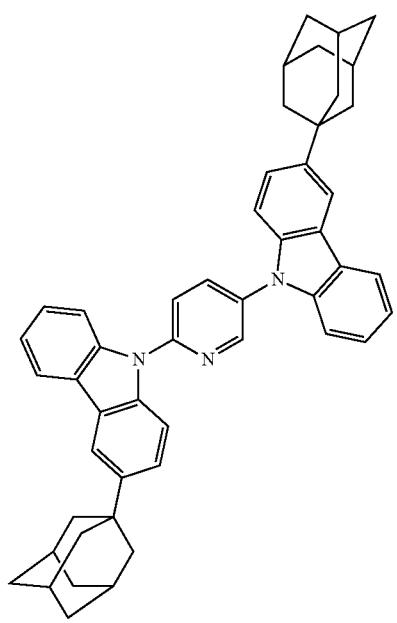

2-3

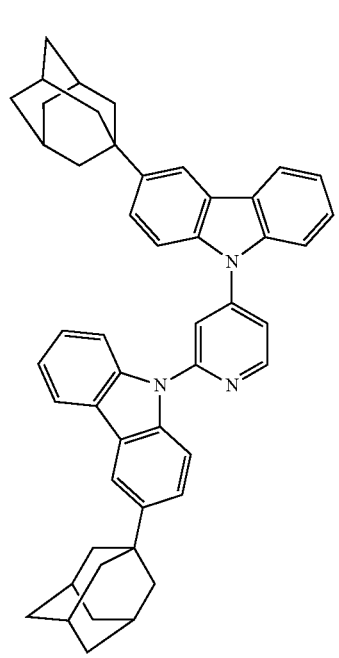

2-4

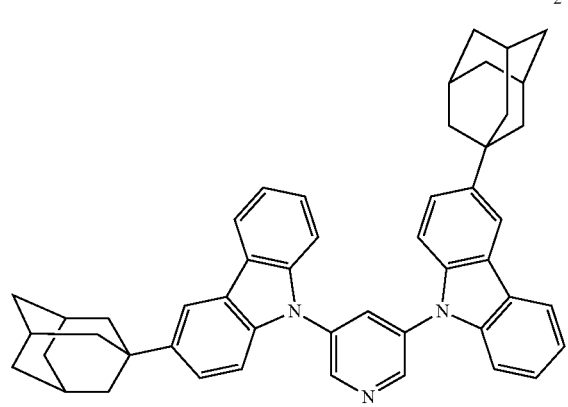

2-5

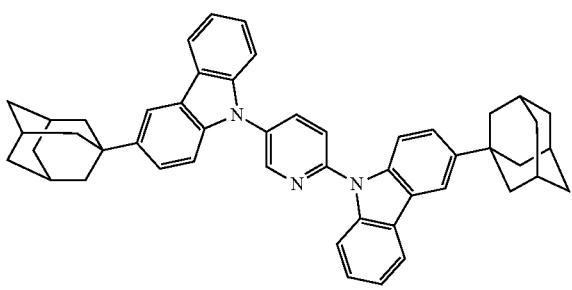

2-6

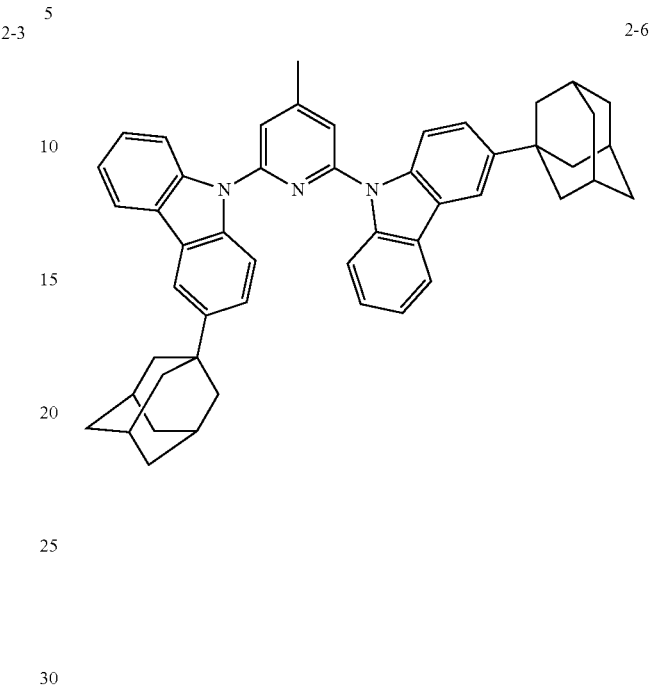

2-7

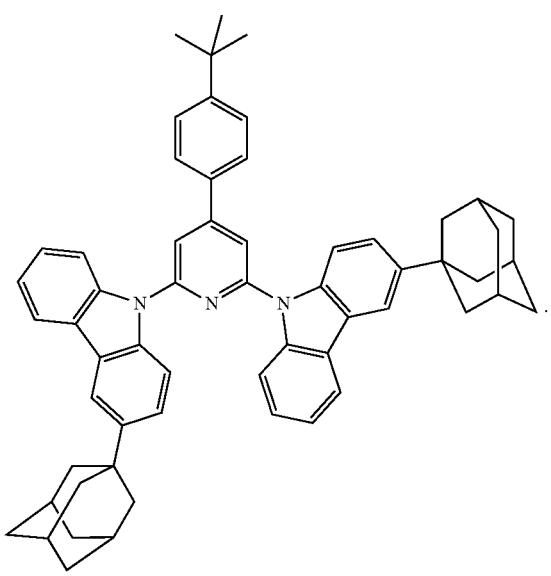

In still another exemplary aspect, the organic compound having the structure of Chemical Formula 1 may comprise an organic compound in which one of the $R_1$ to $R_5$ is the adamantyl group, each of $Y_1$ and $Y_2$ is independently N, and at least one aromatic or hetero aromatic group is linked to the fused hetero aromatic moiety having the p-type property. For example, such an organic compound may comprise anyone having the following structure of Chemical Formula 4.

[Chemical Formula 4]
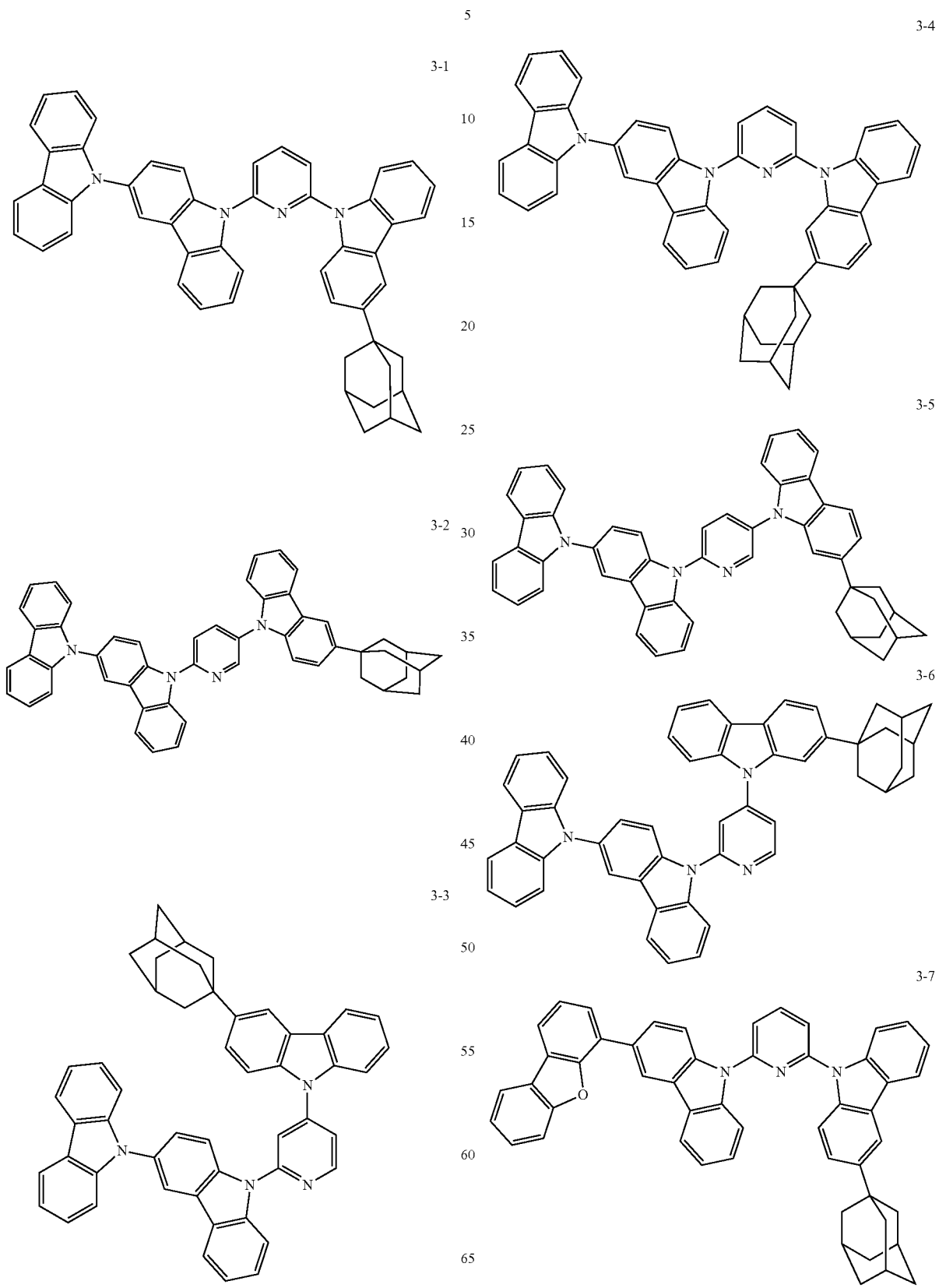

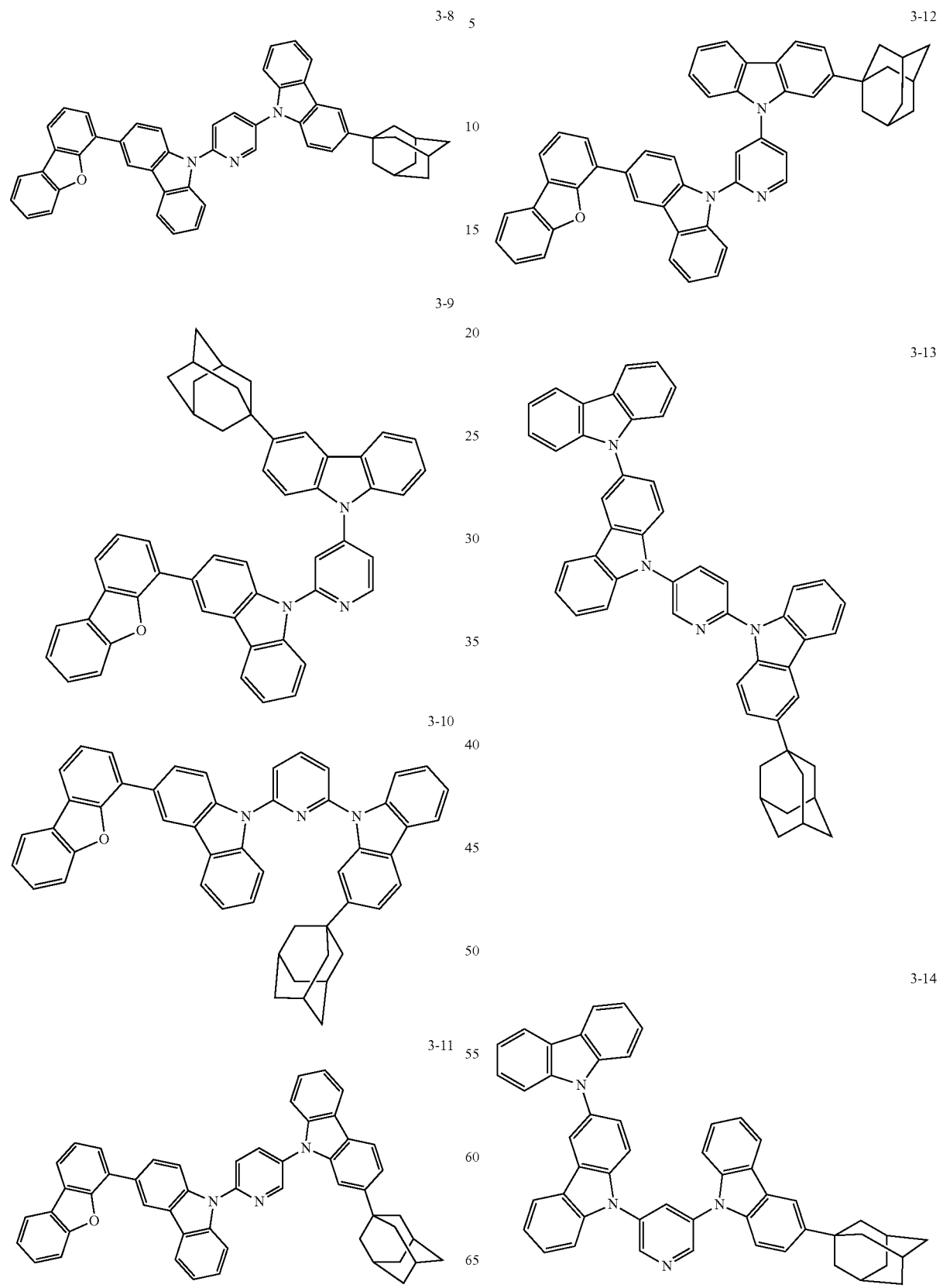

3-15
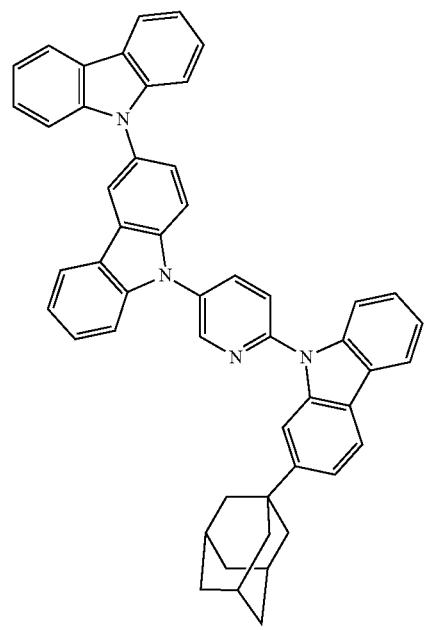
3-16
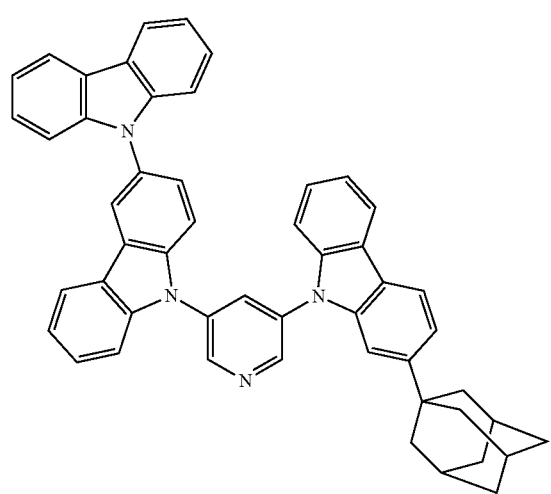
3-17
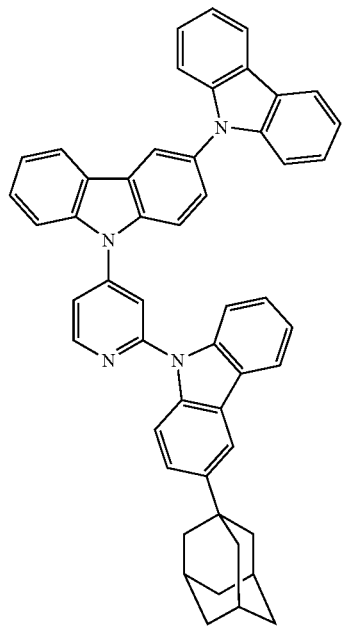
3-18
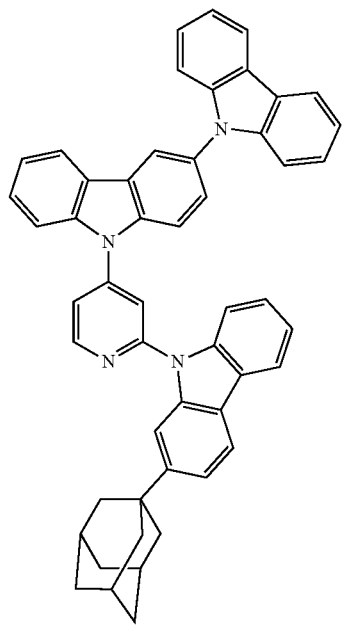

3-19
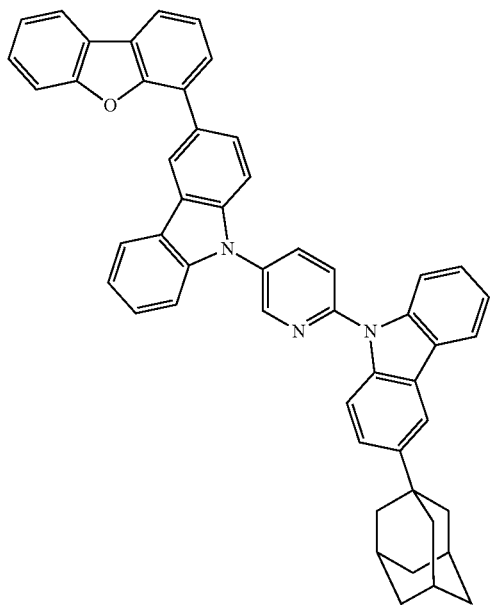
3-22
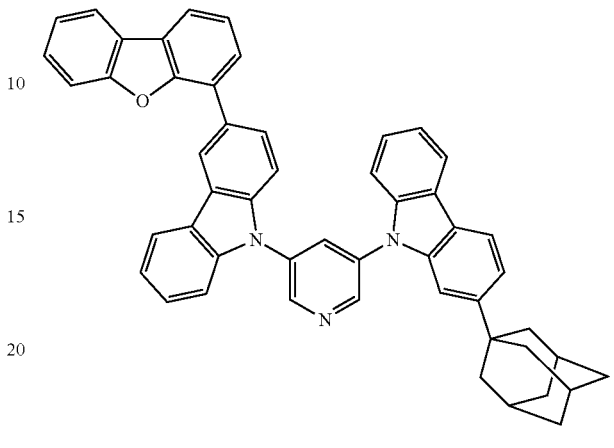
3-20
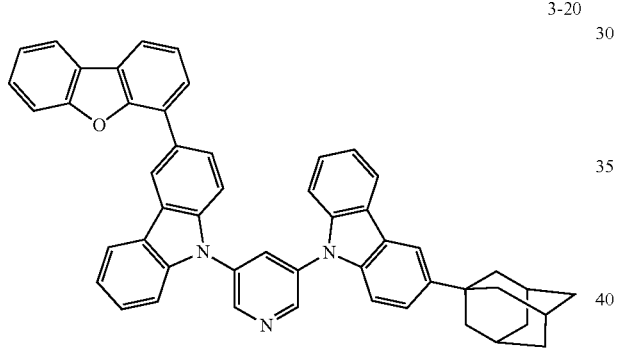
3-21
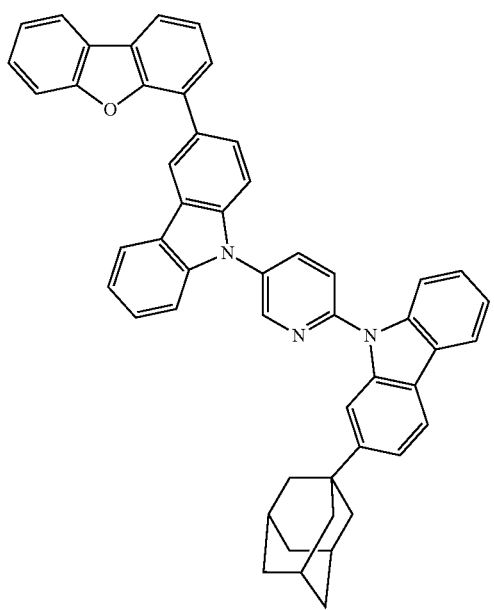
3-23
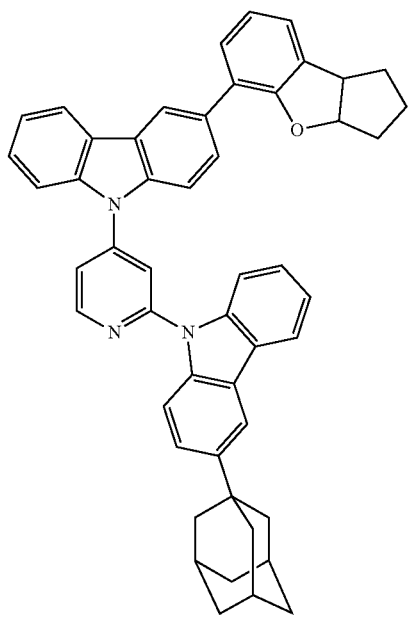

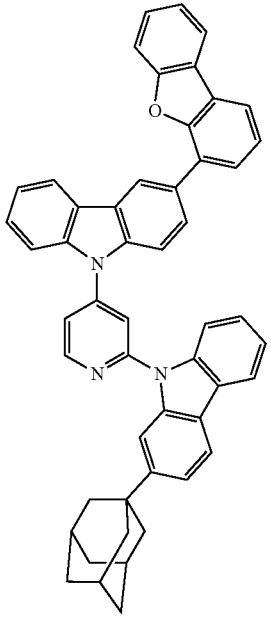

3-24

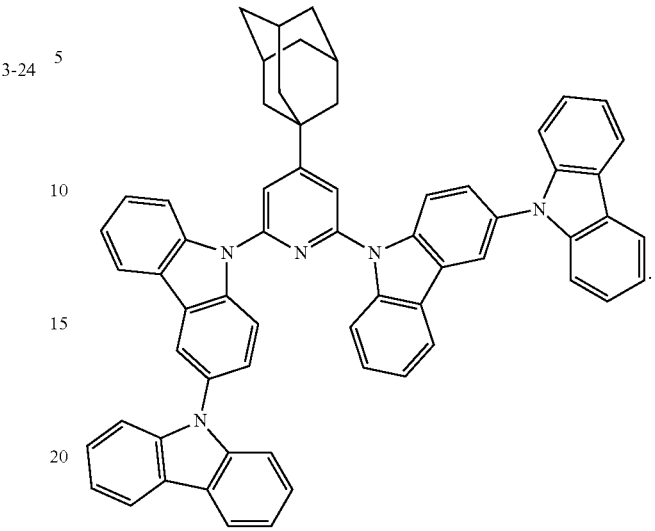

3-25

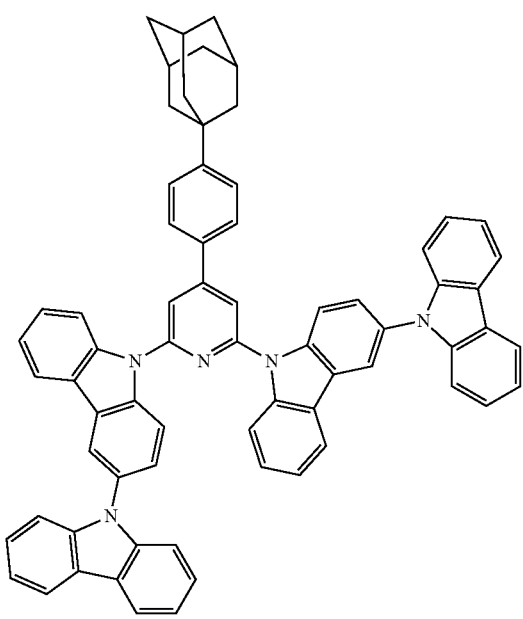

3-26

Any compound having the structures of Chemical Formulae 2 to 4 has both the n-type property and the p-type property. Since the organic compound comprises at least one adamantyl group, it shows excellent thermal stability, has a high excited triplet energy level and wide energy bandgap between the HOMO and LUMO energy levels. When the organic compound is introduced into any one of the EML, ETL, HBL and/or N-CGL of the OLED, the OLED can lower its driving voltage and enhance its luminous efficiency and luminous lifetime. As an example, when any compound having the structure of Chemical Formulae 2 to 4 is used together with dopants, exciton energies can be transferred to dopants during the luminescence process.

[Organic Light Emitting Device and OLED]

The organic compound having the structure of Chemical Formulae 1 to 4 has excellent thermal property, luminous efficiency and luminous lifetime. When any compound having the structure of Chemical Formulae 1 to 4 is introduced into an emissive layer, it is possible to implement an OLED having enhanced luminous efficiency and improved luminous lifetime. The OLED of the present disclosure may be applied to an organic light emitting device such as an organic light emitting display device or an organic light emitting illumination device. An organic light emitting display device including the OLED will be explained. FIG. 1 is a schematic cross-sectional view of an organic light emitting display device of the present disclosure.

As illustrated in FIG. 1, the organic light emitting display device 100 includes a substrate 110, a thin-film transistor Tr on the substrate 110, and an organic light emitting diode (OLED) D connected to the thin film transistor Tr.

The substrate 110 may include, but is not limited to, glass, thin flexible material and/or polymer plastics. For example, the flexible material may be selected from the group, but is not limited to, polyimide (PI), polyethersulfone (PES), polyethylenenaphthalate (PEN), polyethylene terephthalate (PET), polycarbonate (PC) and combination thereof. The substrate 110, over which the thin film transistor Tr and the OLED D are arranged, form an array substrate.

A buffer layer 122 may be disposed over the substrate 110, and the thin film transistor Tr is disposed over the buffer layer 122. The buffer layer 122 may be omitted.

A semiconductor layer 120 is disposed over the buffer layer 122. In one exemplary aspect, the semiconductor layer 120 may include, but is not limited to, oxide semiconductor materials. In this case, a light-shield pattern may be disposed under the semiconductor layer 120, and the light-shield pattern can prevent light from being incident toward the semiconductor layer 120, and thereby, preventing the semiconductor layer 120 from being deteriorated by the light. Alternatively, the semiconductor layer 120 may include, but is not limited to, polycrystalline silicon. In this case, opposite edges of the semiconductor layer 120 may be doped with impurities.

A gate insulating layer 124 formed of an insulating material is disposed on the semiconductor layer 120. The gate insulating layer 124 may include, but is not limited to, an inorganic insulating material such as silicon oxide ($SiO_x$) or silicon nitride ($SiN_x$).

A gate electrode 130 made of a conductive material such as a metal is disposed over the gate insulating layer 124 so as to correspond to a center of the semiconductor layer 120. While the gate insulating layer 124 is disposed over a whole area of the substrate 110 in FIG. 1, the gate insulating layer 124 may be patterned identically as the gate electrode 130.

An interlayer insulating layer 132 formed of an insulating material is disposed on the gate electrode 130 with covering over an entire surface of the substrate 110. The interlayer insulating layer 132 may include, but is not limited to, an inorganic insulating material such as silicon oxide ($SiO_x$) or silicon nitride ($SiN_x$), or an organic insulating material such as benzocyclobutene or photo-acryl.

The interlayer insulating layer 132 has first and second semiconductor layer contact holes 134 and 136 that expose both sides of the semiconductor layer 120. The first and second semiconductor layer contact holes 134 and 136 are disposed over opposite sides of the gate electrode 130 with spacing apart from the gate electrode 130. The first and second semiconductor layer contact holes 134 and 136 are formed within the gate insulating layer 124 in FIG. 1. Alternatively, the first and second semiconductor layer contact holes 134 and 136 are formed only within the interlayer insulating layer 132 when the gate insulating layer 124 is patterned identically as the gate electrode 130.

A source electrode 144 and a drain electrode 146, which are formed of conductive material such as a metal, are disposed on the interlayer insulating layer 132. The source electrode 144 and the drain electrode 146 are spaced apart from each other with respect to the gate electrode 130, and contact both sides of the semiconductor layer 120 through the first and second semiconductor layer contact holes 134 and 136, respectively.

The semiconductor layer 120, the gate electrode 130, the source electrode 144 and the drain electrode 146 constitute the thin film transistor Tr, which acts as a driving element. The thin film transistor Tr in FIG. 1 has a coplanar structure in which the gate electrode 130, the source electrode 144 and the drain electrode 146 are disposed over the semiconductor layer 120. Alternatively, the thin film transistor Tr may have an inverted staggered structure in which a gate electrode is disposed under a semiconductor layer and a source and drain electrodes are disposed over the semiconductor layer. In this case, the semiconductor layer may comprise amorphous silicon.

A gate line and a data line, which cross each other to define a pixel region, and a switching element, which is connected to the gate line and the data line, may be further formed in the pixel region of FIG. 1. The switching element is connected to the thin film transistor Tr, which is a driving element. Besides, a power line is spaced apart in parallel from the gate line or the data line, and the thin film transistor Tr may further include a storage capacitor configured to constantly keep a voltage of the gate electrode for one frame.

In addition, the organic light emitting display device 100 may include a color filter that comprises dyes or pigments for transmitting specific wavelength light of light emitted from the OLED D. For example, the color filter can transmit light of specific wavelength such as red (R), green (G), blue (B) and/or white (W). Each of red, green, and blue color filter may be formed separately in each pixel region. In this case, the organic light emitting display device 100 can implement full-color through the color filter.

For example, when the organic light emitting display device 100 is a bottom-emission type, the color filter may be disposed on the interlayer insulating layer 132 with corresponding to the OLED D. Alternatively, when the organic light emitting display device 100 is a top-emission type, the color filter may be disposed over the OLED D, that is, a second electrode 230.

A passivation layer 150 is disposed on the source and drain electrodes 144 and 146 over the whole substrate 110. The passivation layer 150 has a flat top surface and a drain contact hole 152 that exposes the drain electrode 146 of the thin film transistor Tr. While the drain contact hole 152 is disposed on the second semiconductor layer contact hole 136, it may be spaced apart from the second semiconductor layer contact hole 136.

The OLED D includes a first electrode 210 that is disposed on the passivation layer 150 and connected to the drain electrode 146 of the thin film transistor Tr. The OLED D further includes an emissive layer 220 and a second electrode 230 each of which is disposed sequentially on the first electrode 210.

The first electrode 210 is disposed in each pixel region. The first electrode 210 may be an anode and include a conductive material having a relatively high work function value. For example, the first electrode 210 may include, but is not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

In one exemplary aspect, when the organic light emitting display device 100 is a top-emission type, a reflective electrode or a reflective layer may be disposed under the first electrode 210. For example, the reflective electrode or the reflective layer may include, but are not limited to, aluminum-palladium-copper (APC) alloy.

In addition, a bank layer 160 is disposed on the passivation layer 150 in order to cover edges of the first electrode 210. The bank layer 160 exposes a center of the first electrode 210.

An emissive layer 220 is disposed on the first electrode 210. In one exemplary aspect, the emissive layer 220 may have a mono-layered structure of an emitting material layer (EML). Alternatively, the emissive layer 220 may have a multiple-layered structure of a hole injection layer (HIL), a hole transport layer (HTL), an electron blocking layer (EBL), an EML, a hole blocking layer (HBL), an electron transport layer (ETL) and/or an electron injection layer (EIL) (see, FIGS. 2, 5, 7, 9 and 11). In one aspect, the emissive layer 220 may have single emitting unit. Alternatively, the emissive layer 220 may have multiple emitting units to form a tandem structure.

The emissive layer 220 comprises any compound having the structure of Chemical Formulae 1 to 4. As an example, the organic compound having the structure of Chemical Formulae 1 to 4 may be applied into a host in the EML, ETL, HBL and/or N-CGL.

The second electrode 230 is disposed over the substrate 110 above which the emissive layer 220 is disposed. The second electrode 230 may be disposed over a whole display area and may include a conductive material with a relatively low work function value compared to the first electrode 210. The second electrode 230 may be a cathode. For example, the second electrode 230 may include, but is not limited to, aluminum (Al), magnesium (Mg), calcium (Ca), silver (Ag), alloy thereof or combination thereof such as aluminum-magnesium alloy (Al—Mg).

In addition, an encapsulation film 170 may be disposed over the second electrode 230 in order to prevent outer moisture from penetrating into the OLED D. The encapsulation film 170 may have, but is not limited to, a laminated structure of a first inorganic insulating film 172, an organic insulating film 174 and a second inorganic insulating film 176.

Moreover, a polarizer may be attached to the encapsulation film 170 in order to decrease external light reflection. For example, the polarizer may be a circular polarizer. In addition, a cover window may be attached to the encapsulation film 170 or the polarizer. In this case, the substrate 110 and the cover window may have a flexible property, thus the organic light emitting display device 100 may be a flexible display device.

As described above, the OLED D comprises any compound having the structure of Chemical Formulae 1 to 4 in the emissive layer 220 and the CGL. Since such an organic compound has excellent thermal stability and luminous properties, applying the organic compound into the emissive layer allows the OLED D to improve its luminous efficiency and luminous lifetime and to lower its driving voltage and power consumption.

Figure 2:
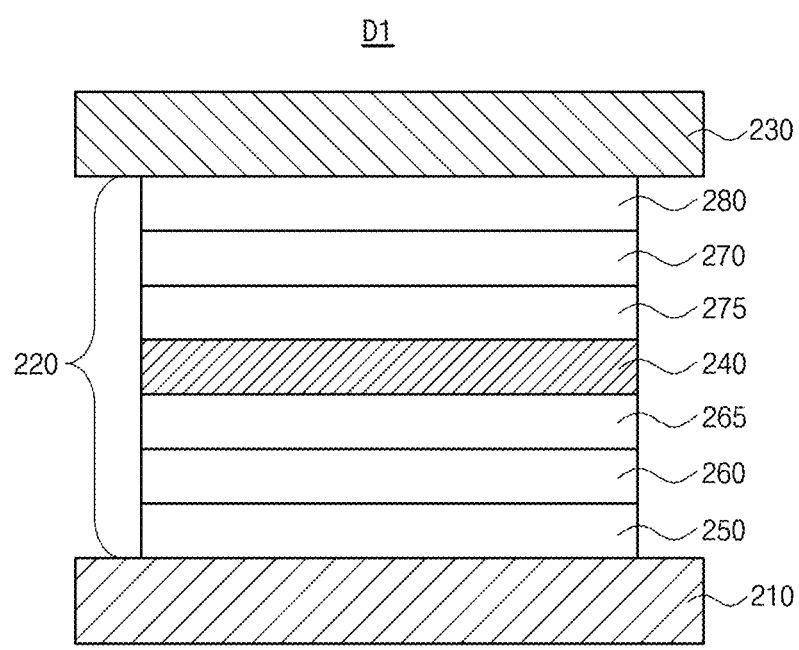
FIG. 2 is a schematic cross-sectional view illustrating an OLED in accordance with an exemplary aspect of the present disclosure.

Now, we will describe the OLED in more detail. FIG. 2 is a schematic cross-sectional view illustrating an OLED in accordance with an exemplary aspect of the present disclosure. As illustrated in FIG. 2, the OLED D1 in accordance with the first aspect of the present disclosure includes first and second electrodes 210 and 230 facing each other and an emissive layer 220 having single emitting unit disposed between the first and second electrodes 210 and 230. In one exemplary aspect, the emissive layer 220 comprises an EML 240 disposed between the first and second electrodes 210 and 230. Also, the emissive layer 220 further comprises a HIL 250 and a HTL 260 that is laminated sequentially between the first electrode 210 and the EML 240, and an ETL 270 and an EIL 280 that is laminated sequentially between the EML 240 and the second electrode 230.

Alternatively, the emissive layer 220 may further comprise a first exciton blocking layer, i.e. an EBL 265 disposed between the HTL 260 and the EML 240 and/or a second exciton blocking layer, i.e. a HBL 275 disposed between the EML 240 and the ETL 270.

The first electrode 210 may be an anode that provides a hole into the EML 240. The first electrode 210 may include, but is not limited to, a conductive material having a relatively high work function value, for example, a transparent conductive oxide (TCO). In an exemplary aspect, the first electrode 210 may include, but is not limited to, ITO, IZO, ITZO, SnO, ZnO, ICO, AZO, and the like.

The second electrode 230 may be a cathode that provides an electron into the EML 240. The second electrode 230 may include, but is not limited to, a conductive material having a relatively low work function values, i.e., a highly reflective material such as Al, Mg, Ca, Ag, alloy thereof, combination thereof, and the like. For example, each of the first and second electrodes 210 and 230 may have a thickness of, but is not limited to, about 30 nm to about 300 nm.

In the first aspect, the EML 240 may comprise a first compound and a second compound. For example, the first compound H may be a (first) host and the second compound TD may be delayed fluorescent material, fluorescent material or phosphorescent material. As an example, the organic compound having the structure of Chemical Formulae 1 to 4 may be used as the host H and the second compound TD may be the delayed fluorescent material. The EML may emit red (R), green (G) or blue (B) light. We will describe the kinds of the first and second compounds and energy level relationship between the first and second compound.

The HIL 250 is disposed between the first electrode 210 and the HTL 260 and improves an interface property between the inorganic first electrode 210 and the organic HTL 260. In one exemplary aspect, the HIL 250 may include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiophene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 250 may be omitted in compliance with a structure of the OLED D1.

The HTL 260 is disposed adjacently to the EML 240 between the first electrode 210 and the EML 240. In one exemplary aspect, the HTL 260 may include, but is not limited to, N,N'-Diphenyl-N,N'-bis(3-methylphenyl)-1,1'-biphenyl-4,4'-diamine (TPD), NPB, 4,4'-bis(N-carbazolyl)-1,1'-biphenyl (CBP), Poly[N,N'-bis(4-butylphenyl)-N,N'-bis (phenyl)-benzidine](Poly-TPD), Poly[(9,9-dioctylfluorenyl-2,7-diyl)-co-(4,4'-(N-(4-sec-butylphenyl)diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine. Each of the HIL 250 and the HTL 260 may have a thickness of, but is not limited to, about 5 nm to about 200 nm, preferably about 5 nm to about 100 nm.

The ETL 270 and the EIL 280 may be laminated sequentially between the EML 240 and the second electrode 230. The ETL 270 includes a material having high electron mobility so as to provide electrons stably with the EML 240 by fast electron transportation.

In one exemplary aspect, the ETL 270 may comprise, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

As an example, the ETL 270 may comprise, but is not limited to, tris-(8-hydroxyquinoline aluminum) (Alq$_3$), 2-biphenyl-4-yl-5-(4-t-butylphenyl)-1,3,4-oxadiazole (PBD), spiro-PBD, lithium quinolate (Liq), 1,3,5-Tris(N-phenyl-benzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenaathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr), tris(phenylquinoxaline) (TPQ) and/or diphenyl-4-triphenylsilyl-phenylphosphine oxide (TSPO1).

In another exemplary aspect, the ETL 270 may comprise anyone having the structure of Chemical Formulae 1 to 4. The organic compound having the structure of Chemical Formulae 1 to 4 has an excellent affinity to electrons. In this case, the ETL 270 may comprise only the organic compound having the structure of Chemical Formulae 1 to 4, or comprise the above-described electron transporting materials mixed or doped with the organic compound.

The EIL 280 is disposed between the second electrode 230 and the ETL 270, and can improve physical properties of the second electrode 230 and therefore, can enhance the lifetime of the OLED D1. In one exemplary aspect, the EIL 280 may comprise, but is not limited to, an alkali halide such as LiF, CsF, NaF, BaF$_2$ and the like, and/or an organic metal compound such as lithium quinolate, lithium benzoate, sodium stearate, and the like. Each of the ETL 270 and the EIL 280 may have a thickness of, but is not limited to, about 10 to about 200 nm, preferably about 10 nm to about 100 nm.

When holes are transferred to the second electrode 230 via the EML 240 and/or electrons are transferred to the first electrode 210 via the EML 240, the OLED D1 may have short lifetime and reduced luminous efficiency. In order to prevent these phenomena, the OLED D1 in accordance with this aspect of the present disclosure may have at least one exciton blocking layer adjacent to the EML 240.

For example, the OLED D1 of the exemplary aspect includes the EBL 265 between the HTL 260 and the EML 240 so as to control and prevent electron transfers. In one exemplary aspect, the EBL 265 may comprise, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, 1,3-Bis(carbazol-9-yl)benzene (mCP), mCBP, CuPc, N,N'-bis[4-(bis(3-methylphenyl)amino)phenyl]-N,N'-diphenyl-[1,1'-biphenyl]-4,4'-diamine (DNTPD), TDAPB, 3,5-di(9H-carbazol-9-yl)-N,N-diphenylamine (DCDPA) and/or 2,8-bis(9-phenyl-9H-carbazol-3-yl)dibenzo[b,d]thiophene.

In addition, the OLED D1 may further include the HBL 275 as a second exciton blocking layer between the EML 240 and the ETL 270 so that holes cannot be transferred from the EML 240 to the ETL 270. In one exemplary aspect, the HBL 275 may comprise, but is not limited to, oxadiazole-based compounds, triazole-based compounds, phenanthroline-based compounds, benzoxazole-based compounds, benzothiazole-based compounds, benzimidazole-based compounds, and triazine-based compounds each of which can be used in the ETL 270.

For example, the HBL 275 may comprise a compound having a relatively low HOMO energy level compared to the luminescent materials in EML 240. The HBL 275 may comprise, but is not limited to, BCP, BAlq, Alq$_3$, PBD, spiro-PBD, Liq, Bis-4,5-(3,5-di-3-pyridylphenyl)-2-methylpyrimidine (B3PYMPM), Bis[2-(diphenylphosphino)phenyl] ether oxide (DPEPO), 9-(6-(9H-carbazol-9-yl)pyridine-3-yl)-9H-3,9'-bicarbazole and combination thereof.

In another exemplary aspect, the HBL 275 may comprise anyone having the structure of Chemical Formulae 1 to 4. The organic compound having the structure of Chemical Formulae 1 to 4 has deep HOMO energy level for blocking holes. In this case, the HBL 275 may comprise only the organic compound having the structure of Chemical Formulae 1 to 4, or comprise the above-described hole blocking materials mixed or doped with the organic compound.

As schematically described above, the EML 240 comprise the first compound that is the host H and may be anyone having the structure of Chemical Formulae 1 to 4 and the second compound TD that is the dopant such as the delayed fluorescent material.

In the prior art, the EML 240 has used a p-type host that has excellent affinity to holes. When the p-type host is applied into the EML 240, the recombination zone among holes and electrons is formed at an interface between the EML 240 and the HBL 275 because the p-type host prefers holes to electrons. In this case, some of charges injected into the EML 240 cannot recombine with opposite charges to be quenched, and the luminous efficiency is deteriorated.

On the contrary, the organic compound having the structure of Chemical Formulae 1 to 4 is the bipolar compound that comprises the pyridine moiety having the n-type property and the fused aromatic or hetero aromatic moiety having the p-type property. When the organic compound is applied into the host in the EML 240, the recombination zone among the holes and electrons are distributed uniformly in the whole area of the EML 240 including an interface between the EML 240 and the EBL 265.

In addition, when the organic compound having the structure of Chemical Formulae 1 to 4 is introduced into the EML 240, the OLED D1 can maximize its luminous efficiency because the amount of charges that is not recombined with opposite charges with quenching is minimized. Moreover, when the EML 240 comprises the delayed fluorescent material as the second compound, the OLED D1 can further improve its luminous efficiency, lower its driving voltage and enhances its luminous lifetime.

An external quantum efficiency (EQE, $\eta_{ext}$) of the OLED can be calculated as the following Equation:

$$\eta_{ext} = \eta_{S/T} \times \Gamma \times \Phi \times \eta_{out\text{-}coupling}$$

wherein $\eta_{S/T}$ is a singlet/triplet ratio; $\Gamma$ is a charge balance factor; $\Phi$ is a radiative efficiency; and $\eta_{out\text{-}coupling}$ is an out-coupling efficiency.

When holes and electrons meet to form exciton, singlet exciton with a paired spin state and triplet exciton with an unpaired spin state is generated in a ratio of 1:3 in theory. Since only the singlet exciton participates in luminescence and the remaining 75% triplet excitons cannot participate in luminescence in the fluorescent material, the singlet/triplet ratio is 0.25 in the conventional fluorescent material. Therefore, when taking all four factors defined in the above Equation into account, the maximum luminous efficiency of the OLED using the conventional fluorescent material is only about 5%.

On the other hand, phosphorescent materials have a luminescent mechanism that converts both the singlet and triplet excitons to light. Phosphorescent materials convert singlet exciton into triplet exciton through intersystem crossing (ISC). Therefore, when using phosphorescent materials using both singlet exciton and triplet exciton, it is possible to improve the low luminous efficiency of the fluorescent materials. However, blue phosphorescent materials have too low color purity and too short lifetime to be applied into commercial display devices. Thus, it is necessary to improve the disadvantages of the phosphorescent materials and the low luminous efficiency of the blue luminescent materials.

Recently, a delayed fluorescent material, which can solve the problems accompanied by the conventional art fluorescent and/or phosphorescent materials, has been developed. Representative delayed fluorescent material is a thermally-activated delayed fluorescent (TADF) material. Since the delayed fluorescent material generally has both an electron donor moiety and an electron acceptor moiety within its molecular structure, it can be converted to an intramolecular charge transfer (ICT) state. In case of using the delayed fluorescent material as a dopant, it is possible to use both the singlet energy and the triplet energy during the luminescent process, unlike the conventional fluorescent materials.

Figure 3:
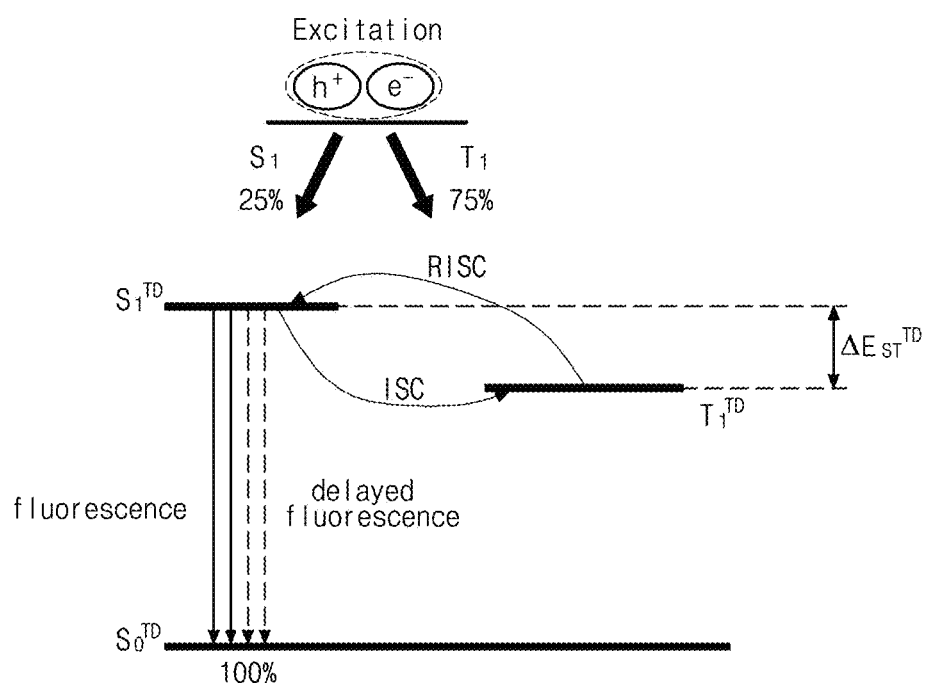
FIG. 3 is a schematic diagram illustrating a luminous mechanism of a delayed fluorescent material.

The luminous mechanism of the delayed fluorescent material will be explained with referring to FIG. 3, which is a schematic diagram illustrating a luminous mechanism of delayed fluorescent material in the EML. As illustrated in FIG. 3, the excitons of singlet energy level $S_1^{TD}$ as well as the excitons of triplet energy level $T_1^{TD}$ in the delayed fluorescent material TD can be transferred to an intermediate energy level state, i.e. ICT state, and then the intermediate stated excitons can be shifted to a ground state ($S_0^{TD}$; $S_1^{TD} \rightarrow ICT \leftarrow T_1^{TD}$). Since the excitons of singlet energy level $S_1^{TD}$s well as the excitons of triplet energy level $T_1^{TD}$ in the delayed fluorescent material TD is involved in the luminescent process, the delayed fluorescent material TD can improve its luminous efficiency.

Since both the HOMO and the LUMO are widely distributed over the whole molecule within the common fluorescent material, it is not possible to inter-convert exciton energies between the singlet energy level and the triplet energy level within the common fluorescent material (selection rule). In contrast, since the delayed fluorescent material TD, which can be converted to ICT state, has little orbital overlaps between HOMO and LUMO, there is little interaction between the HOMO state and the LUMO state. As a result, the changes of spin states of electrons do not have an influence on other electrons, and a new charge transfer band (CT band) that does not follow the selection rule is formed within the delayed fluorescent material.

In other words, since the delayed fluorescent material TD has the electron acceptor moiety spacing apart from the electron donor moiety within the molecule, it exists as a polarized state having a large dipole moment within the molecule. As the interaction between HOMO and LUMO becomes little in the state where the dipole moment is polarized, the triplet excitons as well as the singlet excitons can be converted to ICT state. In other words, ICT complex can be excited to a CT state in which singlet exciton and triplet exciton can be exchanged mutually, thus the triplet excitons as well as singlet excitons can be involved in the luminescent process. In case of driving an OLED that includes the delayed fluorescent material TD, both 25% singlet excitons and 75% triplet excitons are converted to ICT state by heat or electrical field, and then the converted excitons drops to the ground state $S_0$ with luminescence. Therefore, the delayed fluorescent material TD may have 100% internal quantum efficiency in theory.

The delayed fluorescent material TD must has an energy level bandgap $\Delta E_{ST}^{TD}$ equal to or less than about 0.3 eV, for example, from about 0.05 to about 0.3 eV, between the excited singlet energy level $S_1^{TD}$ and the excited triplet energy level $T_1^{TD}$ so that exciton energy in both the excited singlet energy level $S_1^{TD}$ and the excited triplet energy level $T_1^{TD}$ can be transferred to the ICT state. The material having little energy level bandgap between the singlet energy level $S_1^{TD}$ and the triplet energy level $T_1^{TD}$ can exhibit common fluorescence with Inter system Crossing (ISC) in which the excitons of singlet energy level $S_1^{TD}$ can be transferred to the excitons of triplet energy level $T_1^{TD}$, as well as delayed fluorescence with Reverser Inter System Crossing (RISC) in which the excitons of triplet energy level $T_1^{TD}$ can be transferred upwardly to the excitons of singlet energy level $S_1^{TD}$, and then the exciton of singlet energy level $S_1^{TD}$ transferred from the triplet energy level $T_1^{TD}$ can be transferred to the ground state $S_0^{TD}$.

Since the delayed fluorescent material TD obtain 100% luminous efficiency in theory, it can realize excellent internal quantum efficiency as the conventional phosphorescent material. In this case, the host can induce the triplet excitons at the delayed fluorescent material to participate in the luminescent process without quenching or non-radiative recombination. To this end, the energy levels between the host and the delayed fluorescent material should be adjusted.

Figure 4:
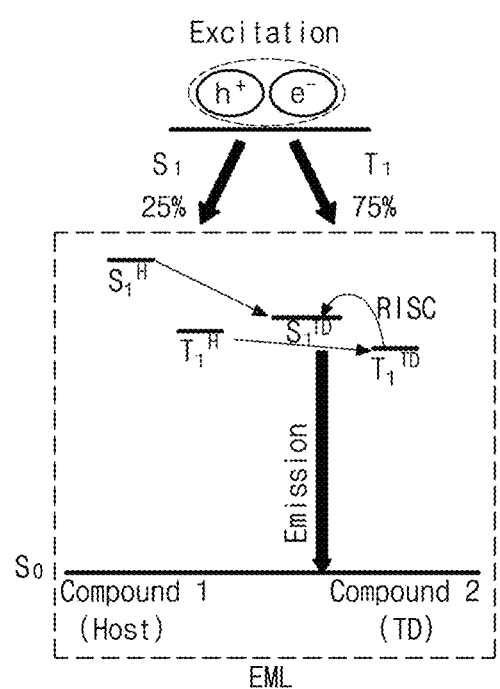
FIG. 4 is a schematic diagram illustrating luminous mechanism by energy level bandgap among luminous materials in accordance with an exemplary aspect of the present disclosure.

FIG. 4 is a schematic diagram illustrating luminous mechanism by energy level bandgap among luminous materials in accordance with an exemplary aspect of the present disclosure. As illustrated in FIG. 4, each of an excited singlet energy level $S_1^H$ and an excited triplet energy level $T_1^H$ of the first compound, which can be the host in the EML 240, is higher than each of the excited singlet energy level $S_1^{TD}$ and the excited triplet energy level $T_1^{TD}$ of the second compound having the delayed fluorescent property. As an example, the excited triplet energy level $T_1^H$ of the first compound may be higher than the excited triplet energy level $T_1^{TD}$ of the second compound by at least about 0.2 eV, preferably at least about 0.3 eV, and more preferably at least about 0.5 eV.

When each of the excited triplet energy level $T_1^H$ and the excited singlet energy level $S_1^H$ of the first compound is not high enough than each of the excited triplet energy level $T_1^{TD}$ and the excited singlet energy level $S_1^{TD}$ of the second compound TD, the triplet state exciton energy of the second compound TD may be reversely transferred to the excited triplet energy level $T_1^H$ of the first compound. In this case, the triplet exciton reversely transferred to the first compound where the triplet exciton cannot be emitted is quenched as non-emission so that the triplet exciton energy of the second compound TD having the delayed fluorescent property cannot contribute to luminescence. As an example, the first compound have the excited triplet energy level $T_1^H$ equal to or more than, but is no limited to, about 2.7 eV, preferably about 2.85 eV.

The second compound having the delayed fluorescent property may have the energy level bandgap $\Delta E_{ST}^{TD}$ between the excited singlet energy level $S_1^{TD}$ and the excited triplet energy level $T_1^{TD}$ equal to or less than about 0.3 eV, for example between about 0.05 eV and about 0.3 eV (see, FIG. 3).

In addition, it is necessary to adjust properly HOMO energy levels and LUMO energy levels of the first compound and the second compound. For example, it is preferable that an energy level bandgap ($|HOMO^H-HOMO^{TD}|$) between the HOMO energy level ($HOMO^H$) of the first compound and the HOMO energy level ($HOMO^{TD}$) of the second compound, or an energy level bandgap ($|LUMO^H-LUMO^{TD}|$) between the LUMO energy level ($LUMO^H$) of the first compound and the LUMO energy level ($LUMO^{TD}$) of the second compound may be equal to or less than about 0.5 eV, for example, between about 0.1 eV to about 0.5 eV. In this case, the charges can be transported efficiently from the first compound as the host to the second compound as the delayed fluorescent material and thereby enhancing the ultimate luminous efficiency in the EML 240.

Moreover, an energy level bandgap ($Eg^H$) between the HOMO energy level ($HOMO^H$) and the LUMO energy level ($LUMO^H$) of the first compound may be larger than an energy level bandgap ($Eg^{TD}$) between the HOMO energy level ($HOMO^{TD}$) and the LUMO energy level ($LUMO^{TD}$) of the second compound. As an example, the HOMO energy level ($HOMO^H$) of the first compound is deeper than the HOMO energy level ($HOMO^{TD}$) of the second compound, and the LUMO energy level ($LUMO^H$) of the first compound is shallower than the LUMO energy level ($LUMO^{TD}$) of the second compound.

The organic compound having the structure of Chemical Formulae 1 to 4 comprises the pyridine moiety having the n-type property and the fused aromatic or fused hetero aromatic moiety having the p-type property. Also, the organic compound includes at least one adamantyl group linked to the pyridine moiety and/or the fused aromatic or fused hetero aromatic moiety, thus it has very excellent thermal stability and can maintain its excited singlet and triplet energy levels at a high level and its crystallization caused by Joule's heat generated in driving the OLED D1 can be prevented. In addition, when introducing the first compound, the organic compound as the bipolar molecule, into the EML 240, the recombination zone by holes and electrons are distributed uniformly over the whole area in the EML 240.

In addition, since anyone having the structure of Chemical Formulae 1 to 4 has very high excited singlet and/or triplet energy levels and wide energy bandgap, it is proper to apply the organic compound into the host in the EML 240 as well as the material of the ETL 270 and/or the HBL 275. Particularly, when the organic compound is used in the EML 240 together with the second compound as the delayed fluorescent material, the exciton energies can be transferred from the organic compound to the second compound without energy loss in luminescence process.

In other words, when anyone having the structure of Chemical Formulae 1 to 4 is used as the host in the EML 240 of the OLED D1, it is possible to minimize exciton quenching resulted from the interaction between the host excitons and the adjacent polarons and to prevent the luminous lifetime owing to electrical oxidation and optical oxidation from reducing. In addition, the organic compound has excellent anti-thermal property, wide energy bandgap and a high excited triplet energy level.

Accordingly, when the organic compound having the structure of Chemical Formulae 1 to 4 is used as the host in the EML 240, the exciton energy generated at the organic compound can be efficiently transferred to second compound as the dopant. Alternatively, the organic compound may be used as the material of the ETL 270 and/or the HBL 275. In case of applying the organic compound into the emissive layer 220, the OLED D1 may have enhanced luminous efficiency. As the damages to the materials applied into the EML 240 decreases, it is possible to fabricate the OLED having long luminous lifetime and excellent color purity.

In one exemplary aspect, when the organic compound having the structure of Chemical Formulae 1 to 4 is used as the first compound, it is preferable to use the second compound having delayed fluorescent property and adequate energy levels relative to the first compound. For example, the delayed fluorescent material as the second compound may emit blue (B), green (G) or red (R) light. As an example, the second compound may have the excited singlet energy level $S_1^{TD}$, but is not limited to, between about 2.7 eV and about 2.75 eV, and the excited triplet energy level Tim between about 2.4 eV and about 2.5 eV in order to implement luminescence applicable to the display device.

For example, the second compound having the delayed fluorescent property may have the HOMO energy level $HOMO^{TD}$ between about −5.0 eV and about −6.0 eV, preferably between about −5.0 eV and about −5.5 eV, the LUMO energy level $LUMO^{TD}$ between about −2.5 eV and about −3.5 eV, preferably between about −2.5 eV and about −3.0 eV, and the energy level bandgap $Eg^{TD}$ between the HOMO and LUMO energy levels between about 2.2 eV and about 3.0 eV, preferably between about 2.4 eV and about 2.8 eV. On the other hand, the first compound may have the HOMO energy level $HOMO^H$ between about −5.5 eV and about −6.3 eV, preferably between about −5.7 eV and about −6.0 eV, the LUMO energy level $LUMO^H$ between about −2.0 eV and about −3.0 eV, preferably between about −2.1 eV and about −2.5 eV, and the energy level bandgap $Eg^H$ between the HOMO and LUMO energy levels between about 3.0 eV and about 4.0 eV, preferably between about 3.3 eV and about 3.8 eV.

The delayed fluorescent material that can be used as the second compound of the EML 240 in accordance with an exemplary aspect may have the following structure of Chemical Formula 5:

[Chemical Formula 5]

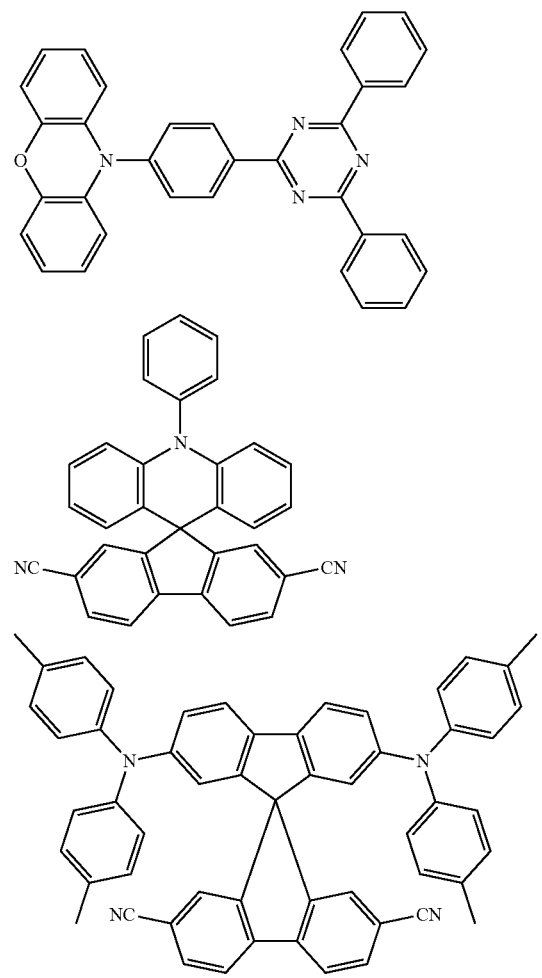

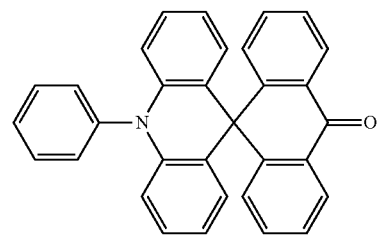
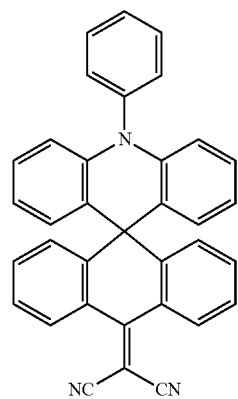
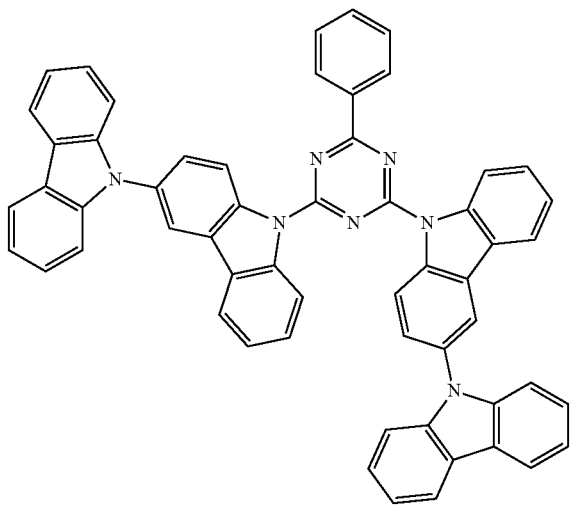
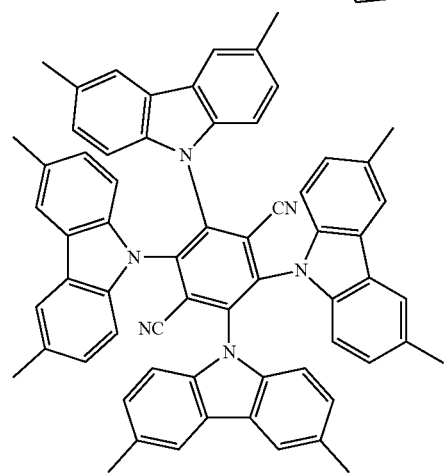
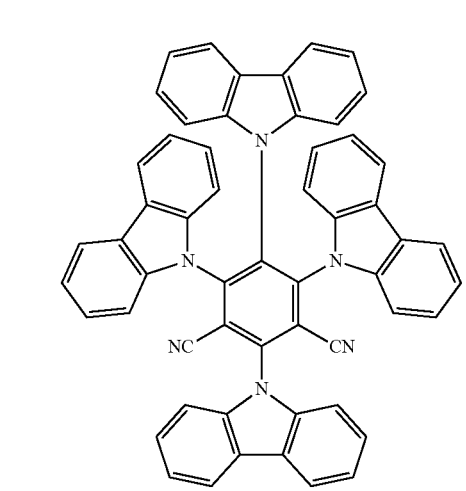
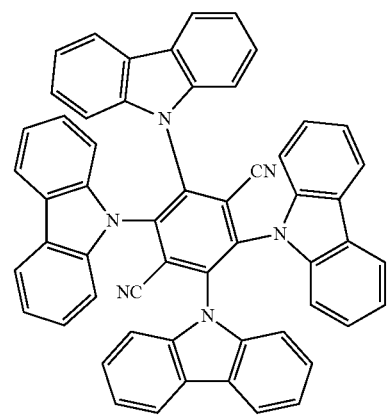
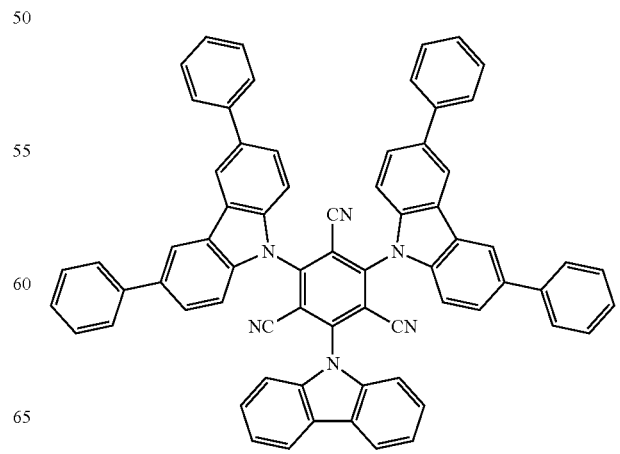

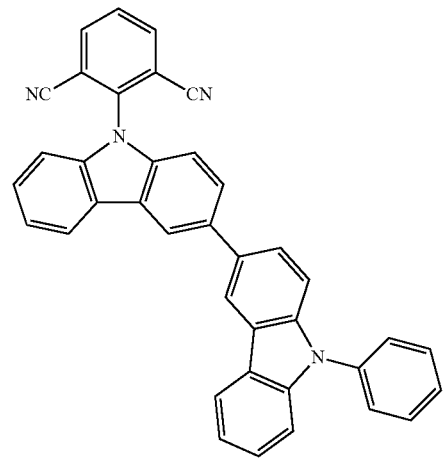
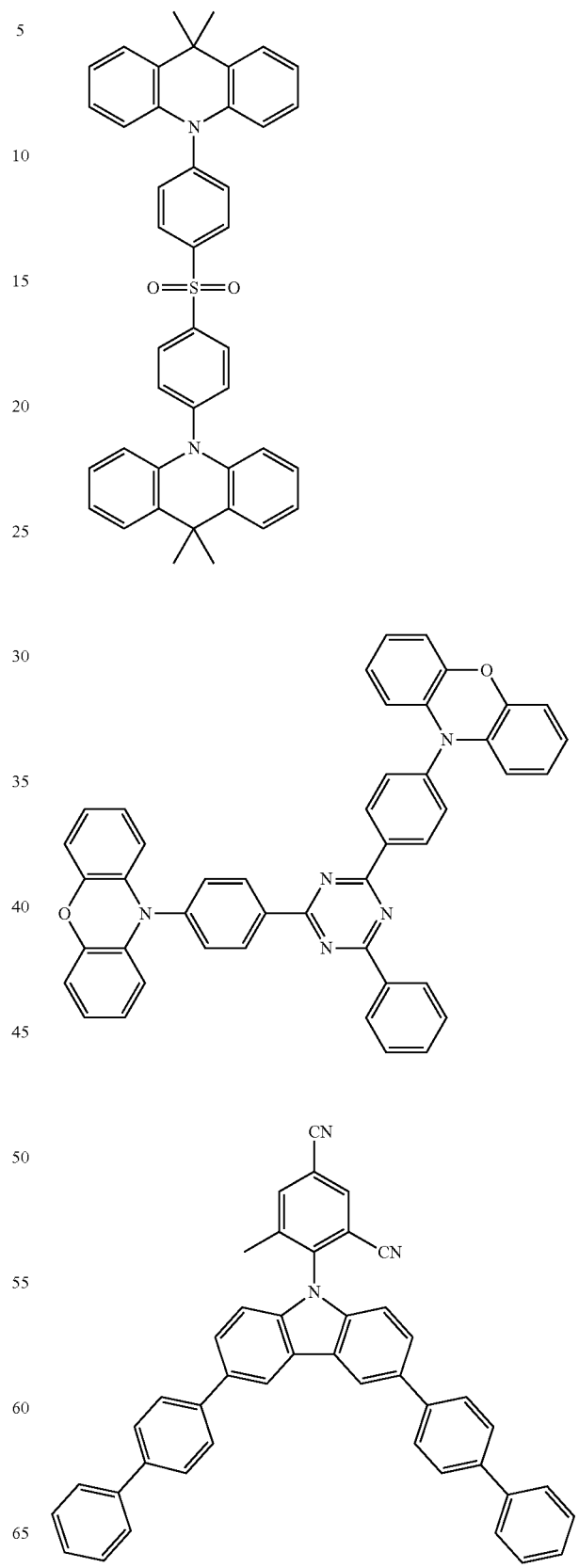

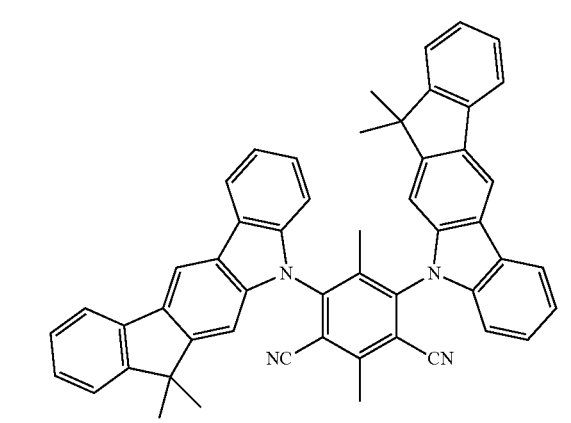
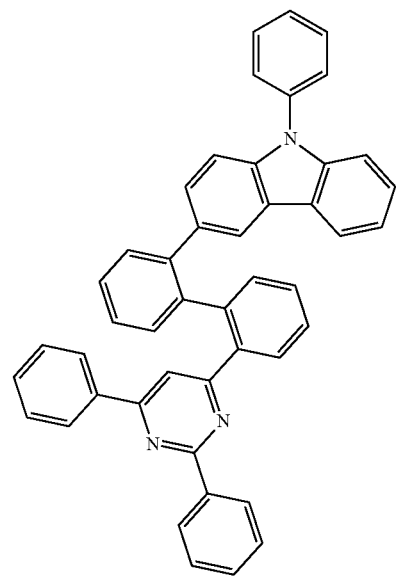
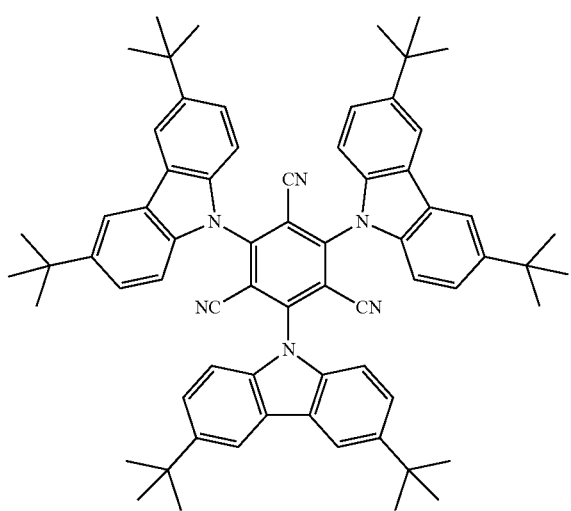
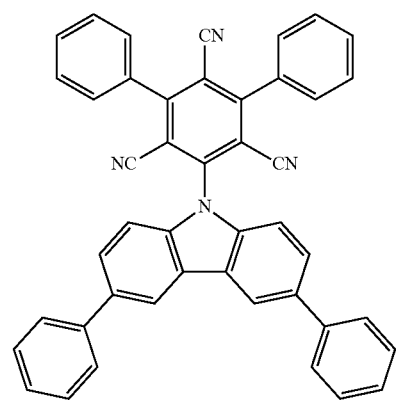
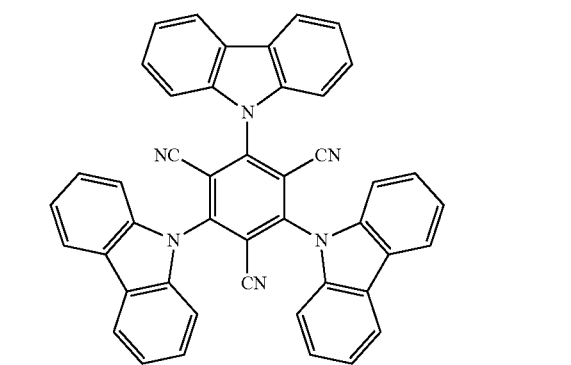
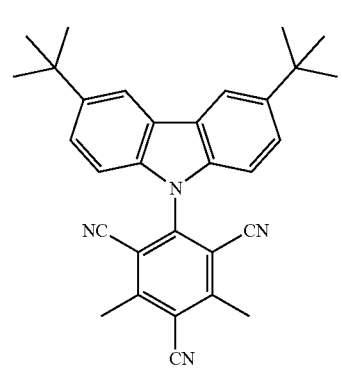

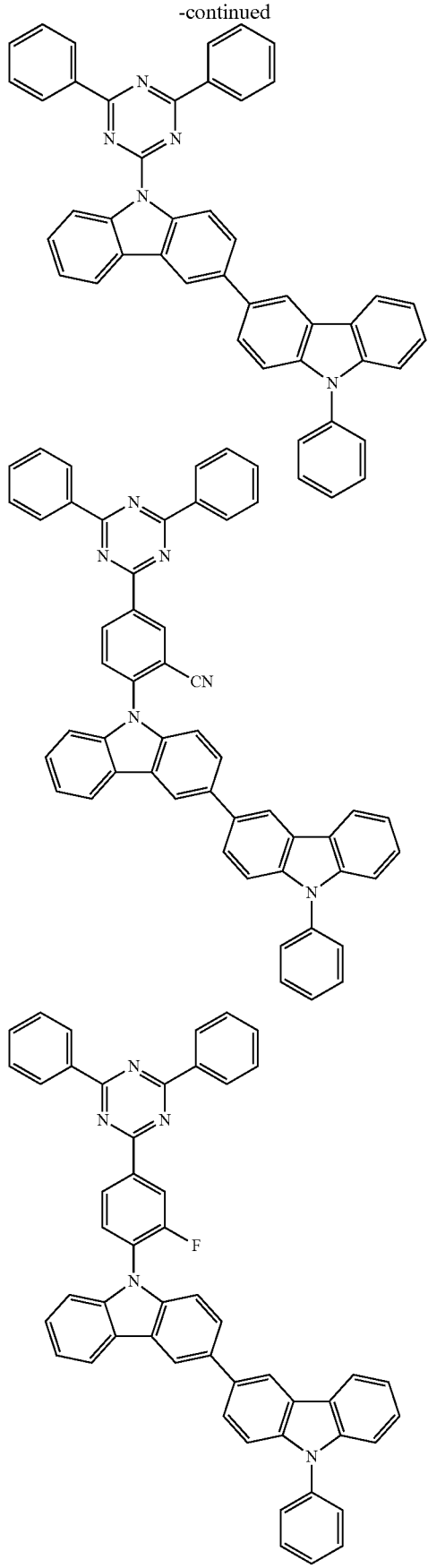
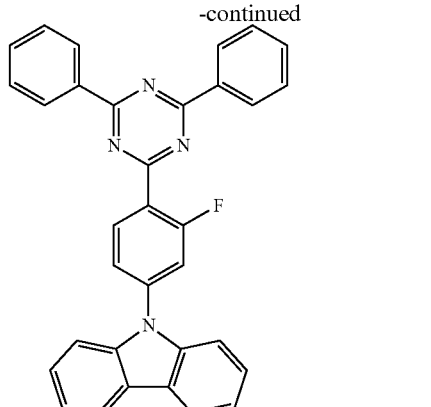
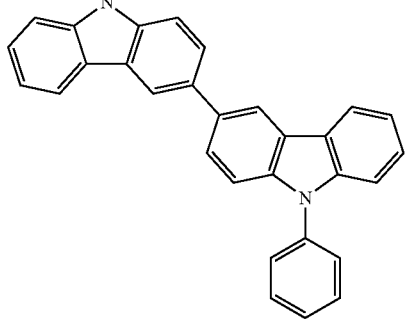
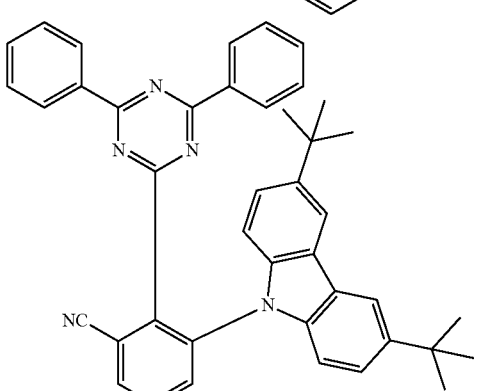
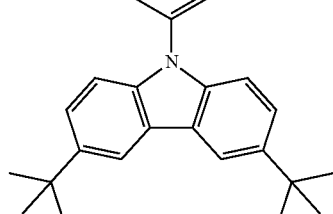
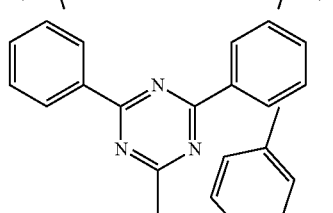
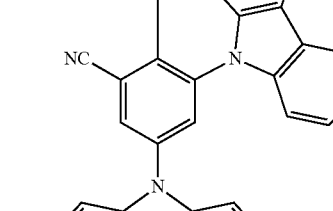
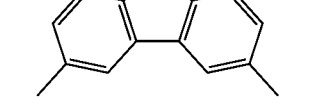

51
-continued
52
-continued
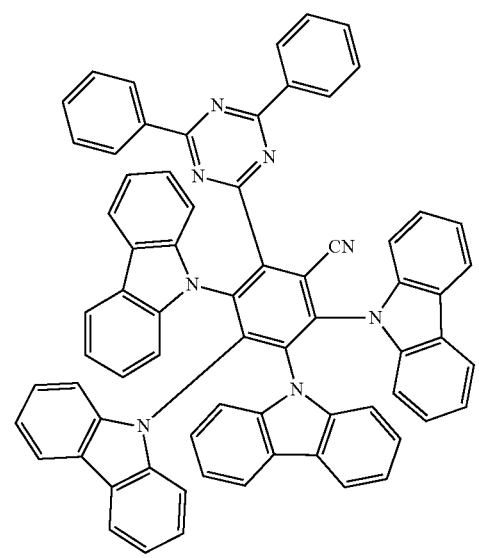
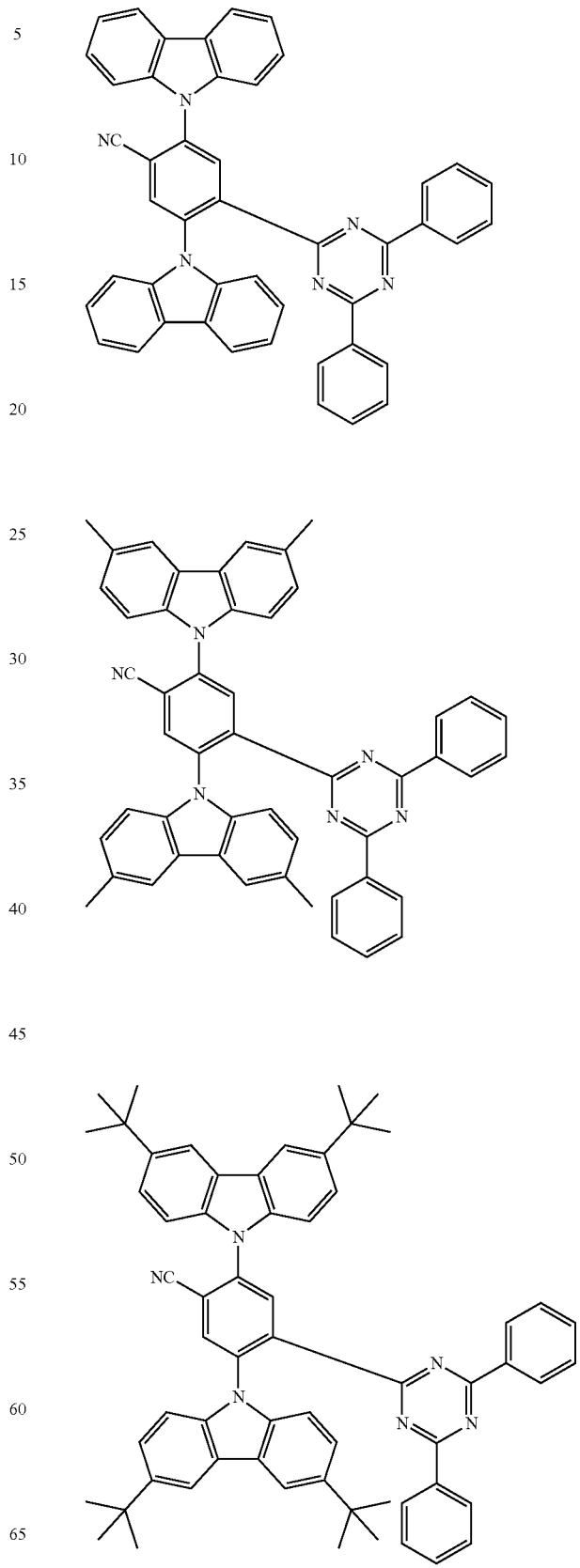

53
-continued
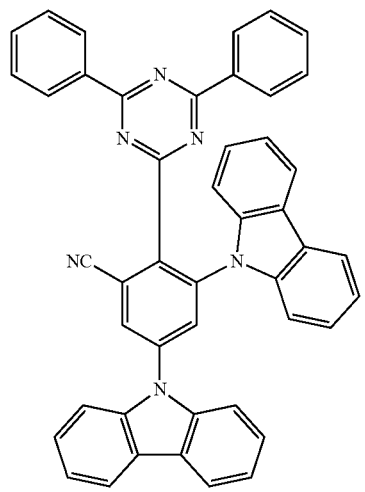
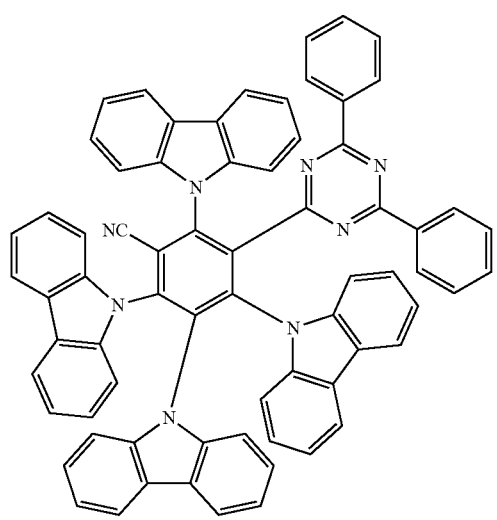
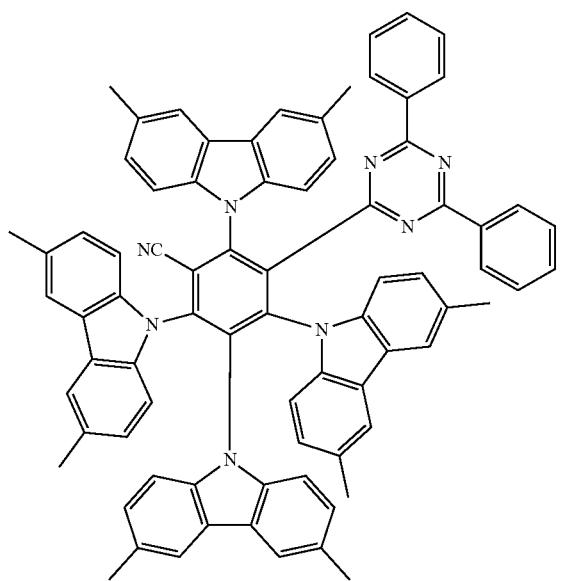
54
-continued
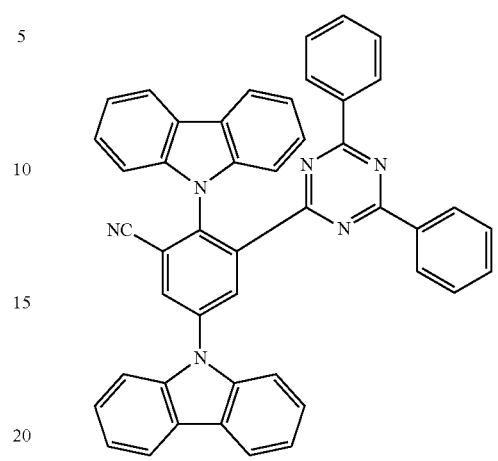
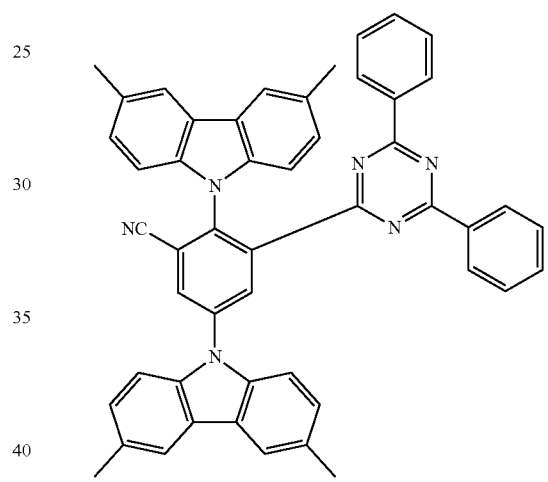
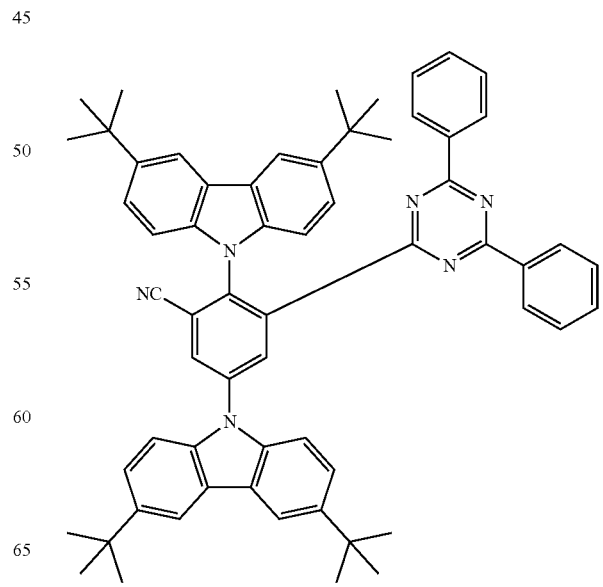

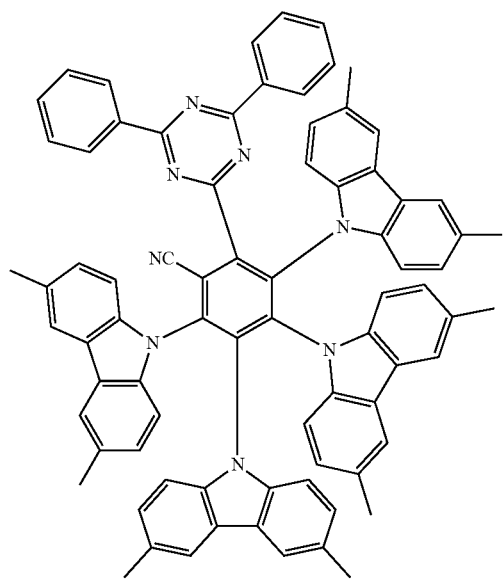
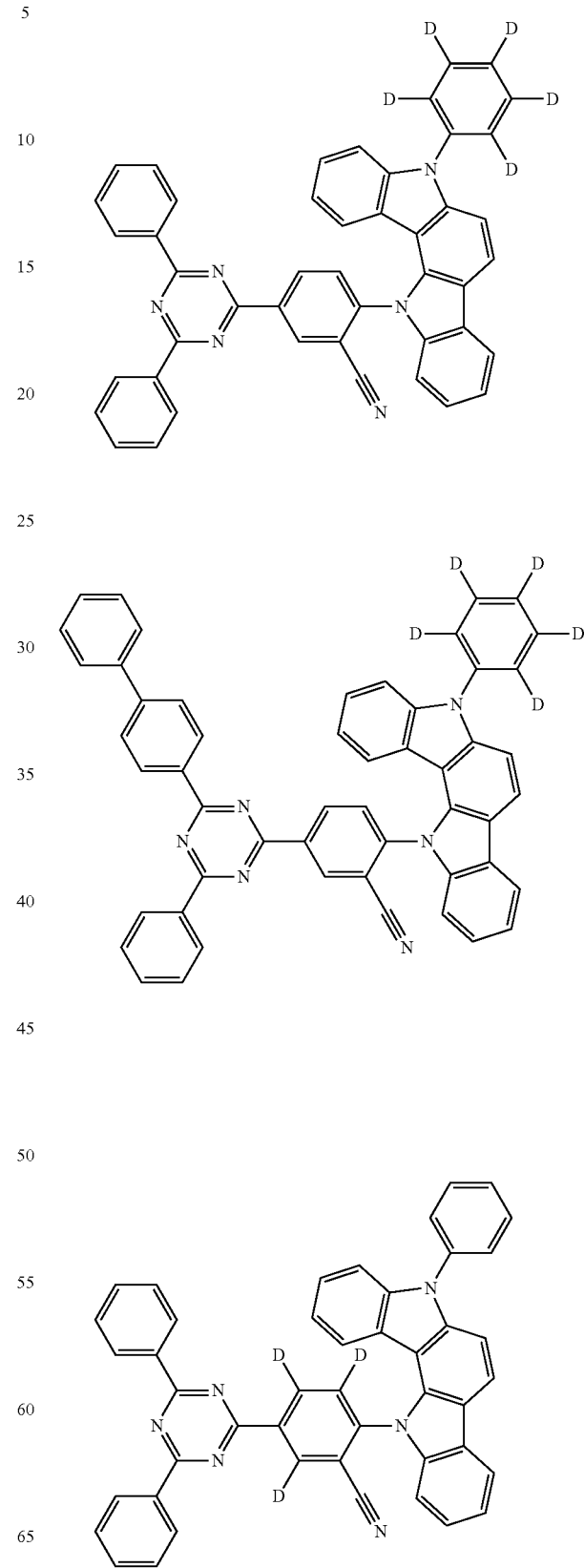

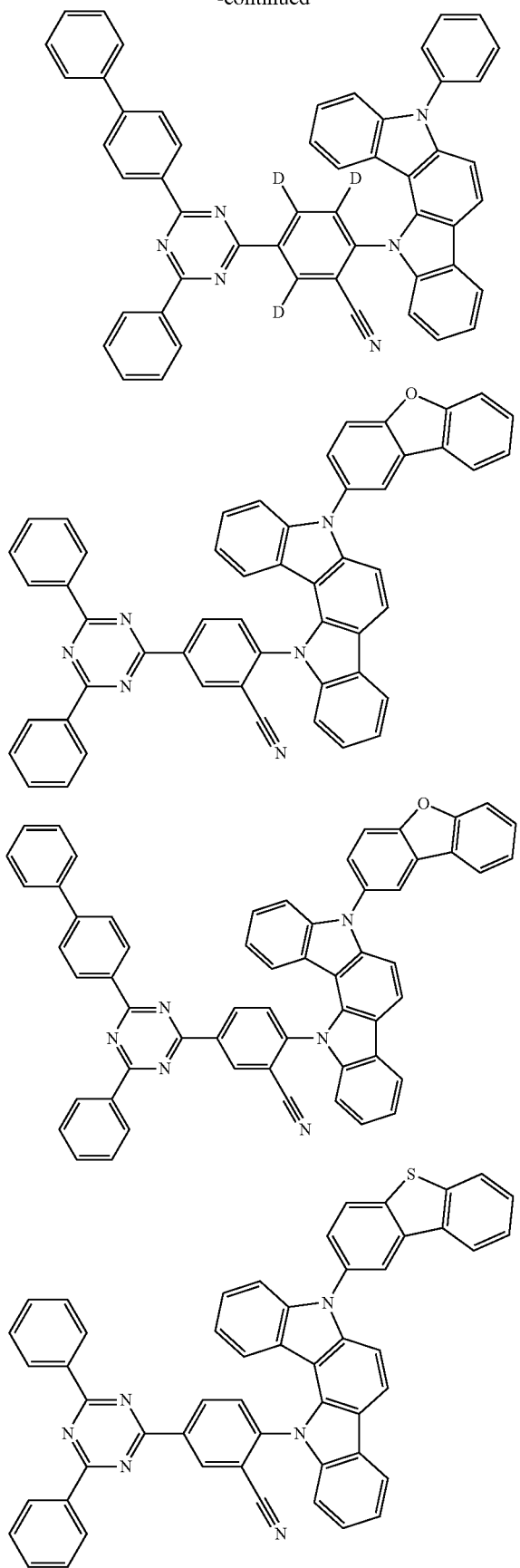
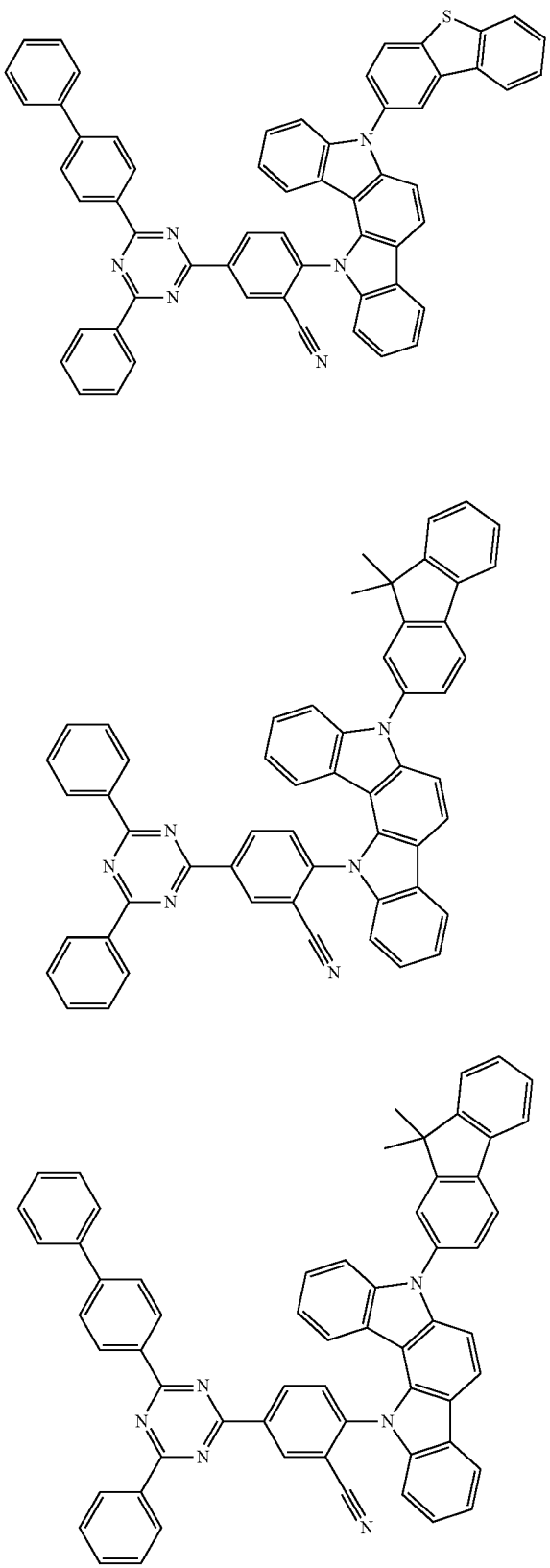

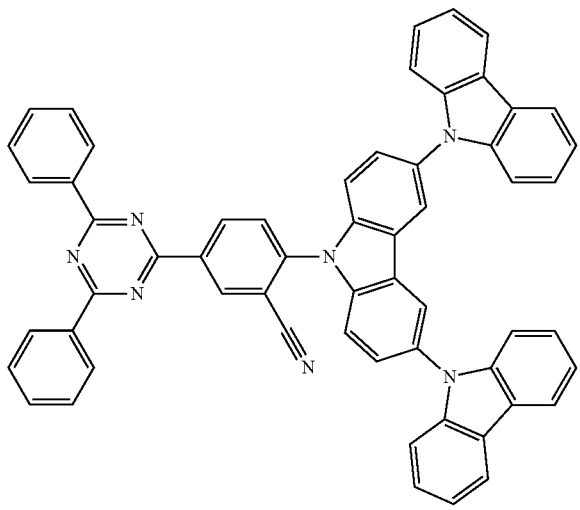

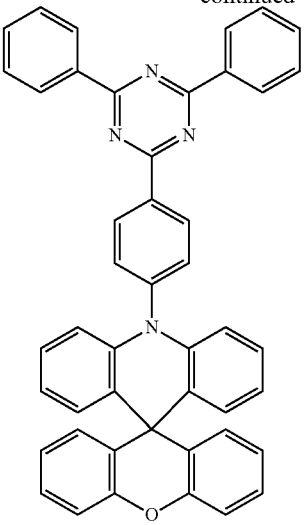

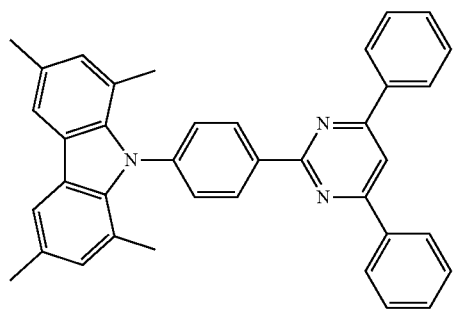

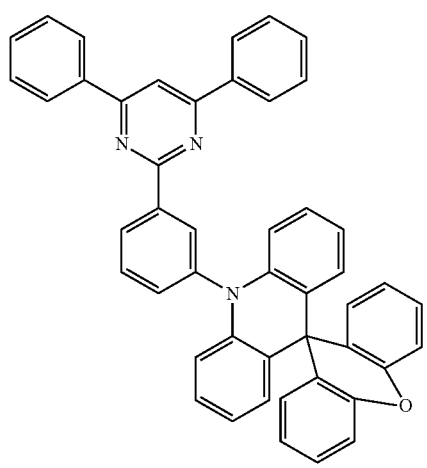

In one exemplary aspect, the second compound as blue-emitting delayed fluorescent material in the EML 240 may comprise, but is not limited to, 10-(4-(diphenylphosphoryl)phenyl)-10H-phenoxazine (SPXZPO), 10,10'-(4,4'-(phenylphosphoryl)bis4,1-phenylene))bis(10H-phenoxazine) (DPXZPO), 10,10',10''-(4,4',4''-phosphoryltris(benzene-4,1-diyl))tris(10H-phenoxazine) (TPXZPO), 9,9'-(5-(4,6-diphenyl-1,3,5-triazin-2-yl)-1,3-phenylene)bis(9H-carbazole) (DcZTrz), 9,9',9'',9'''-((6-phenyl-1,3,5-triazin-2,4-diyl)bis(benzene-5,3,1-triyl))tetrakis(9H-carbazole) (DDczTrz), 2,7-bis(9,9-dimethylacridin-10(9H)-yl)-9,9-dimethyl-9H-thioxanthene-10,10-dioxide (DMTDAc), 9,9'-(4,4'sulfonylbis(4,1-phenylene))bis(3,6-dimethoxyl-9H-carbazole) (DMOC-DPS), 10,10'-(4,4'-Sulfonylbis(4,1-phenylene))bis(9,9-dimethyl-9,10-dihydroacridine (DMAC-DPS), 10-(4-(4,6-diphenyl-1,3,5-triazin-2-yl)phenyl)-9,9-dimethyl-9,10-dihydroacridine (DMAC-TRZ), 10-phenyl-10H,10'H-spiro[acridine-9,9'-anthracen]-10'-one (ACRSA), 3,6-dibenzoyl-4,5-di(1-methyl-9-phenyl-9H-carbazoyl)-2-ethynylbenzonitrile (Cz-VPN), 9,9',9''-(5-(4,6-diphenyl-1,3,5-triazin-2-yl)benzene-1,2,3-triyl)tris(9H-carbazole) (TcZTrz), 2'-(10H-phenoxazin-10-yl)-[1,1':3',1''-terphenyl]-5'-carbonitrile (mPTC), bis(4-(9H-3,9'-bicarbazol-9-yl)phenyl)methanone (CC2BP), 9'-[4-(4,6-diphenyl-1,3,5-triazin-2-yl)phenyl]-3,3'',6,6''-tetraphenyl-9,3':6',9''-ter-9H-carbazole (BDPCC-TPTA), 9'-[4-(4,6-diphenyl-1,3,5-triazin-2-yl)phenyl]-9,3':6',9''-ter-9H-carbazole (BCC-TPTA), 9-(4-(4,6-diphenyl-1,3,5-triazin-2-yl)phenyl)-3',6'-diphenyl-9H-3,9'-bicarbazole (DPCC-TPTA), 10-(4,6-diphenyl-1,3,5-triazin-2-yl)-10H-phenoxazine (Phen-TRZ), 9-(4-(4,6-diphenyl-1,3,5-triazin-2-yl)phenyl)-9H-carbazole (Cab-Ph-TRZ), 10-(4-(4,6-diphenyl-1,3,5-triazin-2-yl)phenyl)-10H-spiro[acridine-9,9'-fluorene] (SpiroAC-TRZ), 4,6-di(9H-carbazol-9-yl)isophthalonitrile (DczIPN), 3CzFCN and 2,3,4,6-tetra(9H-carbazol-9-yl)-5-fluorobenzonitrile (4CzFCN).

In another embodiment, the second compound as green-emitting delayed fluorescent material in the EML 240 may comprise, but is not limited to, 5'-(phenoxazin-10-yl)-[1,1': 3',1''-terphenyl]-2'-carbonitrile; oPTC), 2-biphenyl-4,6-bis(12-phenylindolo[2,3-a]carbazol-11-yl)-1,3,5-triazine (PIC-TRZ), 9,9',9''-(5-(4,6-diphenyl-1,3,5-triazin-2-yl)benzene-1,2,3-triyl)tris(3,6-dimentyl-9H-carbazole (TmCzTrz), 2,5-bis(4-(10H-phenoxazin-10-yl)phenyl)-1,3,4-oxadiazole (2PXZ-OXD), bis(4-(9,9-dimethylacridin-10(9H)-yl)phenyl)methanone (DMAC-BP), 2-(9-phenyl-9H-carbazol-3-yl)-10,10-dioxide-9H-thioxanthen-9-one (TXO-PhCz), 2,4,5,6-tetra(9H-carbazol-9-yl)isophthalonitrile (4CzIPN), 3,4,5,6-tetra(9H-carbazol-9-yl)isophthalonitrile (4CzPN), 2,3,4,6-tetra(9H-carbazol-9-yl)-5-fluorobenzonitrile (4CzFCN), 6,6-(9H,9'H-[3,3'-bicarbazole]-9,9'-diyl)bis(4-(9H-carbazol-9-yl)isophthalonitrile (33TczPN), 4,5-bis(5H-benzofuro[3,2-c]carbazol-5-yl)phthalonitrile (BFCz-2CN), 4,5-bis(5H-benzo[4,5]thieno[3,2-c]carbazol-5-yl)phthalonitrile (BTCz-2CN), 4,4"-bis(9,9-dimethylacridin-10(9H)-yl)-[1,1':2',1"-terphenyl]-4',5'-dicarbonitrile (Ac-VPN), 4,4"-di (10H-phenoxazin-10-yl)-[1,1':2',1"-terphenyl]-4',5'-dicarbonitrile (Px-VPN), 5,5'-(9H,9'H-[3,3'-bicarbazole]-9,9'-diyl)diisophthalnonitrile (35IPNDcz), 2,5'-(9H,9'H-[3,3'-bicarbazole]-9,9'-diyl)diisophthalnonitrile (26IPNDcz), 9,9',9'''-(5-(4,6-diphenyl-1,3,5-triazin-2-yl)benzene-1,2,3-triyl)-tris(9H-carbazole) (TcZTrz) and 32alCTRZ.

In still another exemplary aspect, the second compound as red-emitting delayed fluorescent material in the EML 240 may comprise, but is not limited to, 1,3-bis[4-(10H-phenoxazin-10-yl)benzoyl]benzene (mPx2BBP), 2,3,5,6-tetrakis(3,6-diphenylcarbazol-9-yl)-1,4-dicyanobenzene (4CzTPN-Ph), 10,10'-(sulfonylbis(4,1-phenylene))bis(5-phenyl-5,10-dihydrophenazine) (PPZ-DPS), 5,10-bis(4-(benzo[d]thiazol-2-yl)phenyl)-5,10-dihydrophenazine (DHPZ-2BTZ), 5,10-bis(4-(4,6-diphenyl-1,3,5-triazin-2-yl) phenyl)-5,10-dihydrophenazine (DHPZ-2TRZ) and 7,10-bis (4-(diphenylamino)phenyl)-2,3-dicyanopyrazino phenanathrene (TPA-DCPP).

When the EML 240 includes the first compound as the host and the second compound as the delayed fluorescent material, the contents of the second compound in the EML 240 may be, but is not limited to, about 1 wt % to about 70 wt %, preferably about 10 wt % to about 50 wt %, and more preferably about 20 wt % to about 50 wt %. The EML 240 may have a thickness of, but is not limited to, about 20 nm to about 200 nm, preferably about 20 to about 100 nm, and more preferably about 30 nm to about 50 nm.

Figure 5:
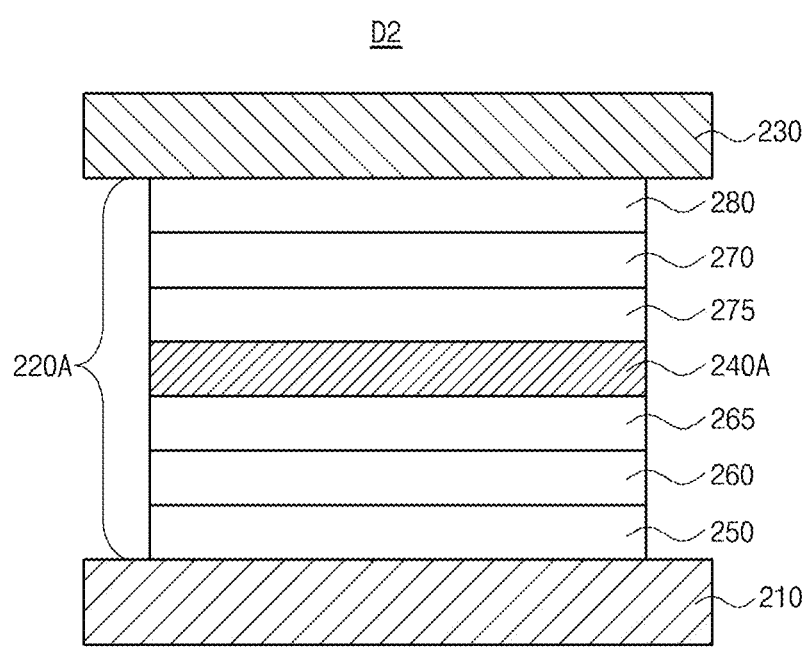
FIG. 5 is a schematic cross-sectional view illustrating an OLED in accordance with another exemplary aspect of the present disclosure.

In the above first aspect, the EML 240 includes only the first compound as the host and the second compound as the dopant. Unlike that aspect, the EML may include plural dopants having different luminous properties. FIG. 5 is a schematic cross-sectional view illustrating an OLED in accordance with another exemplary aspect of the present disclosure. As illustrated in FIG. 5, the OLED D2 comprises the first electrode 210, the second electrode 230 facing the first electrode 210 and an emissive layer 220A disposed between the first and second electrodes 210 and 230. The emissive layer 220A having single emitting unit comprises an EML 240A. Also, the emissive layer 220A comprise the HIL 250 and the HTL 260 each of which is disposed sequentially between the first electrode 210 and the EML 240A, and the ETL 270 and the EIL 280 each of which is disposed sequentially between the EML 240A and the second electrode 230. Alternatively, the emissive layer 220A may further comprise the EBL 265 disposed between the HTL 260 and the EML 240A and/or the HBL 275 disposed between the EML 240A and the ETL 270. The configurations of the first and second electrodes 210 and 230 as well as other layers except the EML 240A in the emissive layer 220A is substantially identical to the corresponding electrodes and layers in the OLED D1.

In the second aspect, the EML 240A comprise the first compound, the second compound and a third compound. The first compound may be the host, the second compound may be the delayed florescent material (first dopant), and the third compound may be the fluorescent material (second dopant). The first compound may comprise any organic compound having the structure of Chemical Formulae 1 to 4. When the EML 240 further comprises the fluorescent material as well as the delayed fluorescent material as dopants, the OLED D2 can further improve its luminous efficiency and color purity by adjusting energy levels among those luminous materials.

When an EML includes only the second compound having the delayed fluorescent property as the dopant, the EML may implement high internal quantum efficiency as the prior art phosphorescent materials including heavy metals because the dopant can exhibit 100% internal quantum efficiency in theory.

However, because of the bond formation between the electron acceptor and the electron donor and conformational twists within the delayed fluorescent material, additional charge transfer transition (CT transition) within the delayed fluorescent material is caused thereby, and the delayed fluorescent material has various geometries. As a result, the delayed fluorescent materials show luminescence spectra having very broad FWHM (full-width at half maximum) in the course of luminescence, which results in poor color purity. In addition, the delayed fluorescent material utilizes the triplet exciton energy as well as the singlet exciton energy in the luminescence process with rotating each moiety within its molecular structure, which results in twisted internal charge transfer (TICT). As a result, the luminous lifetime of an OLED including only the delayed fluorescent materials may be reduced owing to weakening of molecular bonding forces among the delayed fluorescent materials.

In the second aspect, the EML 240A further includes the third compound, which may be a fluorescent or phosphorescent material, in order to prevent the color purity and luminous lifetime from being reduced in case of using only the delayed fluorescent material as the dopant. The triplet exciton energy of the second compound, which may be the delayed fluorescent material TD, is converted upwardly to its own singlet exciton energy by RISC mechanism, then the converted singlet exciton energy of the second compound can be transferred to the third compound, which may be the fluorescent or phosphorescent material, in the same EML 240A by Forster Resonance Energy Transfer (FRET) mechanism.

Figure 6:
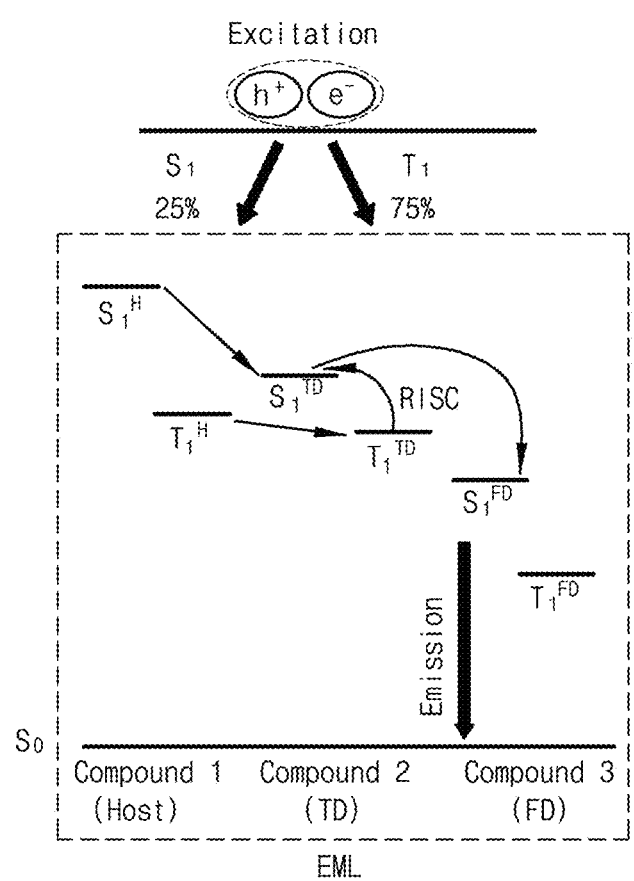
FIG. 6 is a schematic diagram illustrating luminous mechanism by energy level bandgap among luminous materials in accordance with another exemplary aspect of the present disclosure.

When the EML 240A includes the first compound which may be any organic compound having the structure of Chemical Formulae 1 to 4, the second compound having the delayed fluorescent property and the third compound which is the fluorescent or phosphorescent material, it is necessary to adjust properly energy levels among those luminous materials. FIG. 6 is a schematic diagram illustrating luminous mechanism by energy level bandgap among luminous materials in accordance with another exemplary aspect of the present disclosure.

An energy level bandgap $\Delta E_{ST}^{TD}$ between the excited singlet energy level $S_1^{TD}$ and the excited triplet energy level $T_1^{TD}$ of the second compound, which is the delayed fluorescent material TD, may be equal to or less than about 0.3 eV in order to realize the delayed fluorescence (see, FIG. 3). In addition, each of the excited singlet energy level $S_1^H$ and the excited triplet energy level $T_1^H$ of the first compound as the host is higher than each of the excited singlet energy level $S_1^{TD}$ and the excited triplet energy level $T_1^{TD}$ of the second compound as the delayed fluorescent material TD, respectively. As an example, the excited triplet energy level $T_1^H$ of the first compound may be higher than the excited triplet energy level $T_1^{TD}$ of the second compound by at least about 0.2 eV, for example, at least about 0.3 eV, preferably at least about 0.5 eV.

Moreover, the excited triplet energy level $T_1^{TD}$ of the second compound is higher than an excited triplet energy level $T_1^{FD}$ of the third compound, which is the fluorescent or phosphorescent material FD. In one exemplary aspect, the excited singlet energy level $S_1^{TD}$ of the second compound may be higher than an excited singlet energy level $S_1^{FD}$ of the third compound.

In addition, the energy level bandgap (|HOMO$^H$-HOMO$^{TD}$|) between the HOMO energy level (HOMO$^H$) of the first compound as the host and the HOMO energy level (HOMO$^{TD}$) of the second compound as the delayed fluorescent material, or the energy level bandgap (|LUMO$^H$-LUMO$^{TD}$|) between the LUMO energy level (LUMO$^H$) of the first compound and the LUMO energy level (LUMO$^{TD}$) of the second compound may be equal to or less than about 0.5 eV.

For example, the first compound which can be the host may include any organic compound having the structure of Chemical Formulae 1 to 4. The second compound which can be the delayed fluorescent material TD may comprise the organic compound having the structure of Chemical Formula 5.

For example, the second compound as the blue-emitting delayed fluorescent material may comprise SPXZPO, DPXZPO, TPXZPO, DcZTrz, DDczTrz, DMTDAc, DMOC-DPS, DMAC-DPS, DMAC-TRZ, ACRSA, Cz-VPN, TcZTrz, mPTC, CC2BP, BDPCC-TPTA, BCC-TPTA, DPCC-TPTA, Phen-TRZ, Cab-Ph-TRZ, SpiroAC-TRZ, 3CzFCN and 4CzFCN. The second compound as the green-emitting delayed fluorescent material may comprise oPTC, PIC-TRZ, TmCzTrz, 2PXZ-OXD, DMAC-BP, TXO-PhCz, 4CzIPN, 4CzPN, 4CzFCN, 33TczPN, BFCz-2CN, BTCz-2CN, Ac-VPN, Px-VPN, 35IPNDcz, 26IPNDcz, TcZTrZ and 32alCTRZ. The second compound as the red-emitting delayed fluorescent material may comprise mPx2BBP, 4CzTPN-Ph, PPZ-DPS, DHPZ-2BZT, DHPZ-2TRZ and TPA-DCPP.

The exciton energy should be effectively transferred from the second compound as the delayed fluorescent material to the third compound as the fluorescent or phosphorescent material in order to implement hyper-fluorescence. With regard to energy transfer efficiency from the delayed fluorescent material to the fluorescent or phosphorescent material, an overlap between a luminescence spectrum of the delayed fluorescent material and an absorption spectrum of the fluorescent or phosphorescent material can be considered. As an example, a fluorescent or phosphorescent material having the absorption spectrum with large overlapping area with the luminescence spectrum of the second compound having the delayed fluorescent property may be used as the third compound in order to transfer exciton energy efficiently from the second compound to the third compound.

The third compound may emit blue (B), green (G) or red (R) light. In one exemplary aspect, the fluorescent material as the third compound may emit blue light. In this case, the third compound may comprise, but is not limited to, pyrene-based compounds, anthracene-based compounds, fluoranthene-based compounds and boron-based compounds. For example, the third compound as the blue-emitting fluorescent material may comprise anyone having the following structure of Chemical Formula 6:

[Chemical Formula 6]

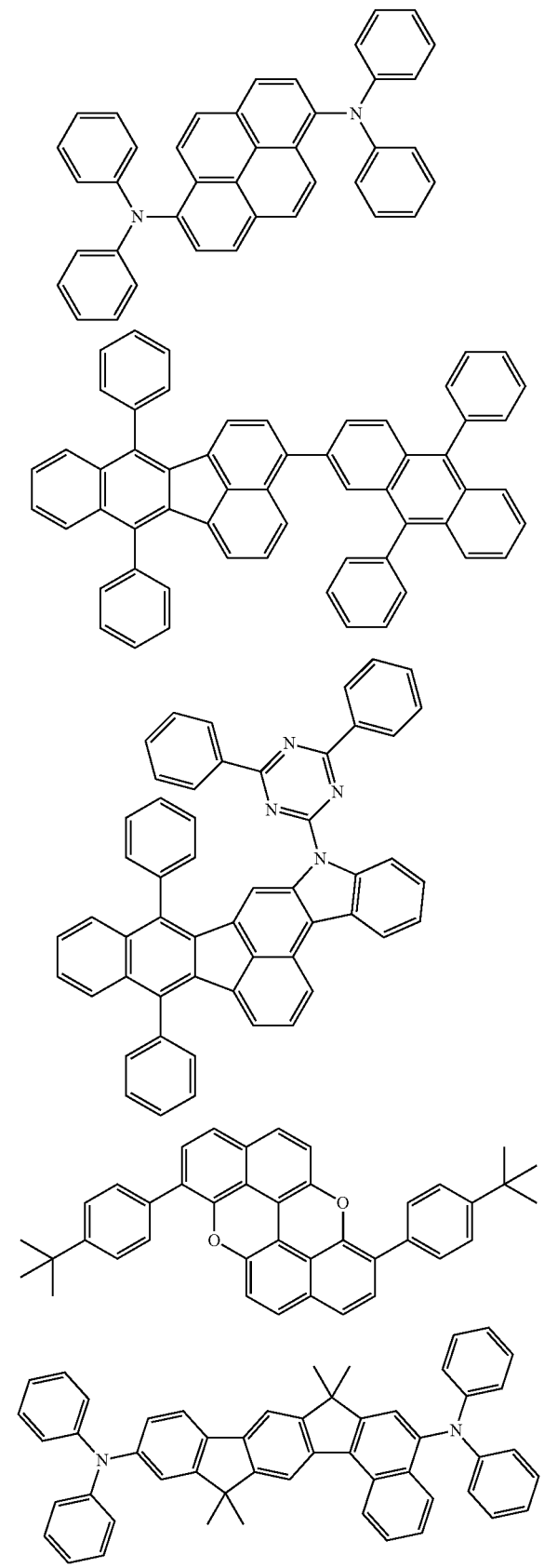

-continued

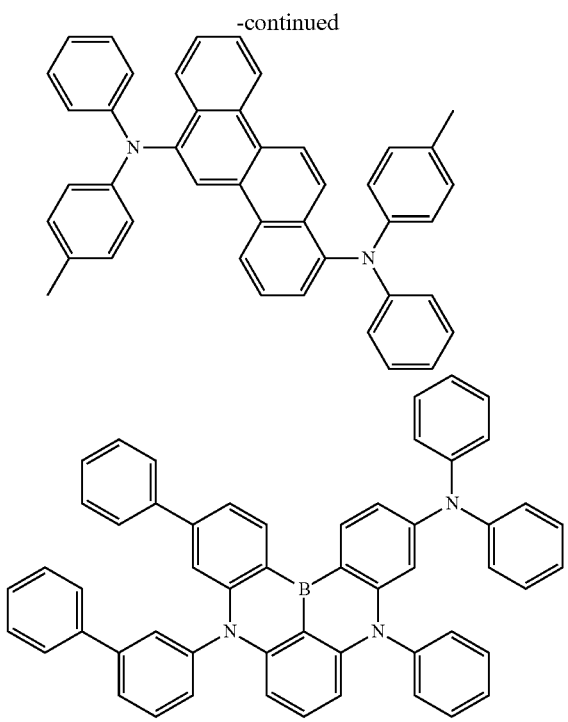

In an alternative aspect, the third compound as the green-emitting fluorescent material may have, but is not limited to, a boron-dipyrromethene (BODIPY; 4,4-difluoro-4-bora-3a,4a-diaza-s-indacene) core and/or a quinolino-acridine core. As an example, the fluorescent material FD may be selected from, but is not limited to, green fluorescent material having the BODIPY core (LGGD-FD1, LUMO: −3.5 eV; HOMO: −5.8 eV), green fluorescent material having the quinolino-acridine core such as 5,12-dimethylquinolino(2,3-b)acridine-7,14(5H, 12H)-dione (LUMO: −3.0 eV; HOMO: −5.4 eV), 5,12-diethylquinolino(2,3-b)acridine-7,14(5H, 12H)-dione (LUMO: −3.0 eV; HOMO: −5.4 eV), 5,12-dibutyl-3,10-difluoroquinolino(2,3-b)acridine-7,14(5H, 12H)-dione (LUMO: −3.1 eV; HOMO: −5.5 eV), 5,12-dibutyl-3,10-bis(trifluoromethyl)quinolino(2,3-b)acridine-7,14(5H, 12H)-dione (LUMO: −3.1 eV; HOMO: −5.5 eV), 1,1,7,7-tetramethyl-2,3,6,7-tetrahydro-1H,5H-benzo[ij]quinolizin-9-yl)ethenyl]-4H-pyran-4-ylidene}propanedinitrile (DCJTB; LUMO: −3.1 eV; HOMO: −5.3 eV), and combination thereof.

In one exemplary aspect, the contents of the first compound in the EML 240A may be larger than the contents of the second and third compounds. Also, the contents of the second compound may be larger than the contents of the third compound. For example, the contents of the first compound is larger than the contents of the second compound, and the contents of the second compound is larger than the contents of the third compound. In this case, exciton energy can be transferred efficiently from the second compound to the third compound via FRET mechanism. As an example, each of the contents of the first to third compounds in the EML 240A may be, but is not limited to, about 60 wt % to about 75 wt %, about 20 wt % to about 40 wt % and about 0.1 wt % to about 5 wt %, respectively.

When the bipolar organic compound having the structure of Chemical Formulae 1 to 4 is introduced in the EML 240A, holes and electrons are injected into the EML 240A in balance, the recombination zone is formed over the whole area of the EML 240A. The OLED D2 can be driven at a lower voltage, so that it can reduce its power consumption and improve its luminous efficiency and color purity.

Figure 7:
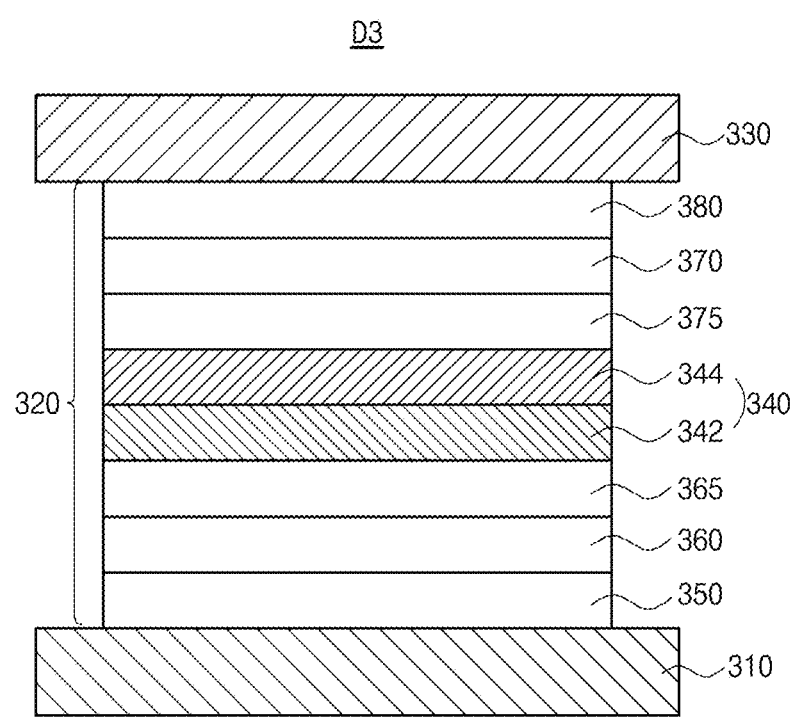
FIG. 7 is a schematic cross-sectional view illustrating an OLED in accordance with another exemplary aspect of the present disclosure.
Figure 8:
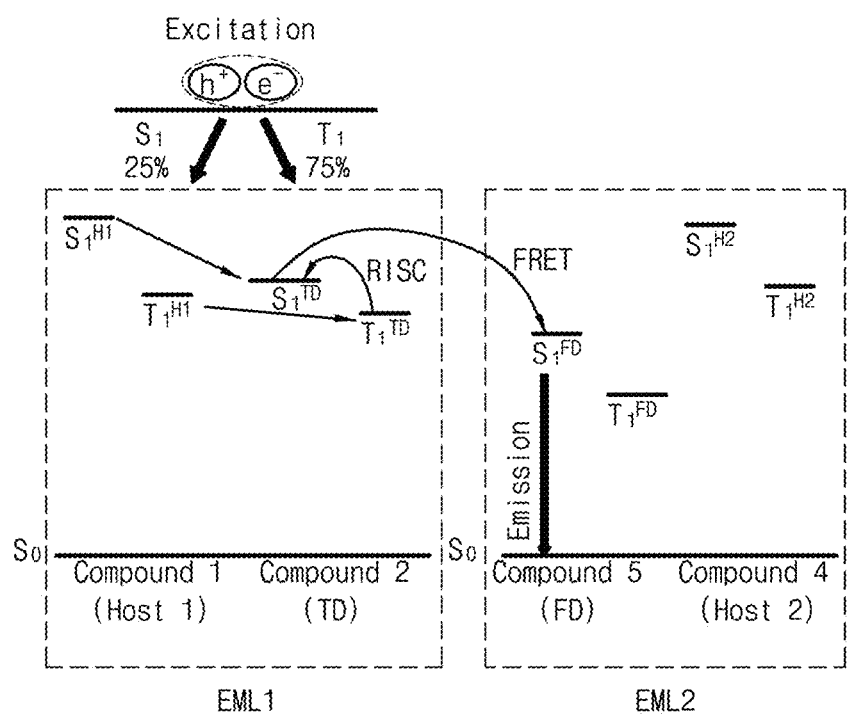
FIG. 8 is a schematic diagram illustrating luminous mechanism by energy level bandgap among luminous materials in accordance with another exemplary aspect of the present disclosure.

The OLEDs in accordance with the previous aspects have a single-layered EML. Alternatively, an OLED in accordance with the present disclosure may include multiple-layered EML. FIG. 7 is a schematic cross-sectional view illustrating an OLED having a double-layered EML in accordance with another exemplary aspect of the present disclosure. FIG. 8 is a schematic diagram illustrating luminous mechanism by energy level bandgap among luminous materials in accordance with another exemplary aspect of the present disclosure.

As illustrated in FIG. 7, the OLED D3 in accordance with an exemplary third aspect of the present disclosure includes first and second electrodes 310 and 330 facing each other and an emissive layer 320 having single emitting unit disposed between the first and second electrodes 310 and 330.

In one exemplary aspect, the emissive layer 320 comprises an EML 340. Also, the emissive layer 320 comprises an HIL 350 and an HTL 360 each of which is disposed sequentially between the first electrode 310 and the EML 340, and an ETL 370 and an EIL 380 each of which is disposed sequentially between the EML 340 and the second electrode 330. Alternatively, the emissive layer 320 may further comprise an EBL 365 disposed between the HTL 360 and the EML 340 and/or a HBL 375 disposed between the EML 340 and the ETL 370.

As described above, the first electrode 310 may be an anode and may include, but is not limited to, a conductive material having a relatively large work function values such as ITO, IZO, SnO, ZnO, ICO, AZO, and the like. The second electrode 330 may be a cathode and may include, but is not limited to, a conductive material having a relatively small work function values such as Al, Mg, Ca, Ag, alloy thereof or combination thereof.

The HIL 350 is disposed between the first electrode 310 and the HTL 360. The HIL 350 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 350 may be omitted in compliance with the structure of the OLED D3.

The HTL 360 is disposed adjacently to the EML 340 between the first electrode 310 and the EML 340. The HTL 360 may include, but is not limited to, TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 340 includes a first EML (EML1) 342 and a second EML (EML2) 344. The EML1 342 is disposed between the EBL 365 and the HBL 375 and the EML2 344 is disposed between the EML1 342 and the HBL 375. One of the EML1 342 and the EML2 344 includes a second compound (first dopant) that is the delayed fluorescent material, and the other of the EML1 342 and the EML2 344 includes a fifth compound (second dopant) that is the fluorescent or phosphorescent material. Also, each of the EML1 342 and the EML2 344 comprises the first compound (first host) and a fourth compound (second host), respectively. The configuration and energy levels among the luminous materials in the EML 340 will be explained in more detail below.

The ETL 370 is disposed between the EML 340 and the EIL 380. In one exemplary aspect, the ETL 370 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. As an example, the ETL 370 may include, but is not limited to, Alq$_3$, PBD, spiro-PBD, Liq, TPBi, BAlq, Bphen, NBphen, BCP, TAZ, NTAZ, TpPyPB, TmPPPyTz, PFNBr and/or TPQ. Alternatively, the ETL 370 may comprise anyone having the structure of Chemical Formulae 1 to 4. In this case, the ETL 370 may comprise only the organic compound having the structure of Chemical Formulae 1 to 4, or comprise the above-described electron transporting materials mixed or doped with the organic compound.

The EIL 380 is disposed between the second electrode 330 and the ETL 370. In one exemplary aspect, the EIL 380 may include, but is not limited to, an alkali halide such as LiF, CsF, NaF, BaF$_2$ and the like, and/or an organic metal compound such as lithium benzoate, sodium stearate, and the like.

The EBL 365 is disposed between the HTL 360 and the EML 340 for controlling and preventing electron transportations between the HTL 360 and the EML 340. As an example, The EBL 365 may include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB, DCDPA and/or 2,8-bis(9-phenyl-9H-carbazol-3-yl)dibenzo[b,d]thiophene.

The HBL 375 is disposed between the EML 340 and the ETL 370 for preventing hole transportations between the EML 340 and the ETL 370. In one exemplary aspect, the HBL 375 may include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 375 may include a compound having a relatively low HOMO energy level compared to the emitting material in EML 340. The HBL 375 may include, but is not limited to, BCP, BAlq, Alq$_3$, PBD, spiro-PBD, Liq, B3PYMPM, DPEPO, 9-(6-(9H-carbazol-9-yl)pyridine-3-yl)-9H-3,9'-bicarbazole, TSPO1 and combination thereof.

Alternatively, the HBL 375 may comprise anyone having the structure of Chemical Formulae 1 to 4. In this case, the HBL 375 may comprise only the organic compound having the structure of Chemical Formulae 1 to 4, or comprise the above-described hole blocking materials mixed or doped with the organic compound.

In the exemplary third aspect, the EML1 342 includes the first compound that may be the first host and the second compound that may be the delayed fluorescent material. The EML2 344 includes the fourth compound that may be the second host and the fifth compound that may be the fluorescent or phosphorescent material.

More particularly, the EML1 342 includes the first compound that is any organic compound having the structure of Chemical Formulae 1 to 4, and the second compound that is the delayed fluorescent material. The energy level bandgap ($\Delta E_{ST}^{TD}$) between the excited singlet energy level $S_1^{TD}$ and the excited triplet energy level $T_1^{TD}$ of the second compound in the EML1 342 is equal to or less than about 0.3 eV (see, FIG. 3) so that triplet exciton energy of the second compound can be transferred to its own singlet exciton energy via RISC mechanism. While the second compound has high internal quantum efficiency, but it has poor color purity due to its wide FWHM (full-width half maximum).

On the contrary, the EML2 344 may include the fourth compound that may be the second host and the fifth compound that is the fluorescent or phosphorescent material. While the fifth compound as the fluorescent material has an advantage in terms of color purity due to its narrow FWHM, but its internal quantum efficiency is low because its triplet exciton cannot be involved in the luminescence process.

However, in this exemplary aspect, the singlet exciton energy and the triplet exciton energy of the second compound having the delayed fluorescent property in the EML1 342 can be transferred to the fifth compound, which may be the fluorescent or phosphorescent material, in the EML2 344 disposed adjacently to the EML1 342 by FRET mechanism, which transfers energy non-radially through electrical fields by dipole-dipole interactions. Accordingly, the ultimate light emission occurs in the fifth compound within the EML2 344.

In other words, the triplet exciton energy of the second compound is converted upwardly to its own singlet exciton energy in the EML1 342 by RISC mechanism. Then, the converted singlet exciton energy of the second compound is transferred to the singlet exciton energy of the fifth compound in the EML2 344 because the second compound has the excited singlet energy level $S_1^{TD}$ higher than the excited singlet energy level Sm of the fifth compound (See, FIG. 8). The fifth compound in the EML2 344 can emit light using the triplet exciton energy as well as the singlet exciton energy.

As the exciton energy which is generated at the second compound having the delayed fluorescent property in the EML1 342 is efficiently transferred from the second compound to the fifth compound that is the fluorescent or phosphorescent material in the EML2 344, a hyper-fluorescence can be realized. In this case, while the second compound only acts as transferring exciton energy to the fifth compound, substantial light emission is occurred in the EML2 344 including the fifth compound which is the fluorescent or phosphorescent material and has a narrow FWHM. Accordingly, the OLED D3 can enhance its quantum efficiency and improve its color purity due to narrow FWHM.

The EML1 342 and the EML2 344 include the first compound as the first host and the fourth compound as the second host, respectively. The exciton energies generated at the first and fourth compounds should be transferred to the second compound as the delayed fluorescent material to emit light.

As illustrated in FIG. 8, each of excited singlet energy levels $S_1^{H1}$ and $S_1^{H2}$ and excited triplet energy levels $T_1^{H1}$ and $T_1^{H2}$ of the first and fourth compounds should be higher than each of the excited singlet energy level $S_1^{TD}$ and the excited triplet energy level $T_1^{TD}$ of the second compound as the delayed fluorescent material, respectively.

For example, when each of the excited triplet energy levels $T_1^{H1}$ and $T_1^{H2}$ of the first and fourth compounds is not high enough than the excited triplet energy level $T_1^{TD}$ of the second compound, the triplet exciton of the second compound may be reversely transferred to the excited state triplet energy levels $T_1^{H1}$ and $T_1^{H2}$ of the first and fourth compounds, each of which cannot utilize triplet exciton energy. Accordingly, the excitons of the triplet energy level $T_1^{TD}$ of the second compound may be quenched as a non-radiative recombination and the triplet state excitons of the second compound cannot be involved in the emission. As an example, each of the excited triplet energy levels $T_1^{H1}$ and $T_1^{H2}$ of the first and fourth compounds may be higher than the excited triplet energy level $T_1^{TD}$ of the second compound by at least about 0.2 eV, for example at least about 0.3 eV, preferably at least about 0.5 eV.

The excited singlet energy level $S_1^{H2}$ of the fourth compound is higher than the excited singlet energy level $S_1^{FD}$ of the fifth compound. In this case, the singlet exciton energy generated at the fourth compound can be transferred to the excited singlet energy level $S_1^{FD}$ of the fifth compound. Optionally, the excited triplet energy level $T_1^{H2}$ of the fourth compound may be higher than the excited triplet energy level $T_1^{FD}$ of the fifth compound.

In addition, it is necessary for the EML 340 to implement high luminous efficiency and color purity as well as to transfer exciton energy efficiently from the second compound, which is converted to ICT complex state by RISC mechanism in the EML1 342, to the fifth compound which is the fluorescent or phosphorescent material in the EML2 344. In order to realize such an OLED D3, the excited triplet energy level $T_1^{TD}$ of the second compound is higher than the excited triplet energy level $T_1^{FD}$ of the fifth compound. Optionally, the excited singlet energy level $S_1^{TD}$ of the second compound may be higher than the excited singlet energy level $S_1^{FD}$ of the fifth compound.

Moreover, the energy level bandgap ($|HOMO^H-HOMO^{TD}|$) between the HOMO energy level ($HOMO^H$) of the first and/or fourth compounds and the HOMO energy level ($HOMO^{TD}$) of the second compound, or the energy level bandgap ($|LUMO^H-LUMO^{TD}|$) between a LUMO energy level ($LUMO^H$) of the first and/or fourth compounds and the LUMO energy level ($LUMO^{TD}$) of the second compound may be equal to or less than about 0.5 eV. When the luminous materials do not satisfy the required energy levels as described above, exciton energies are quenched at the second and fifth compounds or exciton energies cannot transferred efficiently from the first and fourth compounds to the second and fifth compounds, so that OLED D3 may have reduced quantum efficiency.

The first compound and the fourth compound as the hosts may be the same or different from each other. For example, each of the first compound and the fourth compound may independently include any organic compound having the structure of Chemical Formulae 1 to 4. The second compound having the delayed fluorescent property may comprise anyone having the structure of Chemical Formula 5.

For example, the second compound as the blue-emitting delayed fluorescent material may comprise SPXZPO, DPXZPO, TPXZPO, DczTrz, DDczTrz, DMTDAc, DMOC-DPS, DMAC-DPS, DMAC-TRZ, ACRSA, Cz-VPN, TcZTrz, mPTC, CC2BP, BDPCC-TPTA, BCC-TPTA, DPCC-TPTA, Phen-TRZ, Cab-Ph-TRZ, SpiroAC-TRZ, 3CzFCN and 4CzFCN. The second compound as the green-emitting delayed fluorescent material may comprise oPTC, PIC-TRZ, TmCzTrz, 2PXZ-OXD, DMAC-BP, TXO-PhCz, 4CzIPN, 4CzPN, 4CzFCN, 33TczPN, BFCz-2CN, BTCz-2CN, Ac-VPN, Px-VPN, 35IPNDcz, 26IPNDcz, TcZTrZ and 32alCTRZ. The second compound as the red-emitting delayed fluorescent material may comprise mPx2BBP, 4CzTPN-Ph, PPZ-DPS, DHPZ-2BZT, DHPZ-2TRZ and TPA-DCPP.

The fifth compound may have a narrow FWHM and have an absorption spectrum with large overlapping area with a luminescence spectrum of the second compound. The fifth compound may be the fluorescent or phosphorescent material emitting blue, green or red light. For example, the fifth compound may comprise the blue-emitting fluorescent material that is anyone having the structure of Chemical Formula 6. Alternatively, the fifth compound may comprise the green-emitting fluorescent material having the BODIPY core and/or the quinolino-acridine-core, or the metal complex emitting blue, green or red light.

In one exemplary embodiment, the contents of the first and fourth compounds in the EML1 342 and the EML2 344 may be larger than or equal to the contents of the second and fifth compounds in the same layer. Also, the contents of the second compound in the EML1 342 may be larger than the contents of the fifth compound in the EML2 344. In this case, exciton energy can be transferred efficiently from the second compound to the fifth compound via FRET mechanism. As an example, the contents of the second compound in the EML1 342 may be, but is not limited to, about 1 wt % to about 70 wt %, preferably about 10 wt % to about 50 wt %, and more preferably about 20 wt % to about 50 wt %. In addition, the contents of the fourth compound in the EML2 344 may be about 90 wt % to about 99 wt %, preferably 95 wt % to about 99 wt %, and the contents of the fifth compound in the EML2 344 may be about 1 wt % to about 10 wt %, preferably about 1 wt % to about 5 wt %. Each of the EML1 342 and the EML2 344 may have a thickness of, but is not limited to, about 5 nm to about 100 nm, preferably about 10 nm to about 30 nm, and more preferably about 10 nm to about 20 nm.

When the EML2 344 is disposed adjacently to the HBL 375 in one exemplary aspect, the fourth compound, which is included in the EML2 344 together with the fifth compound, may be the same material as the HBL 375. In this case, the EML2 344 may have a hole blocking function as well as an emission function. In other words, the EML2 344 can act as a buffer layer for blocking holes. In one aspect, the HBL 375 may be omitted where the EML2 344 may be a hole blocking layer as well as an emitting material layer.

When the EML2 344 is disposed adjacently to the EBL 365 in another exemplary aspect, the fourth compound may be the same material as the EBL 365. In this case, the EML2 344 may have an electron blocking function as well as an emission function. In other words, the EML2 344 can act as a buffer layer for blocking electrons. In one aspect, the EBL 365 may be omitted where the EML2 344 may be an electron blocking layer as well as an emitting material layer.

When the bipolar organic compound having the structure of Chemical Formulae 1 to 4 is introduced in the EML 340, holes and electrons are injected into the EML 340 in balance, the recombination zone is formed over the whole area of the EML 340. The OLED D3 can be driven at a lower voltage, so that it can reduce its power consumption and improve its luminous efficiency and color purity.

Figure 9:
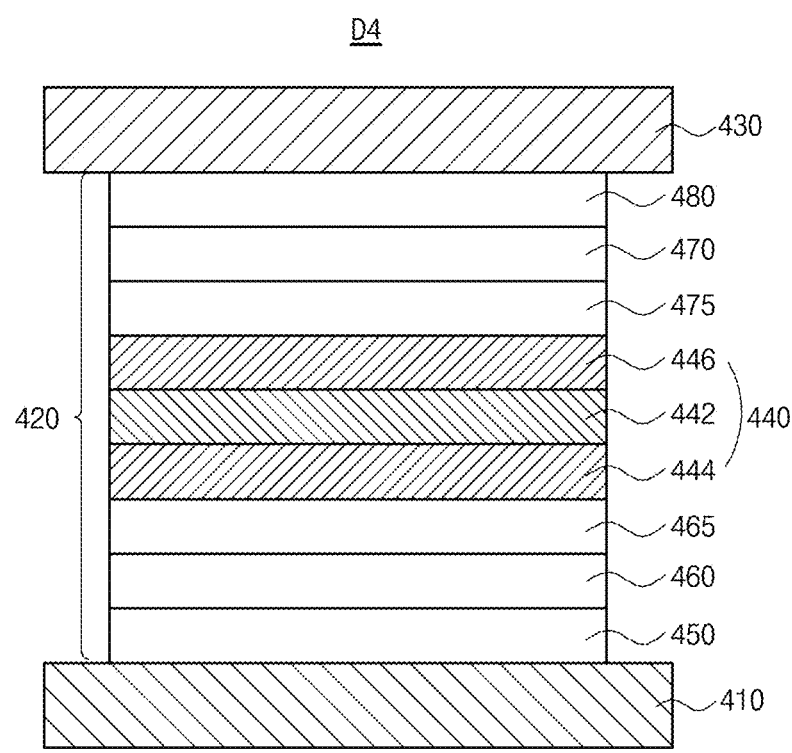
FIG. 9 is a schematic cross-sectional view illustrating an OLED in accordance with another exemplary aspect of the present disclosure.
Figure 10:
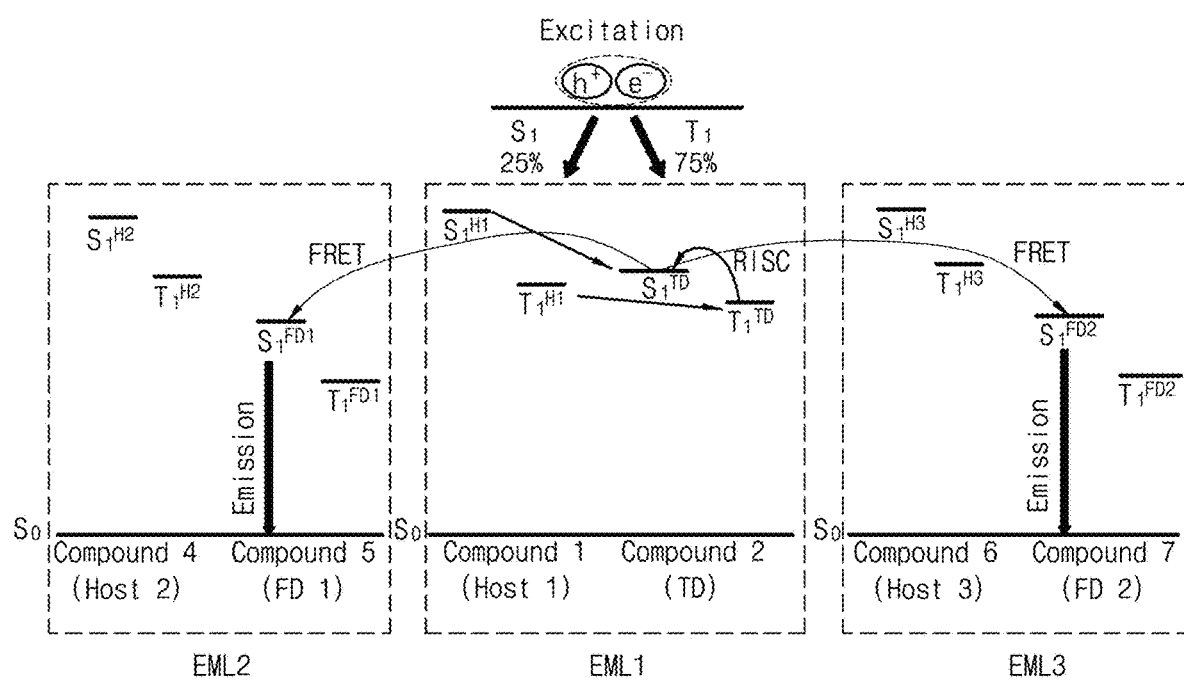
FIG. 10 is a schematic diagram illustrating luminous mechanism by energy level bandgap among luminous materials in accordance with another exemplary aspect of the present disclosure.

An OLED having a triple-layered EML will be explained. FIG. 9 is a schematic cross-sectional view illustrating an OLED having a triple-layered EML in accordance with another exemplary aspect of the present disclosure. FIG. 10 is a schematic diagram illustrating luminous mechanism by energy level bandgap among luminous materials in accordance with another exemplary aspect of the present disclosure.

As illustrated in FIG. 9, an OLED D4 in accordance with the fourth aspect of the present disclosure comprises first and second electrodes 410 and 430 facing each other and an emissive layer 420 disposed between the first and second electrodes 410 and 430.

In one exemplary aspect, the emissive layer 420 having single emitting unit comprises a three-layered EML 440. The emissive layer 420 comprises an HIL 450 and an HTL 460 each of which is disposed sequentially between the first electrode 410 and the EML 440, and an ETL 470 and an EIL 480 each of which is disposed sequentially between the EML 440 and the second electrode 430. Alternatively, the emissive layer 420 may further comprise an EBL 465 disposed between the HTL 460 and the EML 440 and/or a HBL 475 disposed between the EML 440 and the ETL 470. The configurations of the first and second electrodes 410 and 430 as well as other layers except the EML 440 in the emissive layer 420 is substantially identical to the corresponding electrodes and layers in the OLEDs D1, D2 and D3.

The EML 440 comprises a first EML (EML1) 442, a second EML (EML2) 444 and a third EML (EML3) 446. The EML1 442 is disposed between the EBL 465 and the HBL 475, the EML2 444 is disposed between the EBL 465 and the EML1 442 and the EML3 446 is disposed between the EML1 442 and the HBL 475.

The EML1 442 comprises the second compound (first dopant) that may be the delayed fluorescent material. Each of the EML2 444 and the EML3 446 comprises the fifth compound (second dopant) and a seventh compound (third dopant) each of which may be the fluorescent or phosphorescent material, respectively. In addition, the EML1 442, EML2 444 and EML3 446 further includes the first, fourth and sixth compounds each of which may be the first to third hosts, respectively.

In accordance with this aspect, the singlet energy as well as the triplet energy of the second compound, i.e. the delayed fluorescent material in the EML1 442 can be transferred to the fifth and seventh compounds, i.e. the fluorescent or phosphorescent materials each of which is included in the EML2 444 and EML3 446 disposed adjacently to the EML1 442 by FRET mechanism. Accordingly, the ultimate emission occurs in the fifth and seventh compounds in the EML2 444 and the EML3 446.

In other words, the triplet exciton energy of the second compound having the delayed fluorescent property in the EML1 442 is converted upwardly to its own singlet exciton energy by RISC mechanism, then the singlet exciton energy of the second compound is transferred to the singlet exciton energy of the fifth and seventh compounds in the EML2 444 and the EML3 446 because the second compound has the excited singlet energy level $S_1^{TD}$ higher than each of the excited singlet energy levels $S_1^{FD}1$ and $S_1^{FD}2$ of the fifth and seventh compounds (see, FIG. 10). The singlet exciton energy of the second compound in the EML1 442 is transferred to the fifth and seventh compounds in the EML2 444 and the EML3 446 which are disposed adjacently to the EML1 442 by FRET mechanism.

The fifth and seventh compounds in the EML2 444 and EML3 446 can emit light using the singlet exciton energy and the triplet exciton energy derived from the second compound. Each of the fifth and seventh compounds may have narrower FWHM compared to the second compound. As the exciton energy, which is generated at the second compound having the delayed fluorescent property in the EML1 442, is transferred to the fifth and seventh compounds in the EML2 444 and the EML3 446, a hyper-fluorescence can be realized. Particularly, each of the fifth and seventh compounds may have a luminescence spectrum having a large overlapping area with an absorption spectrum of the second compound, so that exciton energy of the second compound may be transferred efficiently to each of the fifth and seventh compounds. In this case, substantial light emission is occurred in the EML2 444 and in the EML3 446.

To implement efficient luminescence in the EML 440, it is necessary to adjust properly energy levels among luminous materials in the EML1 442, the EML2 444 and the EML3 446. As illustrated in FIG. 10, each of excited singlet energy levels $S_1^{H1}$, $S_1^{H2}$ and $S_1^{H3}$ and excited triplet energy levels $T_1^{H1}$, $T_1^{H2}$ and $T_1^{H3}$ of the first, fourth and sixth compounds, each of which may be the first to third hosts, respectively, should be higher than each of the excited singlet energy level $S_1^{TD}$ and the excited triplet energy level $T_1^{TD}$ of the second compound that may be the delayed fluorescent material, respectively.

For example, when each of the excited triplet energy levels $T_1^{H1}$, $T_1^{H2}$ and $T_1^{H3}$ of the first, fourth and sixth compounds is not high enough than the excited triplet energy level $T_1^{TD}$ of the second compound, the triplet exciton of the second compound may be reversely transferred to the excited triplet energy levels $T_1^{H1}$, $T_1^{H2}$ and $T_1^{H3}$ of the first, fourth and sixth compounds, each of which cannot utilize triplet exciton energy. Accordingly, the excitons of the triplet energy level $T_1^{TD}$ of the second compound may be quenched as a non-radiative recombination and the triplet state excitons of the second compound cannot be involved in the luminescence.

In addition, it is necessary for the EML 440 to implement high luminous efficiency and color purity as well as to transfer exciton energy efficiently from the second compound, which is converted to ICT complex state by RISC mechanism in the EML1 442, to the fifth and seventh compounds each of which is the fluorescent or phosphorescent material in the EML2 444 and the EML3 446. In order to realize such an OLED D4, the excited triplet energy level $T_1^{TD}$ of the second compound in the EML1 442 is higher than each of excited triplet energy levels $T_1^{FD}1$ and $T_1^{FD}2$ of the fifth and seventh compounds. Alternatively, the excited singlet energy level $S_1^{TD}$ of the second compound may be higher than each of excited singlet energy levels $S_1^{FD}1$ and $S_1^{FD}2$ of the fifth and seventh compounds as fluorescent material.

Moreover, the exciton energy, which is transferred from the second compound to each of the fifth and seventh compounds, should not be transferred to the fourth and sixth compounds in order to realize efficient light emission. As an example, each of the excited singlet energy levels $S_1^{H2}$ and $S_1^{H3}$ of the fourth and sixth compounds may be higher than each of the excited singlet energy levels $S_1^{FD}1$ and $S_1^{FD}2$ of the fifth and seventh compounds, respectively. In one exemplary aspect, the energy level bandgap between the excited singlet energy level $S_1^{TD}$ and the excited triplet energy level $T_1^{TD}$ of the second compound may be equal to or less than about 0.3 eV in order to implement a delayed fluorescence.

In addition, the energy level bandgap ($|HOMO^H-HOMO^{TD}|$) between the HOMO energy levels ($HOMO^H$) of the first, fourth and sixth compounds each of which may be the first to third hosts, respectively, and the HOMO energy level ($HOMO^{TD}$) of the second compound, or the energy level bandgap ($|LUMO^H-LUMO^{TD}|$) between the LUMO energy level ($LUMO^H$) of the first, fourth and sixth compounds and the LUMO energy level ($LUMO^{TD}$) of the second compound may be equal to or less than about 0.5 eV.

Each of the EML1 442, the EML2 444 and the EML3 446 may include the first, fourth and sixth compounds each of which may be the first to third hosts, respectively. For example, each of the first, fourth and sixth compounds may be the same or different from each other. For Example, each of the first, fourth and sixth compounds may independently include any organic compound having the structure of Chemical Formulae 1 to 4. The second compound having the delayed fluorescent property may comprise anyone having the structure of Chemical Formula 5.

For example, the second compound as the blue-emitting delayed fluorescent material may comprise SPXZPO, DPXZPO, TPXZPO, DcZTrz, DDcZTrz, DMTDAc, DMOC-DPS, DMAC-DPS, DMAC-TRZ, ACRSA, Cz-VPN, TcZTrz, mPTC, CC2BP, BDPCC-TPTA, BCC-TPTA, DPCC-TPTA, Phen-TRZ, Cab-Ph-TRZ, SpiroAC-TRZ, 3CzFCN and 4CzFCN. The second compound as the green-emitting delayed fluorescent material may comprise oPTC, PIC-TRZ, TmCzTrz, 2PXZ-OXD, DMAC-BP, TXO-PhCz, 4CzIPN, 4CzPN, 4CzFCN, 33TczPN, BFCz-2CN, BTCz-2CN, Ac-VPN, Px-VPN, 35IPNDcz, 26IPNDcz, TcZTrZ and 32alCTRZ. The second compound as the red-emitting delayed fluorescent material may comprise mPx2BBP, 4CzTPN-Ph, PPZ-DPS, DHPZ-2BZT, DHPZ-2TRZ and TPA-DCPP.

Each of the fifth and seventh compounds may have a narrow FWHM and have an absorption spectrum with large overlapping area with a luminescence spectrum of the second compound. Each of the fifth and seventh compounds may the fluorescent or phosphorescent material emitting blue, green or red light. For example, each of the fifth and seventh compounds may comprise the blue-emitting fluorescent material that is anyone having the structure of Chemical Formula 6. Alternatively, each of the fifth and seventh compounds may comprise the green-emitting fluorescent material having the BODIPY core and/or the quinolino-acridine core, or the metal complex emitting blue, green or red light.

In one exemplary aspect, each of the contents of the fourth and sixth compounds in the EML2 444 and the EML3 446 may be larger than or equal to each of the contents of the fifth and seventh compounds in the same layer. Also, the contents of the second compound in the EML1 442 may be larger than each of the contents of the fifth and seventh compounds in the EML2 444 and in the EML3 446. In this case, exciton energy can be transferred efficiently from the second compound to the fifth and seventh compounds via FRET mechanism. As an example, the contents of the second compound in the EML1 442 may be, but is not limited to, about 1 wt % to about 70 wt %, preferably about 10 wt % to about 50 wt %, and more preferably about 20 wt % to about 50 wt %. In addition, each of the contents of the fourth and sixth compounds in the EML2 444 and in the EML3 446 may be about 90 wt % to about 99 wt %, preferably 95 wt % to about 99 wt %, and each of the contents of the fifth and seventh compounds in the EML2 444 and in the EML3 446 may be about 1 wt % to about 10 wt %, preferably about 1 wt % to about 5 wt %. The EML1 442 may have a thickness of, but is not limited to, about 2 nm to about 100 nm, preferably about 2 nm to about 30 nm, and more preferably about 2 nm to about 20 nm. Also, each of the EML2 444 and the EML3 446 may have a thickness of, but is not limited to, about 5 nm to about 100 nm, preferably about 10 nm to about 30 nm, and more preferably about 10 nm to about 20 nm.

When the EML2 444 is disposed adjacently to the EBL 465 in one exemplary aspect, the fourth compound, which is included in the EML2 444 together with the fifth compound, may be the same material as the EBL 465. In this case, the EML2 444 may have an electron blocking function as well as an emission function. In other words, the EML2 444 can act as a buffer layer for blocking electrons. In one aspect, the EBL 465 may be omitted where the EML2 444 may be an electron blocking layer as well as an emitting material layer.

When the EML3 446 is disposed adjacently to the HBL 475 in another exemplary aspect, the sixth compound, which is included in the EML3 446 together with the seventh compound, may be the same material as the HBL 475. In this case, the EML3 446 may have a hole blocking function as well as an emission function. In other words, the EML3 446 can act as a buffer layer for blocking holes. In one aspect, the HBL 475 may be omitted where the EML3 446 may be a hole blocking layer as well as an emitting material layer.

In still another exemplary aspect, the fourth compound in the EML2 444 may be the same material as the EBL 455 and the sixth compound in the EML3 446 may be the same material as the HBL 475. In this aspect, the EML2 444 may have an electron blocking function as well as an emission function, and the EML3 446 may have a hole blocking function as well as an emission function. In other words, each of the EML2 444 and the EML3 446 can act as a buffer layer for blocking electrons or hole, respectively. In one aspect, the EBL 465 and the HBL 475 may be omitted where the EML2 444 may be an electron blocking layer as well as an emitting material layer and the EML3 446 may be a hole blocking layer as well as an emitting material layer.

When the bipolar organic compound having the structure of Chemical Formulae 1 to 4 is introduced in the EML 440, holes and electrons are injected into the EML 440 in balance, the recombination zone is formed over the whole area of the EML 440. The OLED D4 can be driven at a lower voltage, so that it can reduce its power consumption and improve its luminous efficiency and color purity.

Figure 11:
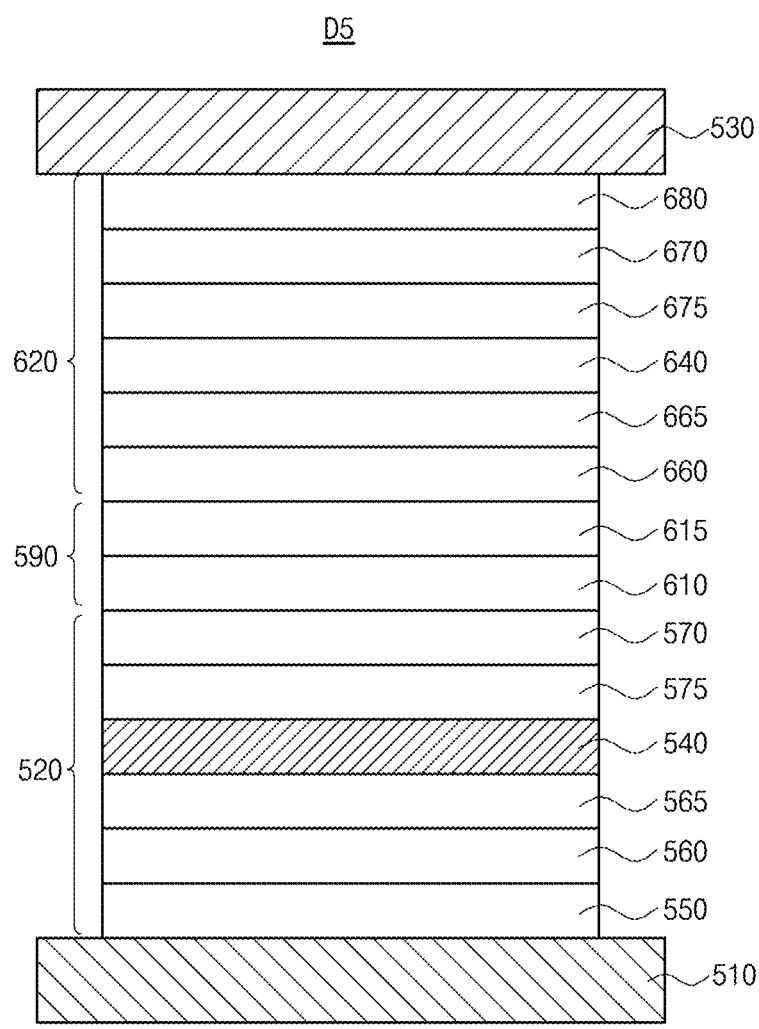
FIG. 11 is a schematic cross-sectional view illustrating an OLED in accordance with another exemplary aspect of the present disclosure.

In the above aspects, the OLEDs having only one emitting unit are described. Unlike the above aspects, the OLED may have multiple emitting units so as to form a tandem structure. FIG. 11 is a cross-sectional view illustrating an OLED in accordance with still another aspect of the present disclosure.

As illustrated in FIG. 11, the OLED D5 in accordance with the fifth aspect of the present disclosure comprises first and second electrodes 510 and 530 facing each other, a first emitting unit 520 disposed between the first and second electrodes 510 and 530, a second emitting unit 620 disposed between the first emitting unit 520 and the second electrode 530, and a charge generation layer (CGL) 590 disposed between the first and second emitting units 520 and 620.

The first electrode 510 may be an anode and include, but is not limited to, a conductive material having a relatively large work function values. As an example, the first electrode 510 may include, but is not limited to, ITO, IZO, SnO, ZnO, ICO, AZO, and the like. The second electrode 530 may be a cathode and may include, but is not limited to, a conductive material having a relatively small work function values such as Al, Mg, Ca, Ag, alloy thereof or combination thereof. Each of the first and second electrodes 510 and 530 may be laminated with a thickness of, but is not limited to, about 30 nm to about 300 nm.

The first emitting unit 520 comprises a lower EML 540. Also, the first emitting unit comprises a HIL 550 and a first HTL (HTL1) 560 each of which is disposed sequentially between the first electrode 510 and the lower EML 540, a first ETL (ETL1) 570 disposed between the lower EML 540 and the CGL 590. Alternatively, the first emitting unit 520 may further comprise a first EBL (EBL1) 565 disposed between the HTL1 560 and the lower EML 540 and/or a first HBL (HBL1) 575 disposed between the lower EML 540 and the ETL1 570.

The second emitting unit 620 comprises an upper EML 640. The second emitting unit 620 comprises a second HTL (HTL2) 660 disposed between the CGL 590 and the upper EML 640, and a second ETL (ETL2) 670 and an EIL 680 each of which is disposed sequentially between the upper EML 640 and the second electrode 530. Alternatively, the second emitting unit 620 may further comprise a second EBL (EBL2) 665 disposed between the HTL2 660 and the upper EML 640 and/or a second HBL (HBL2) 675 disposed between the upper EML 640 and the ETL2 670.

At least one of the lower EML 540 and the upper EML 640 may comprise any organic compound having the structure of Chemical Formulae 1 to 4 and emit anyone of blue (B), green (G) and red (R), and the other of the lower EML 540 and the upper EML 640 emit other colors. For example, one of the lower EML 540 and the upper EML 640 may emit green (G) light and the other of the lower EML 540 and the upper EML 640 may emit red (R) and/or blue (B) light. Hereinafter, the OLED D5, where the lower EML 540 emits green light and the upper EML 640 emits blue and/or red light, will be explained.

The HIL 550 is disposed between the first electrode 510 and the HTL1 560 and improves an interface property between the inorganic first electrode 510 and the organic HTL1 560. In one exemplary aspect, the HIL 550 may comprise, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 550 may be omitted in compliance with a structure of the OLED D5.

Each of the HTL1 560 and the HTL2 660 may independently include, but is not limited to, TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

Each of the ETL1 570 and the ETL2 670 facilitates electron transportations in the first emitting unit 520 and the second emitting unit 620, respectively. Each of the ETL1 570 and the ETL2 670 may independently include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like, respectively. As an example, each of the ETL1 570 and the ETL2 670 may independently include, but is not limited to, $Alq_3$, PBD, spiro-PBD, Liq, TPBi, BAlq, Bphen, NBphen, BCP, TAZ, NTAZ, TpPyPB, TmPP-PyTz, PFNBr and/or TPQ, respectively.

Alternatively, at least one of the ETL1 570 and the ETL2 670 may comprise anyone having the structure of Chemical Formulae 1 to 4. In this case, the at least one of the ETL1 570 and the ETL2 670 may comprise only the organic compound having the structure of Chemical Formulae 1 to 4, or comprise the above-described electron transporting materials mixed or doped with the organic compound.

The EIL 680 is disposed between the second electrode 530 and the second ETL 670, and can improve physical properties of the second electrode 530 and therefore, can enhance the lifetime of the OLED D5. In one exemplary aspect, the EIL 580 may include, but is not limited to, an alkali halide such as LiF, CsF, NaF, $BaF_2$ and the like, and/or an organic metal compound such as lithium benzoate, sodium stearate, and the like.

Each of the EBL1 565 and the EBL2 665 may independently include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD), TDAPB and/or 3,6-bis(N-carbazolyl)-N-phenyl-carbazole, respectively.

Each of the HBL1 575 and the HBL2 675 may independently include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, each of the HBL1 575 and the HBL2 675 may independently include, but is not limited to, BCP, BAlq, $Alq_3$, PBD, spiro-PBD, Liq, B3PYMPM, DPEPO, 9-(6-(9H-carbazol-9-yl)pyridine-3-yl)-9H-3,9'-bicarbazole and combination thereof, respectively.

Alternatively, at least one of the HBL1 575 and the HBL2 675 may comprise anyone having the structure of Chemical Formulae 1 to 4. In this case, the at least one of the HBL1 575 and the HBL2 675 may comprise only the organic compound having the structure of Chemical Formulae 1 to 4, or comprise the above-described electron transporting materials mixed or doped with the organic compound.

In one exemplary aspect, when the upper EML 640 emits blue light, the upper EML 640 may emit deep blue or sky blue light. In this case, the upper EML 640 may comprise a blue host and a blue dopant. For example, the blue host may comprise, but is not limited to, mCP, mCP-CN, mCBP, CBP-CN, 9-(3-(9H-Carbazol-9-yl)phenyl)-3-(diphenylphosphoryl)-9H-carbazole (mCPPO1), 3,5-Di(9H-carbazol-9-yl)biphenyl (Ph-mCP), TSPO1, 9-(3'-(9H-carbazol-9-yl)-[1,1'-biphenyl]-3-yl)-9H-pyrido[2,3-b]indole (CzBPCb), Bis(2-methylphenyl)diphenylsilane (UGH-1), 1,4-Bis(triphenylsilyl)benzene (UGH-2), 1,3-Bis(triphenylsilyl)benzene (UGH-3), 9,9-Spirobifluoren-2-yl-diphenylphosphine oxide (SPPO1), 9,9'-(5-(Triphenylsilyl)-1,3-phenylene)bis(9H-carbazole) (SimCP), and the like.

The blue dopant may comprise, but is not limited to, perylene, 4,4'-Bis[4-(di-p-tolylamino)styryl]biphenyl (DPAVBi), 4-(Di-p-tolylamino)-4-4'-[(di-p-tolylamino)styryl]stilbene (DPAVB), 4,4'-Bis[4-(diphenylamino)styryl]biphenyl (BDAVBi), 2,5,8,11-Tetra-tetr-butylperylene (TBPe), Bis(2-(2-hydroxyphenyl)pyridinato)beryllium (Bepp2), 9-(9-Phenylcarbazole-3-yl)-10-(naphthalene-1-yl)anthracene (PCAN), mer-Tris(1-phenyl-3-methylimidazolin-2-ylidene-C,C(2)'iridium(III) (mer-Ir(pmi)3), fac-Tris(1,3-diphenyl-benzimidazolin-2-ylidene-C,C(2)'iridium(III) (fac-Ir(dpbic)3), Bis(3,4,5-trifluoro-2-(2-pyridyl)phenyl-(2-carboxypyridyl)iridium(III) (Ir(tfpd)2pic), tris(2-(4,6-difluorophenyl)pyridine)iridium(III) (Ir(Fppy)3), Bis[2-(4,6-difluorophenyl)pyridinato-$C^2$,N](picolinato)iridium(III) (FIrpic), and the like. In this case, the upper EML 640 may emit blue having wavelength of about 450 nm to about 500 nm.

In an alternative aspect, when the upper EML 640 is the red EML, the upper EML 640 may contain a red host and a red dopant. The red host may comprise, but is not limited to, 9,9'-Diphenyl-9H,9'H-3,3'-bicarbazole (BCzPh), CBP, 1,3,5-Tris(carbazole-9-yl)benzene (TCP), TCTA, 4,4'-Bis(carbazole-9-yl)-2,2'-dimethylbiphenyl (CDBP), 2,7-Bis(carbazole-9-yl)-9,9-dimethylfluorene (DMFL-CBP), 2,2',7,7'-Tetrakis(carbazole-9-yl)-9,9-spirofluorene (Spiro-CBP), DPEPO, 4'-(9H-carbazol-9-yl)biphenyl-3,5-dicarbonitrile (PCzB-2CN), 3'-(9H-carbazol-9-yl)biphenyl-3,5-dicarbonitrile (mCzB-2CN), 3,6-Bis(carbazole-9-yl)-9-(2-ethylhexyl)-9H-carbazole (TCzl), Bepp2, Bis(10-hydroxybenzo[h] quinolinato)beryllium (Bebg2), 1,3,5-Tris(1-pyrenyl)benzene (TPB3), and the like.

The red dopant may comprise, but is not limited to, [Bis(2-(4,6-dimethyl)phenylquinoline)](2,2,6,6-tetramethylheptane-3,5-dionate)iridium(III), Bis[2-(4-n-hexylphenyl) quinoline](acetylacetonate)iridium(III) (Hex-Ir(phq)2 (acac)), Tris[2-(4-n-hexylphenyl)quinoline]iridium(III) (Hex-Ir(phq)3), Tris[2-phenyl-4-methylquinoline]iridium (III) (Ir(Mphq)3), Bis(2-phenylquinoline)(2,2,6,6-tetramethylheptane-3,5-dionate)iridium(III) (Ir(dpm)PQ2), Bis(phenylisoquinoline)(2,2,6,6-tetramethylheptane-3,5-dionate)iridium(III) (Ir(dpm)(piq)2), Bis[(4-n-hexylphenyl)isoquinoline](acetylacetonate)iridium(III) (Hex-Ir(piq)2 (acac)), Tris[2-(4-n-hexylphenyl)quinoline]iridium(III) (Hex-Ir(piq)3), Tris(2-(3-methylphenyl)-7-methyl-quinolato)iridium (Ir(dmpq)3), Bis[2-(2-methylphenyl)-7-methylquinoline](acetylacetonate)iridium(III) (Ir(dmpq)2(acac)), Bis[2-(3,5-dimethylphenyl)-4-methylquinoline](acetylacetonate)iridium(III) (Ir(mphmq)2(acac)), and the like. In this case, the upper EML 640 may emit red light having wavelength of about 600 nm to about 650 nm.

Alternatively, the second emitting unit may comprise two emitting material layers, for example, blue and red emitting material layers in order to enhance the red efficiency of the OLED D5. In this case, the second emitting unit 620 may emit light having wavelength of about 451 nm to about 650 nm.

The CGL 590 is disposed between the first emitting unit 520 and the second emitting unit 620. The CGL 590 includes an N-type CGL 610 disposed adjacently to the first emitting unit 520 and a P-type CGL 615 disposed adjacently to the second emitting unit 620. The N-type CGL 610 injects electrons into the first emitting unit 520 and the P-type CGL 615 injects holes into the second emitting unit 620.

As an example, the N-type CGL 610 may be an organic layer doped with an alkali metal such as Li, Na, K and/or Cs and/or an alkaline earth metal such as Mg, Sr, Ba and/or Ra. For example, a host used in the N-type CGL 610 may include, but is not limited to, an organic compound such as Bphen or MTDATA. The alkali metal or the alkaline earth metal may be doped with about 0.01 wt % to about 30 wt %.

Alternatively, the N-type CGL 610 may comprise any organic compound having the structure of Chemical Formulae 1 to 4. As described above, any organic compound having the structure of Chemical Formulae 1 to 4 has high affinity to electrons. In this case, the N-type CGL 610 may comprise only the organic compound having the structure of Chemical Formulae 1 to 4, or further comprise the alkali metal or the alkaline earth metal doped with the organic compound.

The P-type CGL 615 may include, but is not limited to, an inorganic material selected from the group consisting of tungsten oxide (WOx), molybdenum oxide (MoOx), beryllium oxide ($Be_2O_3$), vanadium oxide ($V_2O_5$) and combination thereof, and/or an organic material selected from the group consisting of NPD, HAT-CN, 2,3,5,6-Tetrafluoro-7,7,8,8-tetracyanoquinodimethane (F4TCNQ), TPD, N,N,N',N'-Tetranaphthalenyl-benzidine (TNB), TCTA, N,N'-dioctyl-3,4,9,10-perylenedicarboximide (PTCDI-C8) and combination thereof.

The lower EML 540 comprises the first compound that can be the host and the second compound that can be the dopant such as the delayed fluorescent material. The first compound may comprise any organic compound having the structure of Chemical Formulae 1 to 4. The second compound emitting green light may comprise oPTC, PIC-TRZ, TmCzTrz, 2PXZ-OXD, DMAC-BP, TXO-PhCz, 4CzIPN, 4CzPN, 4CzFCN, 33TczPN, BFCz-2CN, BTCz-2CN, Ac-VPN, Px-VPN, 35IPNDcz, 26IPNDcz, TcZTrZ, 32aICTRZ, and the like.

Similar to the first aspect, the singlet exciton energy generated at the first compound that may be the host can be transferred to the singlet exciton of the second compound that may be the delayed fluorescent material in the lower EML 540. Each of the excited singlet energy level $S_1^{H1}$ and the excited triplet energy level $T_1^{H1}$ of the first compound is higher than each of the excited singlet energy level $S_1^{TD}$ and the excited triplet energy level $T_1^{TD}$ of the second compound having the delayed fluorescent property, respectively (see, FIG. 4). As an example, the excited triplet energy levels $T_1^{H1}$ of the first compound may be higher than the excited triplet energy level $T_1^{TD}$ of the second compound by at least about 0.2 eV, for example at least about 0.3 eV, preferably at least about 0.5 eV.

The lower EML 540 implements fluorescent emission as the singlet exciton energy transferred from the first compound to the second compound is shifted to the ground state. In addition, the lower EML 540 implements delayed fluorescent emission as the triplet exciton energy of the second compound is converted to its own singlet exciton energy by RISC mechanism, and then the converted singlet exciton energy is shifted to the ground state. Since the second compound emits light utilizing both the excited singlet exciton and the excited triplet exciton, the OLED D5 can enhance its luminous efficiency.

In addition, when any organic compound having the structure of Chemical Formulae 1 to 4 and having the bipolar property is introduced into the lower EML 540, the recombination zone among the electrons and holes are distributed uniformly over the whole area in the lower EML 540, thereby improving the luminous efficiency of the OLED D5. Moreover, when the organic compound is introduced into the lower EML 540, the OLED D5 can be driven at lower voltage, and thereby reducing the power consumption.

In this case, the contents of the second compound in the lower EML 540 may be about 1 wt % to about 70 wt %, preferably about 10 wt % to about 50 wt %, and more preferably about 20 wt % to about 50 wt %. The lower EML 540 may have a thickness of, but is not limited to, about 10 nm to about 200 nm, preferably about 20 to about 100 nm, and more preferably about 30 nm to about 50 nm.

In an alternative aspect, the lower EML 540 may comprise the first compound that may be the host, the second compound that may be the delayed fluorescent material, and the third compound that may be the fluorescent or phosphorescent material (see, FIG. 5). In another exemplary aspect, the lower EML 540 may have a double-layered structure that comprises an EML1 and an EML2. In this case, the EML1 may comprise the first compound that may be the first host and the second compound that may be the delayed fluorescent material while the EML2 may comprise the fourth compound that may be the second host and the fifth compound that may be the fluorescent or phosphorescent material (see, FIG. 7). In still another aspect, the lower EML 540 may have a triple-layered structure that further comprises an EML3 disposed oppositely to the EML2 with respect to the EML. In this case, the EML3 may comprise the sixth compound that may be the third host and the seventh compound that may be the fluorescent or phosphorescent material (see, FIG. 9).

In still another exemplary aspect, an OLED of the present disclosure may comprise three or more emitting units. For example, the OLED may further comprise a third emitting unit disposed between the second emitting unit 620 and the second electrode 530 and a second CGL disposed between the second emitting unit 620 and the third emitting unit.

Synthesis Example 1: Synthesis of Compound 1-20

(1) Synthesis of Intermediate a

[Reaction Formula 1-1]

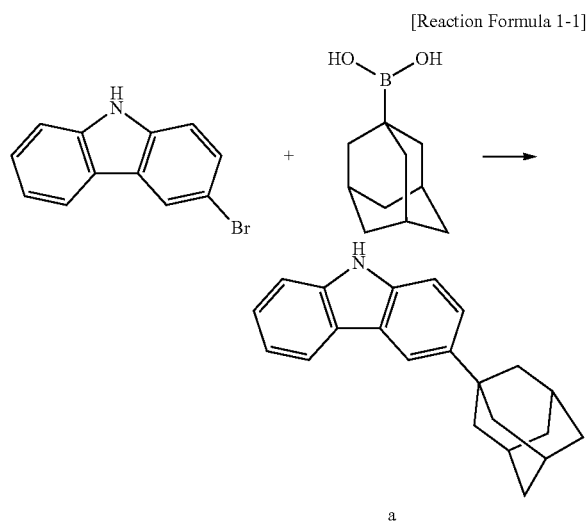

a 3.65 g (3 equivalents) of potassium carbonate dissolved in distilled water was added into a reaction vessel under nitrogen atmosphere and the solution was stirred. 1.64 g (1.2 equivalents) of 3-bromocarbazole, 1.00 g (1 equivalent) of adamantan-1-yl-boronic acid and THE (TIF: distilled water=3:1 by volume) were added into the reaction vessel and then the mixed solution was stirred. 0.51 g (0.05 equivalent) of tetrakis (triphenylphosphine)palladium(0) (Pd[P(C$_6$H$_5$)$_3$]$_4$) was added into the reaction vessel, the temperature of the solution was raised until reflux and the solution was stirred again. After reacting for 24 hours, the reaction vessel was cooled, and the crude product was extracted with ethyl acetate and distilled water. The moisture and solvent were removed using MgSO$_4$, and the crude product was separated and purified with column chromatography using hexane: ethyl acetate (3:1) as an eluent to give a white solid Intermediate a (yield=73%).

(2) Synthesis of Intermediate b

[Reaction Formula 1-2]

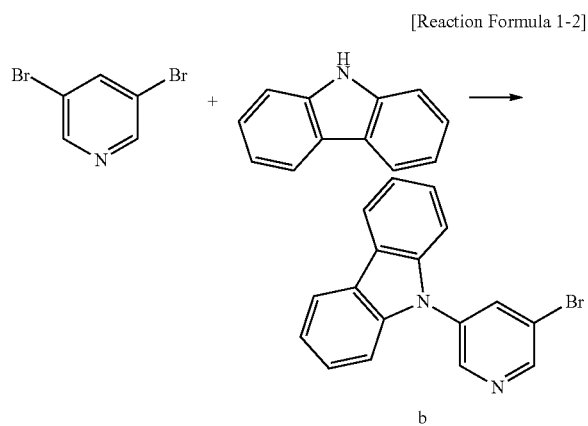

b 1.00 g (1 equivalent) of 3,5-dibromopyridine, 0.64 g (0.9 equivalent) of carbazole, 0.19 g (0.05 equivalent) of tris (dibenzylideneacetone)dipalladium(0) (Pd$_2$(dba)$_3$), 0.09 g (0.1 equivalent) of tri-tert-butylphosphine (P(t-Bu)$_3$) and 2.03 g (5 equivalents) of sodium tert-butoxide (NaOC(CH$_3$)$_3$) and 90 mL of toluene were added into an reaction vessel with stirring under nitrogen atmosphere. The solution was refluxed with stirring more than 18 hours to proceed with the reaction. After terminating the reaction, the reaction vessel was cooled down to a room temperature, the crude product was extracted with ethyl acetate and distilled water, and the moisture was removed using MgSO$_4$. The crude product was separated and purified by column chromatography using hexane:dichloromethane (2:3) as an eluent, and re-crystallized to give a white solid Intermediate b (yield=47%).

(3) Synthesis of Compound 1-20

[Reaction Formula 1-3]

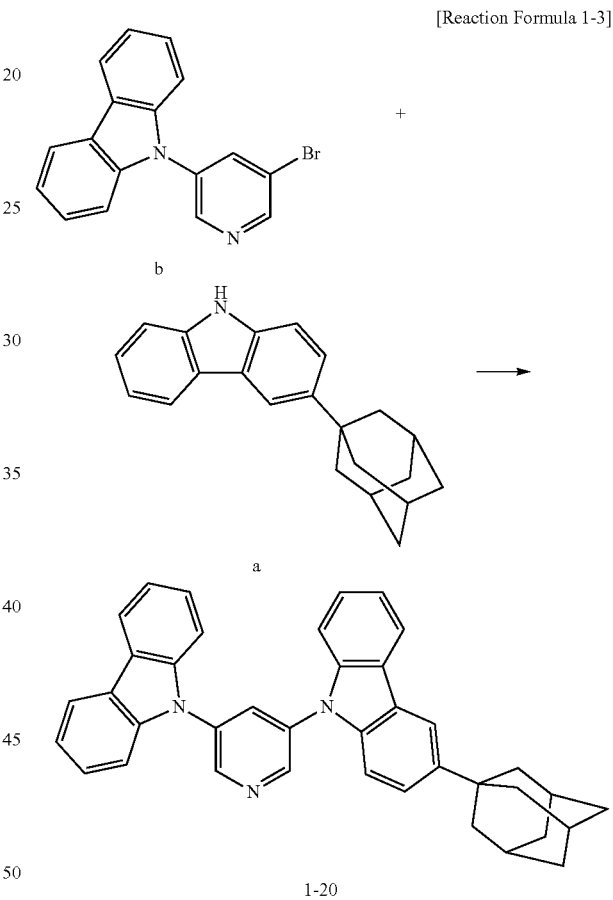

1-20

1.00 g (1 equivalent) of Intermediate b, 1.03 g (1.1 equivalents) of Intermediate a, 0.14 g (0.05 equivalent) of Pd$_2$(dba)$_3$, 0.06 g (0.1 equivalent) of (P(t-Bu)$_3$) and 1.49 g (5 equivalents) of NaOC(CH$_3$)3 and 50 mL of toluene were added into an reaction vessel with stirring under nitrogen atmosphere. The solution was refluxed with stirring more than 18 hours to proceed with the reaction. After terminating the reaction, the reaction vessel was cooled down to a room temperature, the crude product was extracted with ethyl acetate and distilled water, and the moisture was removed using MgSO$_4$. The crude product was separated and purified by column chromatography using hexane:dichloromethane (2:3) as an eluent, and re-crystallized to give a white solid Compound 1-20 (yield=61%).

Synthesis Example 2: Synthesis of Compound 2-1

[Reaction Formula 2]

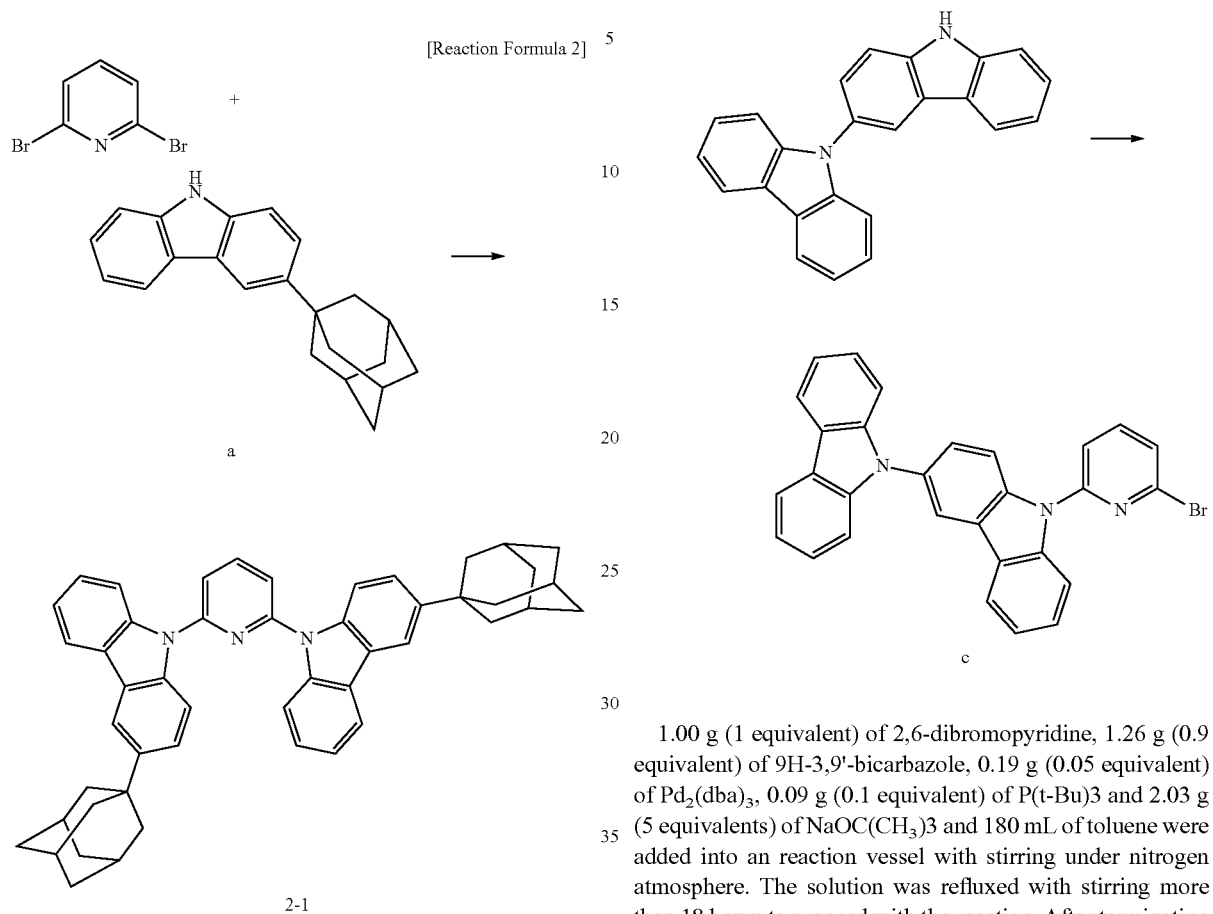

2-1

1.00 g (1 equivalent) of 2,6-dibromopyridine, 1.53 g (2.2 equivalents) of Intermediate a, 0.38 g (0.1 equivalent) of $Pd_2(dba)_3$, 0.18 g (0.2 equivalent) of $(P(t-Bu)_3)$ and 4.06 g (10 equivalents) of $NaOC(CH_3)3$ and 150 mL of toluene were added into an reaction vessel with stirring under nitrogen atmosphere. The solution was refluxed with stirring more than 18 hours to proceed with the reaction. After terminating the reaction, the reaction vessel was cooled down to a room temperature, the crude product was extracted with ethyl acetate and distilled water, and the moisture was removed using $MgSO_4$. The crude product was separated and purified by column chromatography using hexane:dichloromethane (2:3) as an eluent, and re-crystallized to give a white solid Compound 2-1 (yield=89%).

Synthesis Example 3: Synthesis of Compound 3-1

(1) Synthesis of Intermediate

[Reaction Formula 3-1]

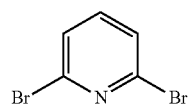 +

1.00 g (1 equivalent) of 2,6-dibromopyridine, 1.26 g (0.9 equivalent) of 9H-3,9'-bicarbazole, 0.19 g (0.05 equivalent) of $Pd_2(dba)_3$, 0.09 g (0.1 equivalent) of P(t-Bu)3 and 2.03 g (5 equivalents) of $NaOC(CH_3)3$ and 180 mL of toluene were added into an reaction vessel with stirring under nitrogen atmosphere. The solution was refluxed with stirring more than 18 hours to proceed with the reaction. After terminating the reaction, the reaction vessel was cooled down to a room temperature, the crude product was extracted with ethyl acetate and distilled water, and the moisture was removed using $MgSO_4$. The crude product was separated and purified by column chromatography using hexane:dichloromethane (1:1) as an eluent, and re-crystallized to give a white solid Intermediate c (yield=58%).

(2) Synthesis of Compound 3-1

[Reaction Formula 3-2]

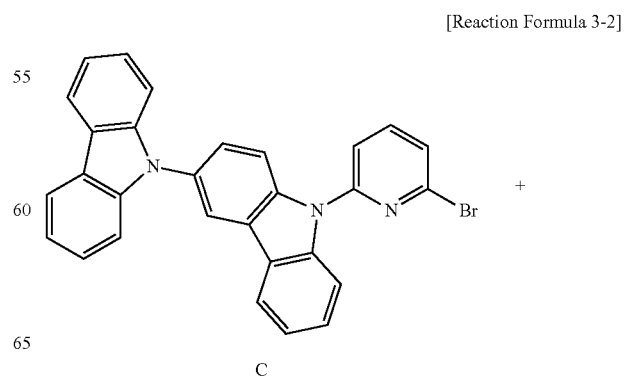

-continued

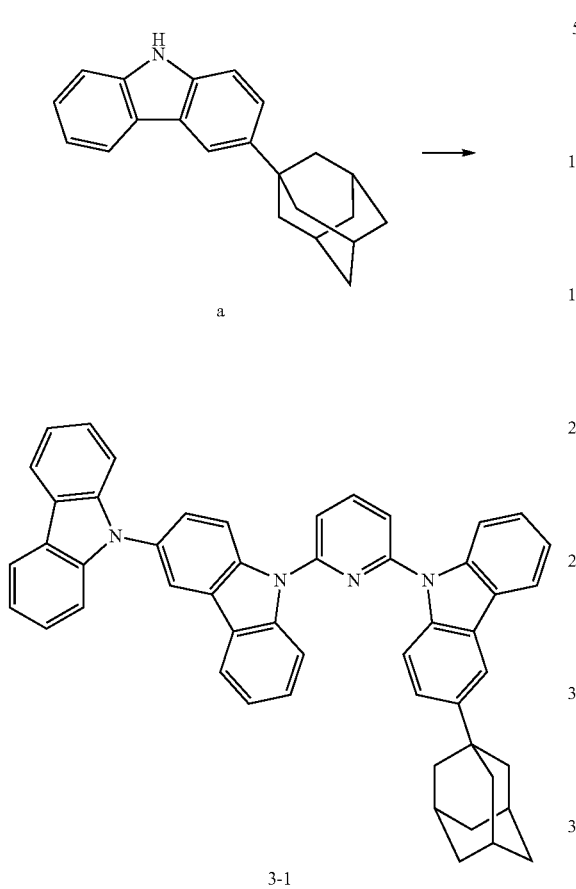

a 3-1

[Reference Compound]

Ref. 1

Ref. 2

TABLE 1

Energy Level of Compounds

| Compound | HOMO*(eV) | LUMO*(eV) | $T_1$* (eV) |
|---|---|---|---|
| 1-20 | −5.74 | −2.11 | 2.93 |
| 2-1 | −5.73 | −2.43 | 2.99 |
| 3-1 | −5.72 | −2.16 | 2.91 |
| 1-37 | −5.85 | −2.49 | 2.89 |
| Ref. 1 | −5.90 | −2.51 | 2.87 |
| Ref. 2 | −5.80 | −2.49 | 2.78 |

*HOMO, LUMO, $T_1$: calculation @ Schrodinger simulation 1.00 g (1 equivalent) of Intermediate c, 0.68 g (1.1 equivalents) of Intermediate a, 0.09 g (0.05 equivalent) of $Pd_2(dba)_3$, 0.04 g (0.1 equivalent) of $(P(t-Bu)_3)$ and 0.98 g (5 equivalents) of $NaOC(CH_3)3$ and 100 mL of toluene were added into an reaction vessel with stirring under nitrogen atmosphere. The solution was refluxed with stirring more than 18 hours to proceed with the reaction. After terminating the reaction, the reaction vessel was cooled down to a room temperature, the crude product was extracted with ethyl acetate and distilled water, and the moisture was removed using $MgSO_4$. The crude product was separated and purified by column chromatography using hexane: dichloromethane (1:1-2:3) as an eluent, and re-crystallized to give a white solid Compound 3-1 (yield=49%).

Experimental Example 1: Evaluation of Energy Level of Compound

Energy levels such as HOMO energy levels, LUMO energy levels, excited singlet energy levels $S_1$ and excited triplet energy levels $T_1$ for the Compounds 1-20, 2-1 and 3-1, each of which was synthesized in the above Synthesis Examples, and Compound 1-37 in Chemical Formula 2 as well as the reference compounds were evaluated with simulation. Table 1 below indicates the evaluation results.

As illustrated in Table 1, each of the compounds 1-20, 2-1, 3-1 and 1-37 had HOMO energy level, LUMO energy level and excited triplet energy level that are adequate for using an emissive layer. Particularly, each of the compounds synthesized in the Synthesis Examples had very high excited triplet energy level which is adequate for the host in the EML, or materials of ETL and/or HBL. In addition, we confirmed that the synthesized compounds have higher excited triplet energy level higher than the Ref. 1 and Ref 2 compounds.

Example 1 (Ex. 1): Fabrication of OLED

An OLED in which the Compound 1-20 is applied as a host of an EML was fabricated. An ITO (50 nm) attached glass substrate with 40 nm×40 nm×0.5 nm was ultrasonically cleaned with isopropyl alcohol, acetone and distilled water for 5 minutes and then dried in an oven at 100° C. The cleaned substrate was treated with $O_2$ plasma in a vacuum for 2 minutes and transferred to a deposition chamber in order to deposit other layers on the substrate. An organic layer was deposited by evaporation by a heated boat under $10^{-7}$ torr in the following order. The deposition rate of the organic layer was set to 1 Å/s.

A HIL (HAT-CN; 50 Å); a HTL (NPB, 500 Å); an EBL (mCP; 100 Å); an EML (Compound 1 (host): green delayed fluorescent material 4CzIPN=70:30 by weight; 300 Å); an ETL (TPBi; 300 Å); an EIL (LiF; 10 Å); and a cathode (Al; 1000 Å).

And then, cappling layer (CPL) was deposited over the cathode and the device was encapsulated by glass. After deposition of emissive layer and the cathode, the OLED was transferred from the deposition chamber to a dry box for film formation, followed by encapsulation using UV-curable epoxy resin and moisture getter. The manufacture organic light emitting diode had an emission area of 9 mm$^2$.

Examples 2-3 (Ex. 2-3): Fabrication of OLED

An OLED was fabricated using the same materials as Example 1, except that Compound 2-1 (Ex. 2) or the Compound 3-1 (Ex. 3) was applied into the host of the EML instead of the Compound 1-20.

Comparative Examples 1-2 (Com. 1-2): Fabrication of OLED

An OLED was fabricated using the same materials as Example 1, except that Ref. Compound 1Com. 1) or the Ref. Compound 2 (Com. 2) was applied into the host of the EML instead of the Compound 1-20.

Experimental Example 2: Measurement of Luminous Properties of OLED

Each of the OLED fabricated by Ex. 1-3 and Com. 1-2 was connected to an external power source and then luminous properties for all the diodes were evaluated using a constant current source (KEITHLEY) and a photometer PR650 at room temperature. In particular, driving voltage (V), maximum electroluminescence wavelength (EL $\lambda_{max}$, nm), External Quantum Efficiency (EQE, %) at a current density of 6.3 mA/cm$^2$ and a relative time period until luminescence is reduced to 95% level of the initial luminance (lifetime, T95) relative to Com. 2 at a current density of 12.7 J (6.3 mA/cm$^2$) were measured. The results thereof are shown in the following Table 2.

TABLE 1

Luminous Properties of OLED

| Sample | Host | V | EL $\lambda_{max}$ | EQE | T$_{95}$ |
|---|---|---|---|---|---|
| Com. 1 | Ref. 1 | 4.21 | 532 | 16.55 | 238 |
| Com. 2 | Ref. 2 | 4.31 | 536 | 13.24 | 100 |
| Ex. 1 | 1-20 | 4.18 | 538 | 16.68 | 475 |
| Ex. 2 | 2-1 | 4.10 | 538 | 18.79 | 1063 |
| Ex. 3 | 3-1 | 4.18 | 538 | 16.73 | 425 |

As indicated in Table 2, compared to the OLED in Com. 1 in which Ref. Compound 1 comprising a pyridine moiety and two carbazolyl moieties was applied into the host of the EML, the OLEDs in Ex. 1-3 in which organic compounds having at least one adamantyl group were applied into the host of the EML lowered their driving voltages a little bit and enhanced their EQE and luminous lifetime up to 13.5% and 3.47 times, respectively. Also, compared to the OLED in Com. 2 in which Ref. Compound 2, which further comprises four phenyl rings to the Ref. Compound 1, was applied into the host of the EML, the OLEDs in Ex. 1-3 in which organic compounds having at least one adamantyl group were applied into the host of the EML lowered their driving voltages up to 4.9% and enhanced their EQE and luminous lifetime up to 41.9% and 10.63 times, respectively. Consequently, we confirmed that the OLED in which applied the organic compound of the present disclosure can lower its driving voltage as well as improve its luminous efficiency and luminous lifetime. Accordingly, it is possible to implement an organic light emitting device having lowered driving voltage and improved luminous efficiency by using the OLED applying the organic compound.

It will be apparent to those skilled in the art that various modifications and variations can be made in the present disclosure without departing from the scope of the invention. Thus, it is intended that the present disclosure cover the modifications and variations of the present disclosure provided they come within the scope of the appended claims.

What is claimed is:

1. An organic light emitting diode, comprising:
a first electrode;
a second electrode facing the first electrode; and
at least one emitting unit disposed between the first and second electrodes,
wherein the at least one emitting unit comprises a host consisting of an organic compound having the following structure of Chemical Formula 1:

[Chemical Formula 1]

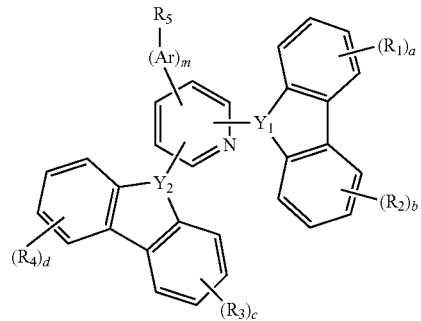

wherein:
each of $R_1$ to $R_4$ is independently selected from the group consisting of protium, deuterium, tritium, $C_1$-$C_{20}$ alkyl and an adamantyl group;
$R_5$ is selected from the group consisting of protium, deuterium, tritium, $C_1$-$C_{20}$ alkyl and an adamantyl group;
at least one of $R_1$ to $R_5$ is the adamantyl group;
each of a, b, c, d is the number of substituent and is independently an integer of 0 to 4;
Ar is $C_6$-$C_{30}$ arylene or $C_3$-$C_{30}$ hetero arylene;
m is an integer of 0 or 1;
each of $Y_1$ and $Y_2$ is N; and
the organic compound incudes at least one adamantyl group.

2. The organic light emitting diode of claim 1, wherein one or two of $R_1$ to $R_5$ is the adamantyl group, wherein each of $R_1$ to $R_5$ other than the adamantyl group is selected from the group consisting of protium, deuterium, tritium, and $C_1$-$C_{20}$ alkyl.

3. The organic light emitting diode of claim 1, wherein the at least one emitting unit comprises at least one electron transport layer disposed between the first and second electrodes and wherein the at least one electron transport layer comprises the organic compound.

4. The organic light emitting diode of claim 1, wherein the at least one emitting unit comprises at least one hole blocking layer disposed between the first and second electrodes and wherein the at least one hole blocking layer comprises the organic compound.

5. The organic light emitting diode of claim 1, wherein the at least one emitting unit comprises a first emitting material layer disposed between the first and second electrodes and wherein the first emitting material layer comprises the organic compound.

6. The organic light emitting diode of claim 5, wherein the first emitting material layer comprises a first compound and a second compound and wherein the first compound comprises the organic compound.

7. The organic light emitting diode of claim 6, wherein the first emitting material layer further comprises a third compound.

8. The organic light emitting diode of claim 6, wherein the at least one emitting unit further comprises a second emitting material layer disposed between the first electrode and the first emitting material layer or between the first emitting material layer and the second electrode, wherein the second emitting material layer comprises a fourth compound and a fifth compound, and wherein the fourth compound comprises the organic compound.

9. The organic light emitting diode of claim 8, wherein the at least one emitting unit further comprises a third emitting material layer disposed oppositely to the second emitting material layer with respect to the first emitting material layer, wherein the third emitting material layer comprises a sixth compound and a seventh compound, and wherein the fourth compound and the sixth compound comprise the organic compound.

10. The organic light emitting diode of claim 5, wherein the at least one emitting unit comprises a first emitting unit disposed between the first and second electrodes, and a second emitting unit disposed between the first emitting unit and the second electrode,
wherein the first emitting unit comprises a lower emitting material layer and the second emitting unit comprises an upper emitting material layer,
wherein at least one of the lower emitting material layer and the upper emitting material layer comprises the organic compound, and
further comprises a charge generation layer disposed between the first emitting unit and the second emitting unit.

11. An organic light emitting device, comprising:
a substrate; and
an organic light emitting diode of claim 1 disposed over the substrate.

12. The organic light emitting diode of claim 1, wherein the organic compound is selected from:

1-1

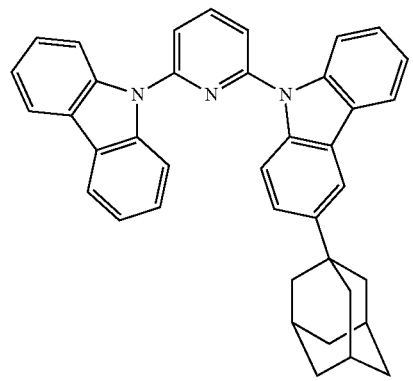

-continued 1-2

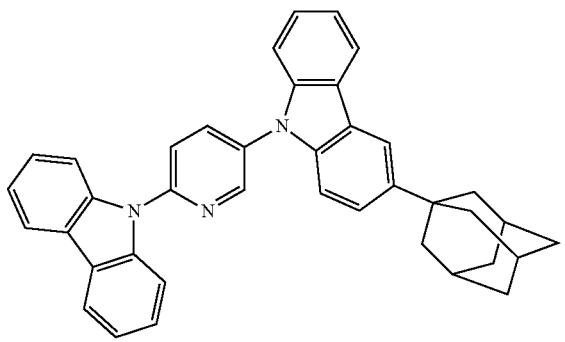

1-3

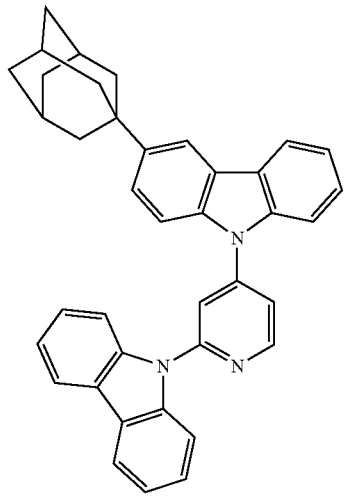

1-4

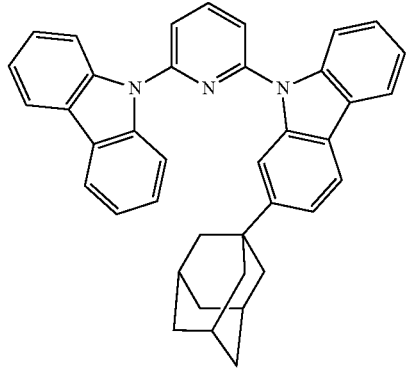

1-5

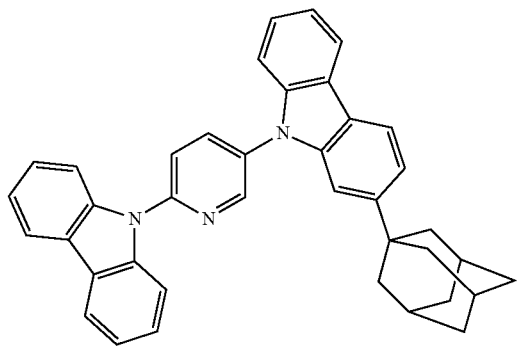

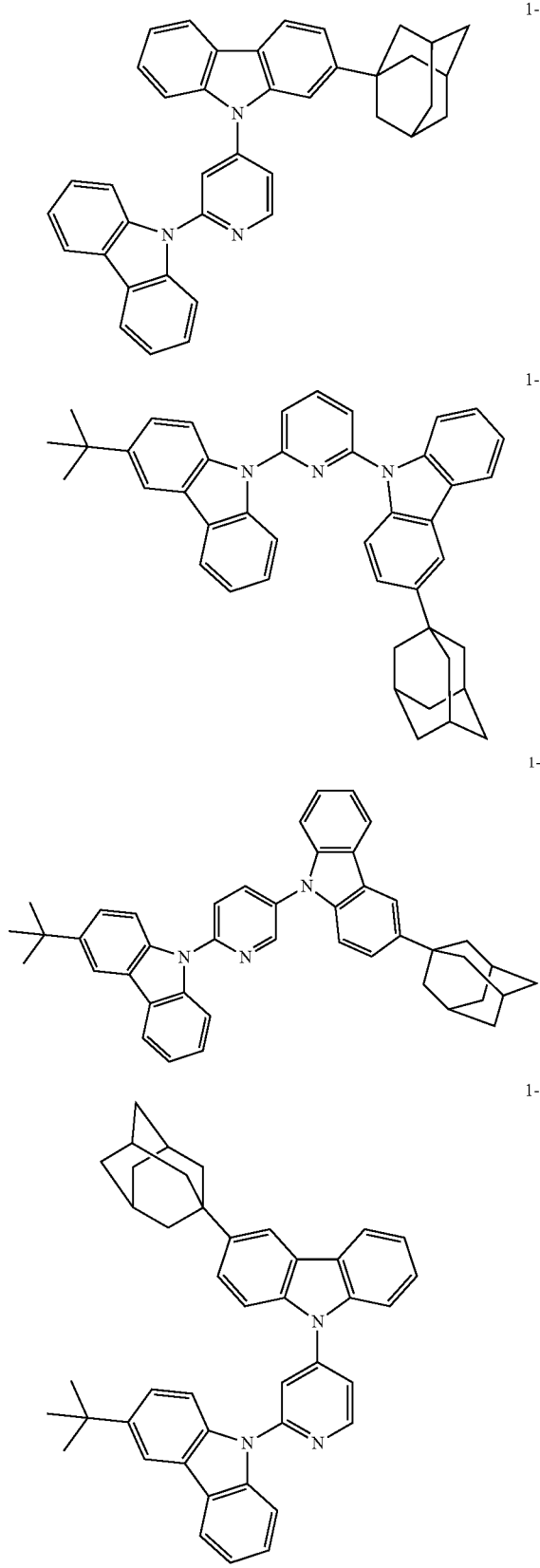
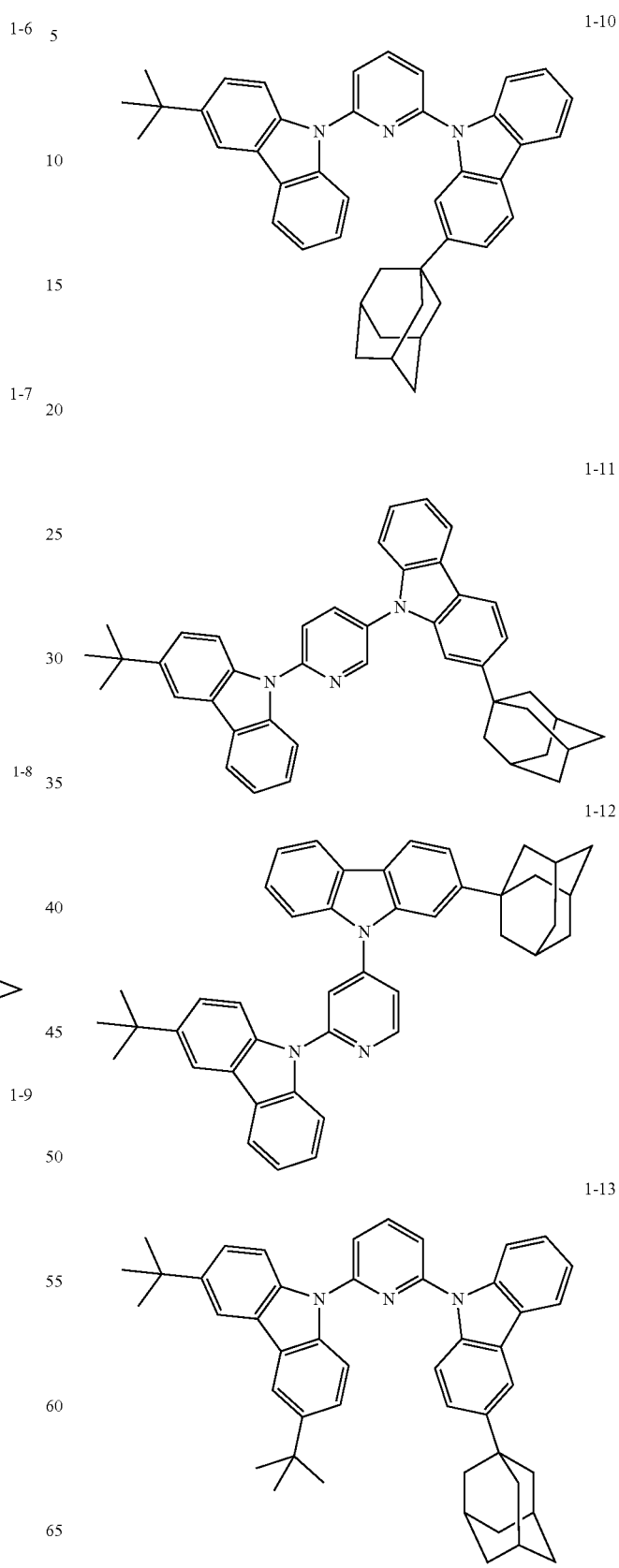

1-14
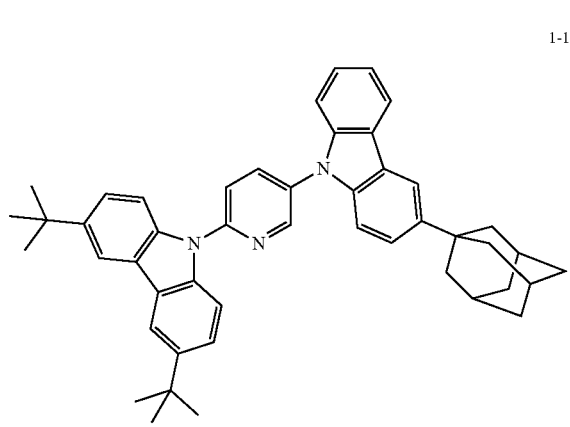
1-17
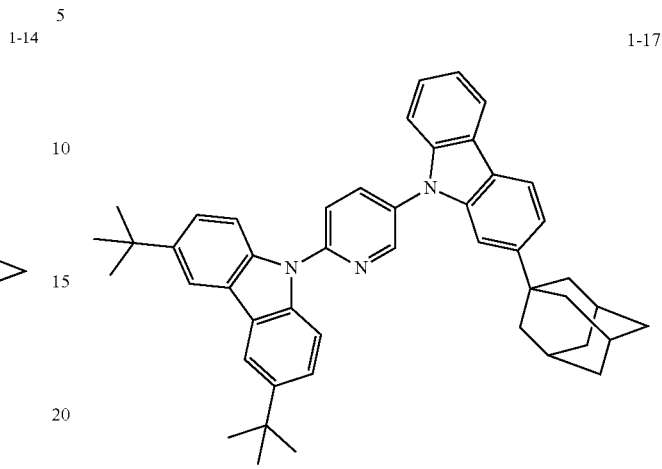
1-15
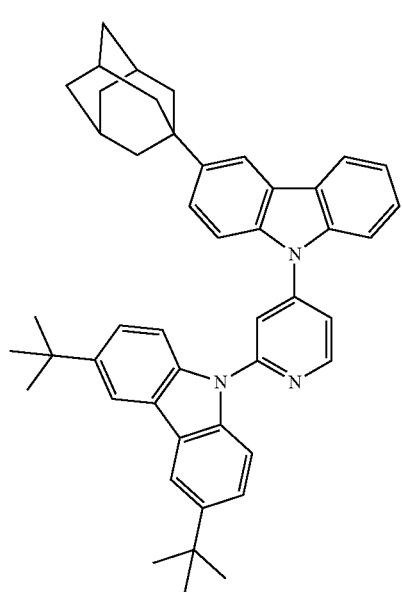
1-18
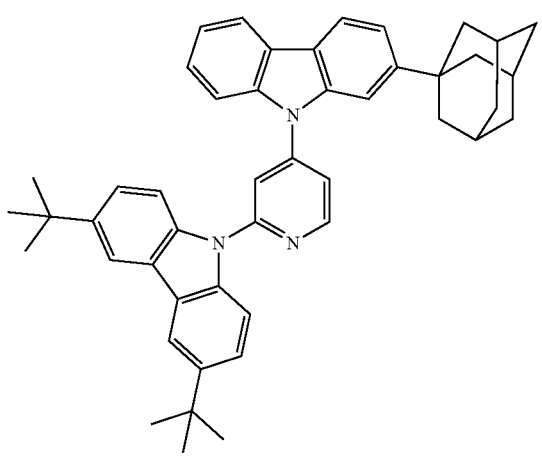
1-16
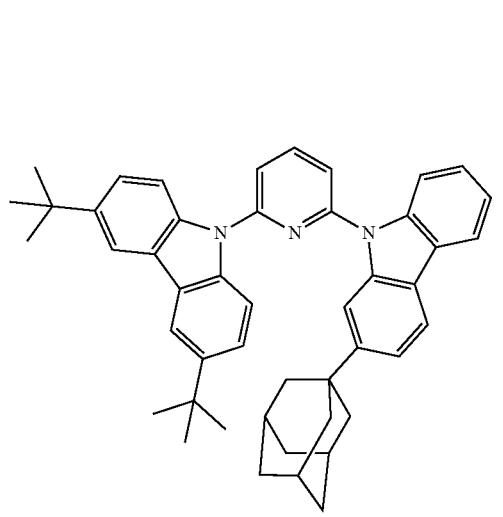
1-19
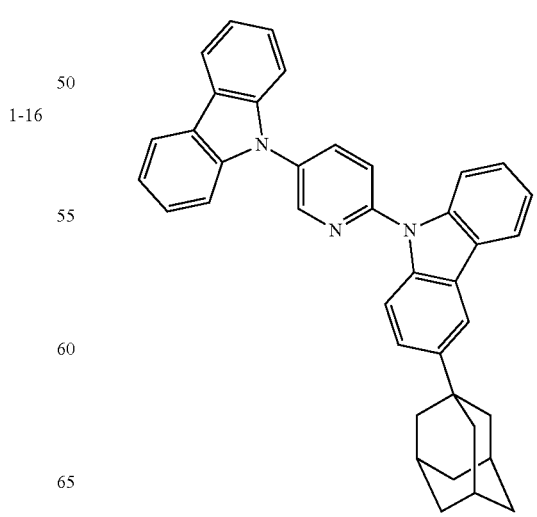

1-20
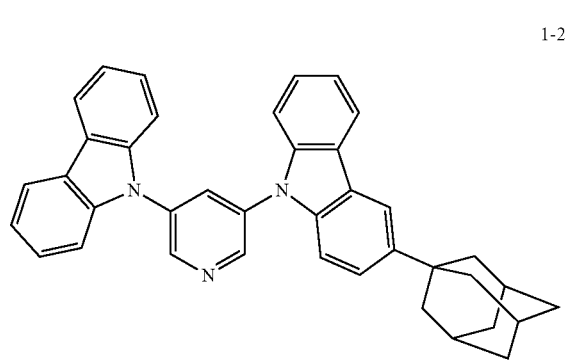
1-21
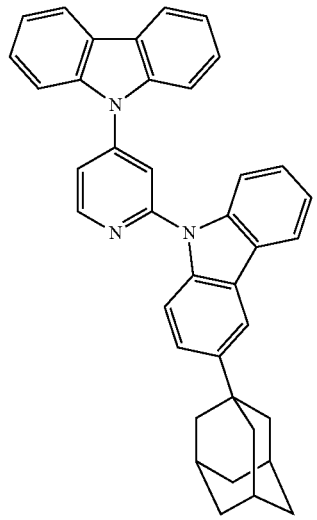
1-22
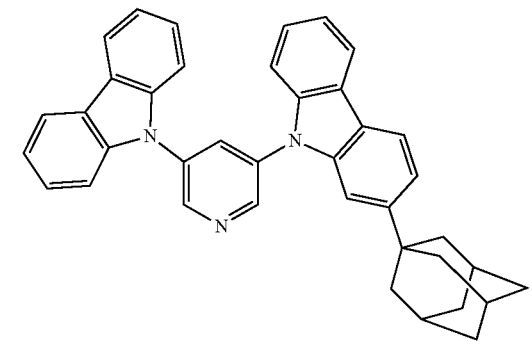
1-23
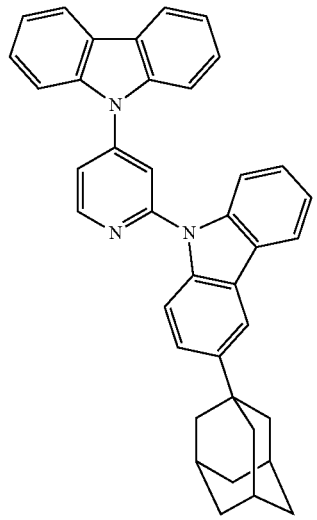
1-24
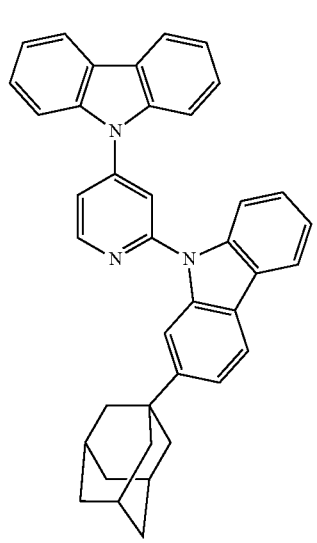
1-25
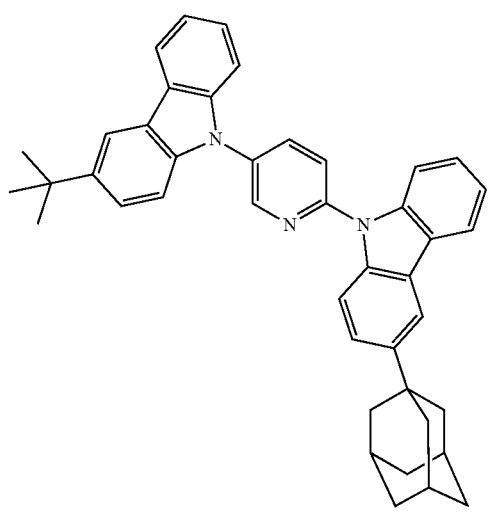

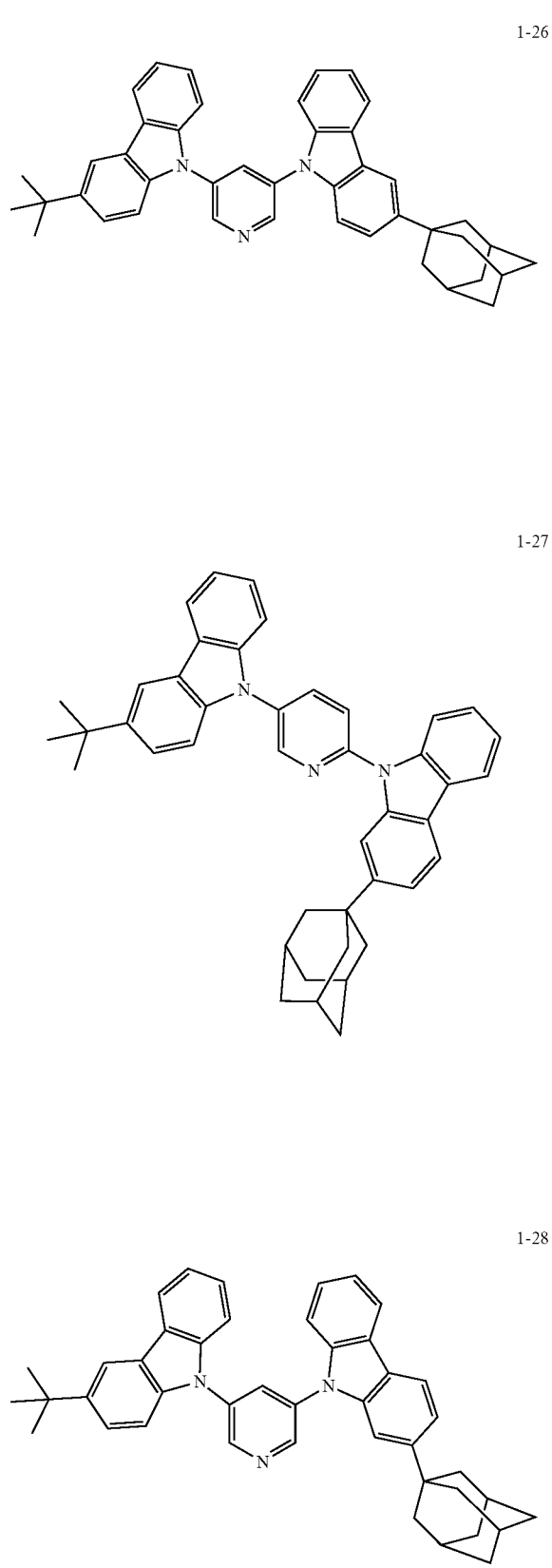
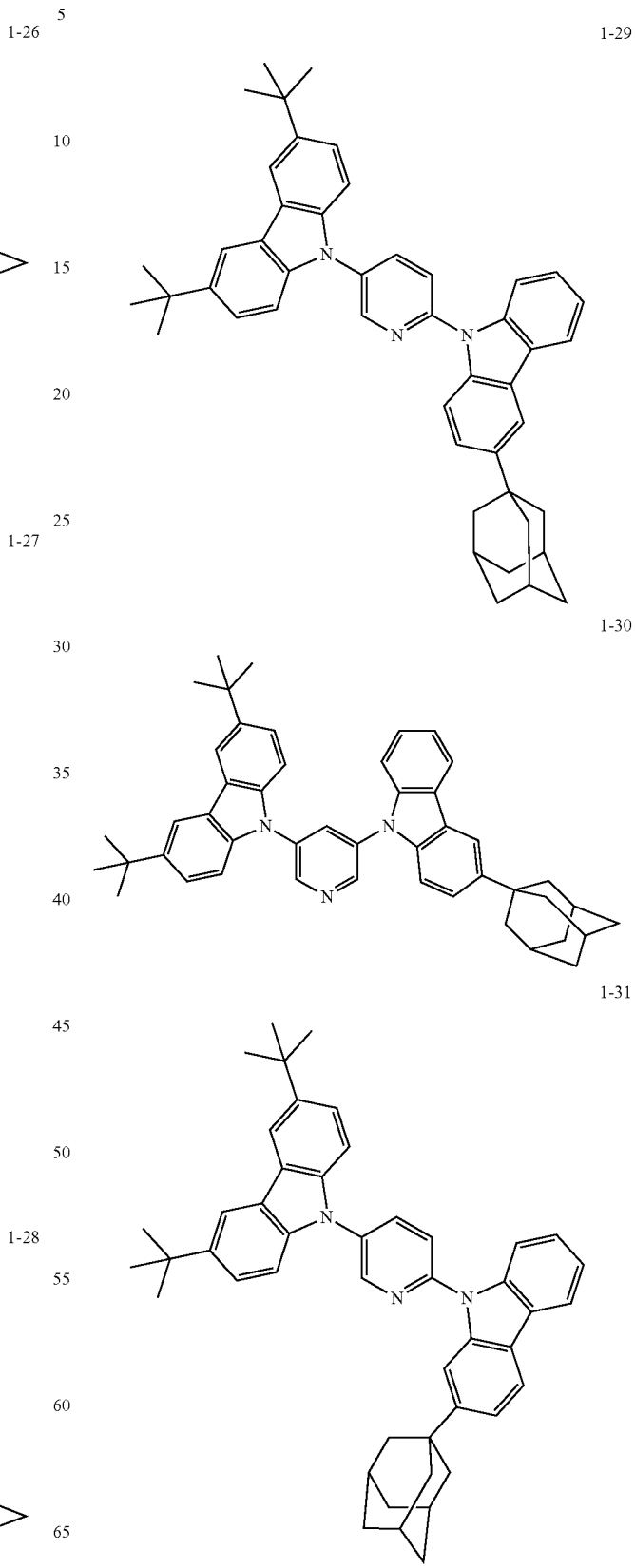

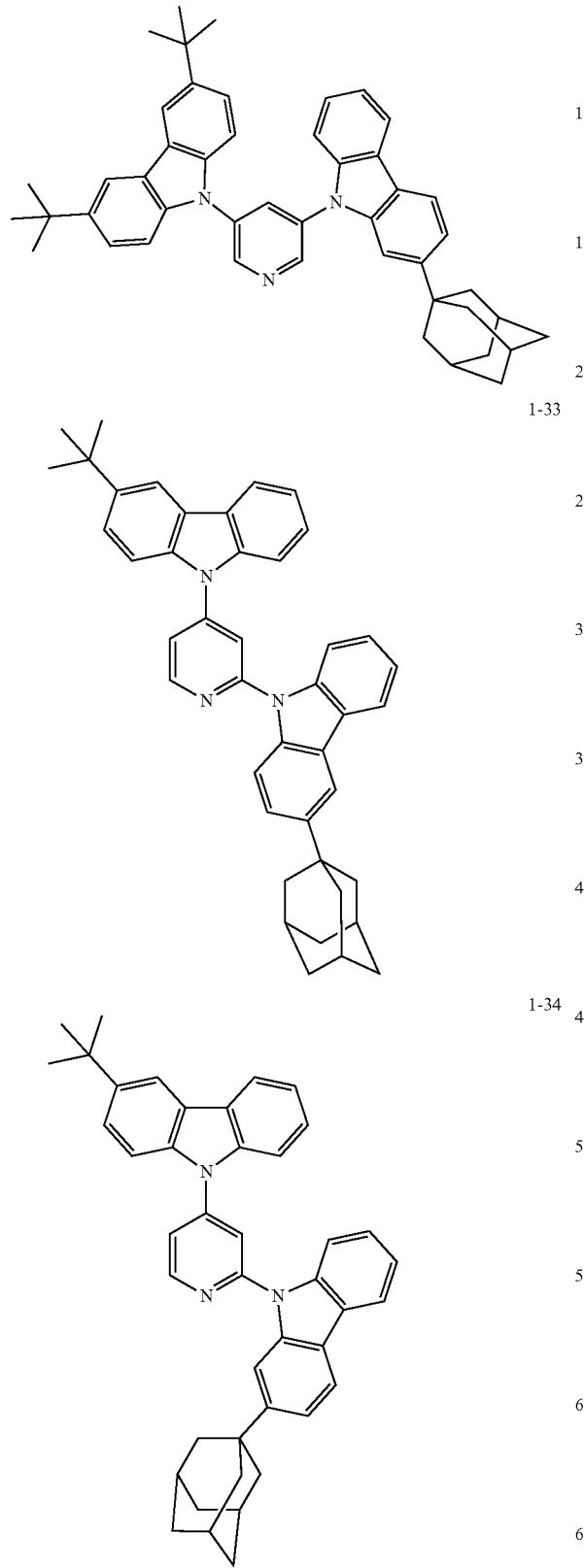
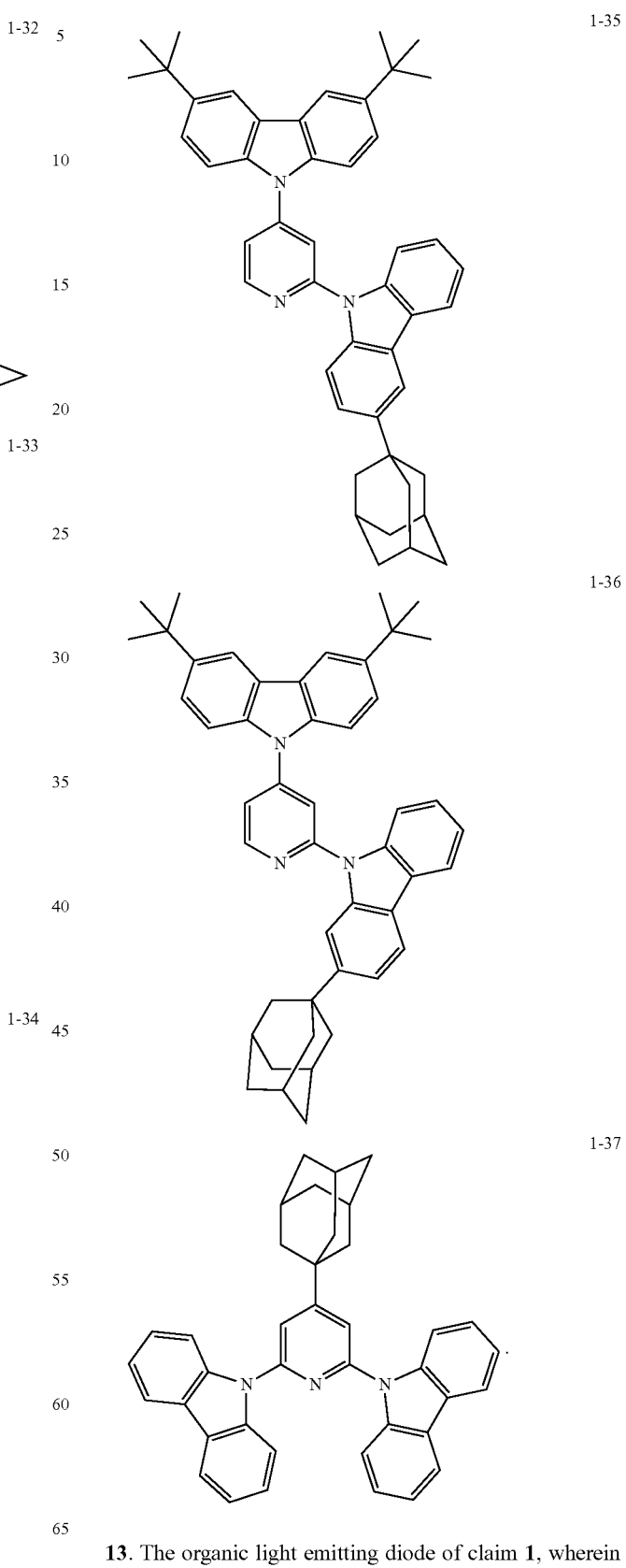
13. The organic light emitting diode of claim 1, wherein the organic compound is selected from:

2-1
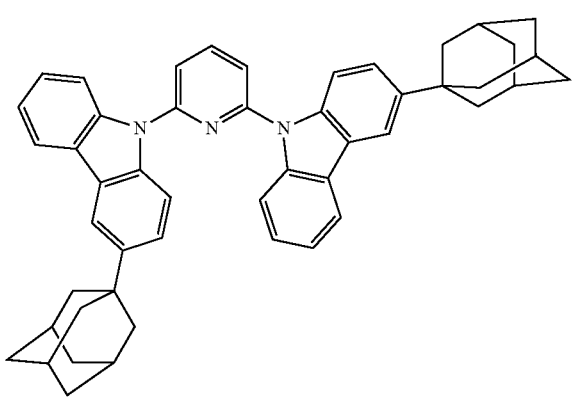
2-2
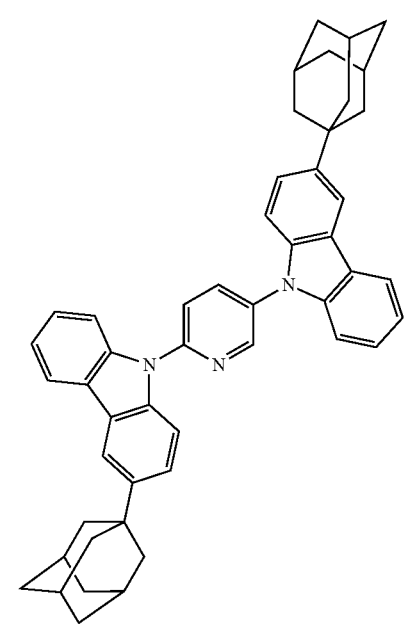
2-3
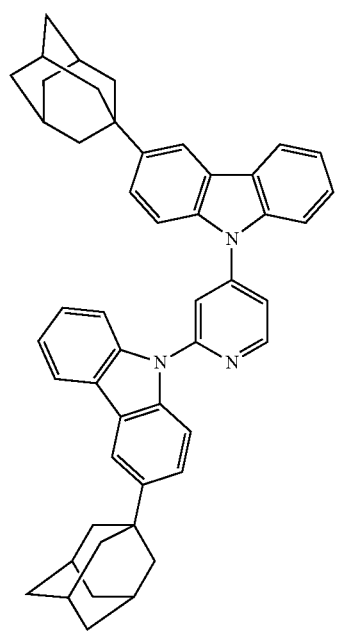
2-4
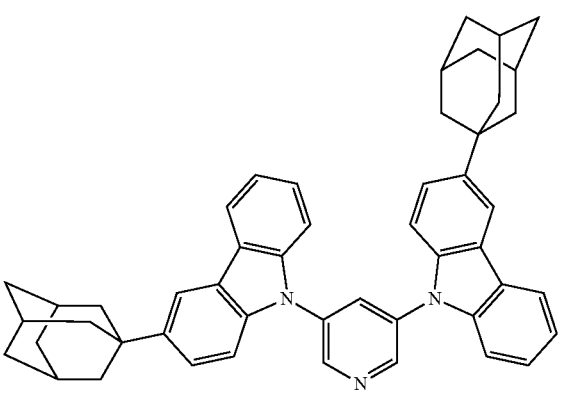
2-5
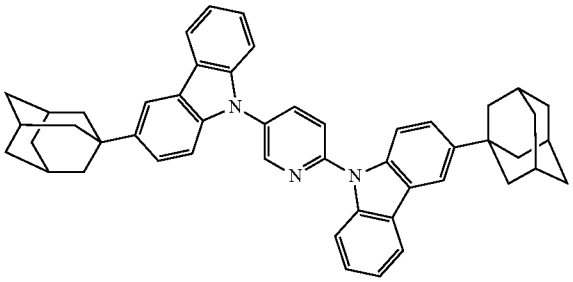
2-6
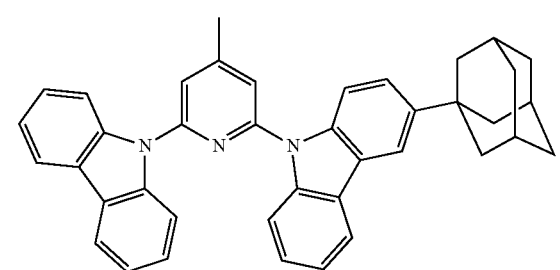

14. The organic light emitting diode of claim 1, wherein the organic compound is selected from:

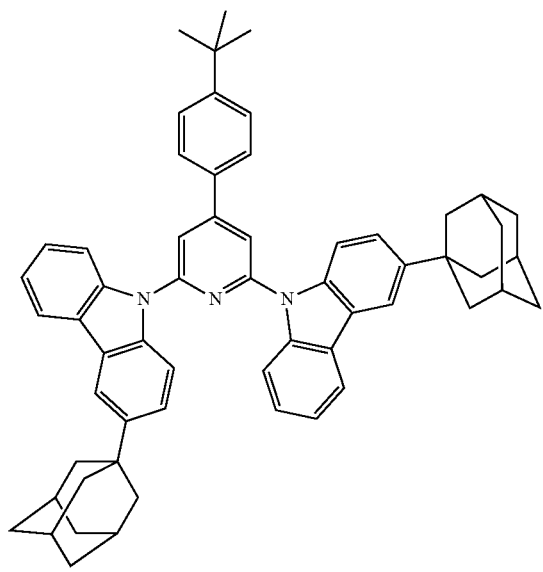
2-7

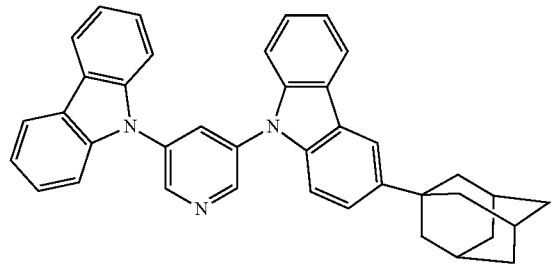
1-20

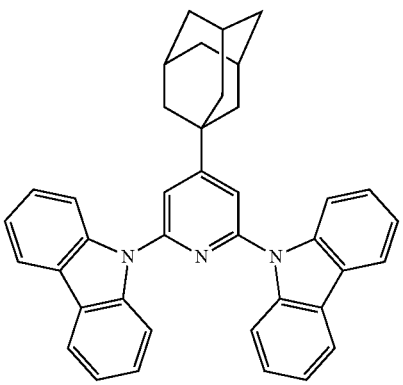
1-37

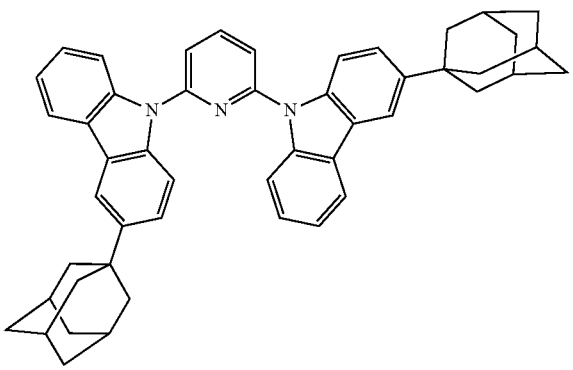
2-1

15. The organic light emitting diode of claim 6, wherein the second compound comprises a delayed fluorescent material.

16. The organic light emitting diode of claim 8, wherein the fifth compound comprises a fluorescent material or a phosphorescent material.

17. The organic light emitting diode of claim 9, wherein the seventh compound comprises a fluorescent material or a phosphorescent material.

* * * * *